US011541121B2

(12) United States Patent
Herrmann et al.

(10) Patent No.: US 11,541,121 B2
(45) Date of Patent: *Jan. 3, 2023

(54) PHOSPHOROTHIOATE-CONJUGATED PEPTIDES AND METHODS OF USING THE SAME

(71) Applicant: CITY OF HOPE, Duarte, CA (US)

(72) Inventors: Andreas Herrmann, Del Mar, CA (US); Hua Yu, Glendora, CA (US); Toshikage Nagao, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/630,343

(22) PCT Filed: Jul. 13, 2018

(86) PCT No.: PCT/US2018/042177
§ 371 (c)(1),
(2) Date: Jan. 10, 2020

(87) PCT Pub. No.: WO2019/014648
PCT Pub. Date: Jan. 17, 2019

(65) Prior Publication Data
US 2021/0145973 A1  May 20, 2021

Related U.S. Application Data

(60) Provisional application No. 62/532,147, filed on Jul. 13, 2017.

(51) Int. Cl.
*A61K 47/54* (2017.01)
*A61P 31/18* (2006.01)
*A61P 29/00* (2006.01)
*A61P 35/00* (2006.01)
*A61K 38/17* (2006.01)

(52) U.S. Cl.
CPC ........ *A61K 47/549* (2017.08); *A61K 38/1709* (2013.01); *A61K 38/1774* (2013.01); *A61P 29/00* (2018.01); *A61P 31/18* (2018.01); *A61P 35/00* (2018.01)

(58) Field of Classification Search
CPC .............. A61K 47/549; A61K 38/1709; A61K 38/1774; A61K 49/00; A61P 35/00; A61P 29/00; A61P 31/18; C12Q 1/68
See application file for complete search history.

(56) References Cited

U.S. PATENT DOCUMENTS

| 5,994,515 | A | 11/1999 | Hoxie |
| 7,291,721 | B2 | 11/2007 | Giles-Komar et al. |
| 10,967,070 | B2* | 4/2021 | Herrmann ............... C07K 16/18 |
| 2007/0269435 | A1 | 11/2007 | Gillies et al. |
| 2008/0102055 | A1 | 5/2008 | Chiba et al. |
| 2008/0213258 | A1 | 9/2008 | Massague et al. |
| 2011/0236972 | A1 | 9/2011 | Quay et al. |
| 2016/0263235 | A1 | 9/2016 | Castaigne et al. |
| 2016/0317671 | A1* | 11/2016 | Herrmann ............... A61K 39/44 |
| 2016/0362744 | A1 | 12/2016 | Jaisser et al. |
| 2017/0008970 | A1 | 1/2017 | Babcook et al. |
| 2018/0230237 | A1* | 8/2018 | Herrmann ............... C07K 16/18 |
| 2018/0243436 | A1* | 8/2018 | Yu ........................... A61P 35/00 |
| 2021/0154305 | A1* | 5/2021 | Herrmann ............ A61K 47/549 |

FOREIGN PATENT DOCUMENTS

| WO | WO2015/031837 | * | 3/2015 | ............ A61K 38/14 |
| WO | WO-2016/115500 A1 | | 7/2016 | |
| WO | WO-2017/024238 A1 | | 2/2017 | |
| WO | WO-2017/024239 A1 | | 2/2017 | |

OTHER PUBLICATIONS

Antopolsky et al. Peptide-Oligonucleotide Phosphorothioate Conjugates with Membrane Translocation and Nuclear Localization Propoerties. Bioconjugate Chem. 1999, vol. 10, pp. 598-606. (Year: 1999).*
Schaeffer et al. Synthesis and Applications of Covalent Protein-DNA Conjugates. Aust. J. Chem. 2009, vol. 62, pp. 1328-133. (Year: 2009).*
Jayaraman et al. Rational selection and quantitative evaluation of antisense oligonucleotides. Biochimica et Biophysica Acta, 1520, pp. 105-114. (Year: 2001).*
Al Zaid Siddiquee, K. et al. (Feb. 2008). "STAT3 as a target for inducing apoptosis in solid and hematological tumors," *Cell Res* 18(2):254-267.
Extended European Search Report dated Feb. 12, 2021, for EP Patent Application No. 18832584.9, 9 pages.
Herrmann, A. et al. (2014). "STAT3 nuclear egress requires exportin 7 via engaging lysine acetylation," *MOJ Cell Science & Report* 1(1): 1(1): 00004.
International Search Report dated Nov. 19, 2018, for PCT Application No. PCT/US2018/042177, filed Jul. 13, 2018, 7 pages.
Jain, H.V. et al. (Mar. 2016). "An Amphipathic trans-Acting Phosphorothioate DNA Element Delivers Uncharged PNA and PMO Nucleic Acid Sequences in Mammalian Cells," *Curr Protoc Nucleic Acid Chem* 64(1):4.69.1-4.69.22.
Sazani, P. et al. (Oct. 1, 2001). "Nuclear antisense effects of neutral, anionic and cationic oligonucleotide analogs," *Nucleic Acids Res* 29(19):3965-3974.
Written Opinion dated Nov. 19, 2018, for PCT Application No. PCT/US2018/042177, filed Jul. 13, 2018, 12 pages.

(Continued)

*Primary Examiner* — Marcela M Cordero Garcia
(74) *Attorney, Agent, or Firm* — Mintz Levin Cohn Ferris Glovsky and Popeo, P.C.

(57) ABSTRACT

Provided herein are, inter alia, nucleic acid-peptide conjugates including a non-cell penetrating protein attached at its C-terminus to a phosphorothioate nucleic acid. Attachment of the phosphorothioate nucleic acid to the non-cell penetrating protein conveys stability to and allows for efficient intracellular delivery of the non-cell penetrating peptide. The nucleic acid-peptide conjugates provided herein including embodiments thereof are useful, inter alia, for the treatment of cancer, inflammatory disease, pain, and viral infection.

19 Claims, 66 Drawing Sheets

Specification includes a Sequence Listing.

(56) References Cited

OTHER PUBLICATIONS

Bidwell, G.L. III (Apr. 2, 2009, e-published Nov. 28, 2008). "Targeting a c-Myc inhibitory polypeptide to specific intracellular compartments using cell penetrating peptides," *J Control Release* 135(1):2-10.

Ren, Z. et al. (Feb. 24, 2003). "Identification of a high-affinity phosphopeptide inhibitor of Stat3," *Bioorg Med Chem Lett* 13(4):633-636.

Turkson, J. et al. (Nov. 30, 2001). "Phosphotyrosyl peptides block Stat3-mediated DNA binding activity, gene regulation, and cell transformation," *J Biol Chem* 276(48):45443-45455.

\* cited by examiner

FIG. 5A

|  | STAT3-peptide | LINKER | PS-ssDNA 20mer |
|---|---|---|---|
| PS-mod. STAT3-(acetyl)K685-peptide | PDIPKEEAFGK(Ac)YCRPESQEHPC | -linker- | T*C*C*A*T*G*A*G*C*T*T*C*C*T*G*A*T*G*C*T |
| PS-mod. STAT3-K685R-peptide | PDIPKEEAFGRYCRPESQEHPC | -linker- | T*C*C*A*T*G*A*G*C*T*T*C*C*T*G*A*T*G*C*T |
| PS-mod. STAT3-WT-peptide | PDIPKEEAFGKYCRPESQEHPC | -linker- | T*C*C*A*T*G*A*G*C*T*T*C*C*T*G*A*T*G*C*T | gp130-Y767   VHSGpYRHQVPS-linker-T*C*C*A*T*G*A*G*C*T*T*C*C*T*G*A*T*G*C*T
gp130-Y905   MPKSpYLPQTV-linker-A*G*C*A*T*C*A*G*G*A*A*G*C*T*C*A*T*G*G*A
gp130-915    RQGGpYMPQ-linker-T*C*C*A*T*G*A*G*C*T*T*C*C*T*G*A*T*G*C*T

FIG. 24A

PS-mod. STAT3-(acet)K685-peptide
PDIPKEEAFGK(Ac)YCRPESQEHPC-linker-T*C*C*A*T*G*A*G*C*T*T*C*C*T*G*A*T*G*C*T PO-mod. STAT3-(acet)K685-peptide
PDIPKEEAFGK(Ac)YCRPESQEHPC-linker-TCCATGAGCTTCCTGATGCT PS-mod. STAT3-WT-peptide
PDIPKEEAFGKYCRPESQEHPC-linker-T*C*C*A*T*G*A*G*C*T*T*C*C*T*G*A*T*G*C*T PO-mod. STAT3-WT-peptide
PDIPKEEAFGKYCRPESQEHPC-linker-TCCATGAGCTTCCTGATGCT PS-mod. STAT3-K685R-peptide
PDIPKEEAFGRYCRPESQEHPC-linker-T*C*C*A*T*G*A*G*C*T*T*C*C*T*G*A*T*G*C*T PO-mod. STAT3-K685R-peptide
PDIPKEEAFGRYCRPESQEHPC-linker-T*C*C*A*T*G*A*G*C*T*T*C*C*T*G*A*T*G*C*T

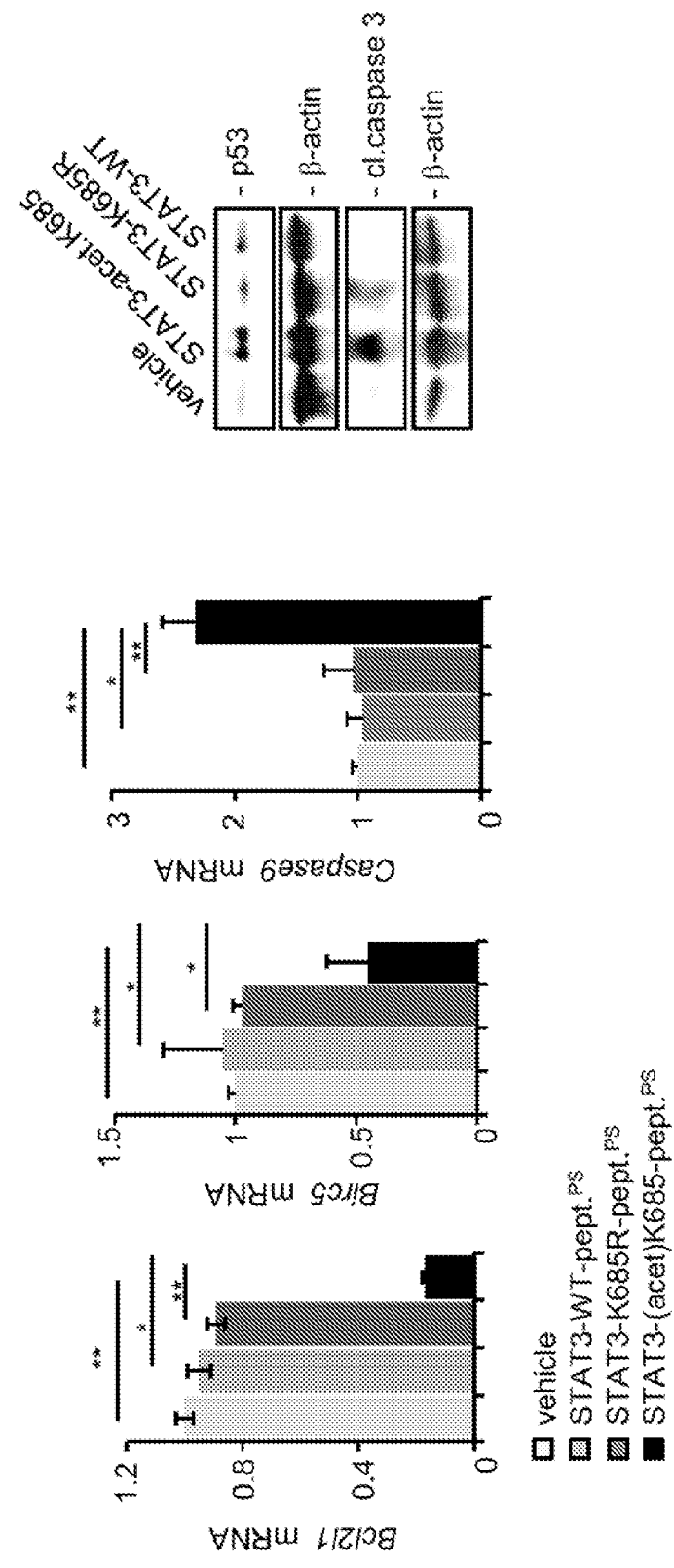

PHOSPHOROTHIOATE-CONJUGATED PEPTIDES AND METHODS OF USING THE SAME

CROSS REFERENCE TO RELATED APPLICATIONS

This application is a National Stage filing of International Patent Application No. PCT/US2018/042177, filed Jul. 13, 2018, which claims priority to U.S. Provisional Application No. 62/532,147, filed Jul. 13, 2017, the contents of which are hereby incorporated by reference in their entireties and for all purposes.

STATEMENT AS TO RIGHTS TO INVENTIONS MADE UNDER FEDERALLY SPONSORED RESEARCH AND DEVELOPMENT

This invention was made using support under Grant Number CA122976 awarded by the National Institutes of Health. The government has certain rights to this invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048440 592001WO_ST25.TXT, created Jul. 13, 2018, 31,928 bytes, machine format IBM-PC, MS Windows operating system, is hereby incorporated by reference.

BACKGROUND OF THE INVENTION

The manipulation of intracellular molecules involved in disease pathology is an attractive treatment option for numerous diseases. The ability to modify the activity of intracellular molecules can have profound effects on intracellular signaling pathways and result in changes in gene expression that promote favorable disease outcome. However, targeting intracellular molecules for therapeutic purposes is particularly challenging due to the need for the targeting molecule to both penetrate the cell membrane and maintain biostability in a physiological environment. Thus, there is a need in the art for biostable, cell-penetrating compositions capable of targeting intracellular molecules involved in disease pathology.

Provided herein are compositions and methods including targeting peptides conjugated to phophorothioate nucleic acids at their C-terminus which exhibit surprising biostability and can be delivered intracellulary with high efficiency. The phosphorothioate nucleic acid-peptide conjugates provided herein are, inter alia, useful for the treatment of various disease including cancer, inflammation and viral infection.

BRIEF SUMMARY OF THE INVENTION

In an aspect is provided a nucleic acid-peptide conjugate including: (i) a non-cell penetrating peptide; (ii) a phosphorothioate nucleic acid; and (iii) a chemical linker attaching the phosphorothioate nucleic acid to the C-terminus of the non-cell penetrating peptide; wherein the phosphorothioate nucleic acid enhances intracellular delivery of the non-cell penetrating peptide.

In an aspect is provided a conjugate dimer is provided. The conjugate dimer includes: (i) a first nucleic acid-peptide conjugate including: (a) a first non-cell penetrating peptide; (b) a phosphorothioate nucleic acid; and (c) a first chemical linker attaching the phosphorothioate nucleic acid to the C-terminus of the first non-cell penetrating peptide; and (ii) a second nucleic acid-peptide conjugate including: (a) a second non-cell penetrating peptide; (b) a non-phosphorothioated nucleic acid; and (c) a second chemical linker attaching the non-phosphorothioated nucleic acid to the C-terminus of the second non-cell penetrating peptide; wherein the phosphorothioate nucleic acid and the non-phosphorothioated nucleic acid are hybridized to bind the first nucleic acid-peptide conjugate to the second nucleic acid-peptide conjugate thereby forming a conjugate dimer.

In an aspect is provided a cell including the peptide conjugate provided herein including embodiments thereof.

In an aspect is provided a pharmaceutical composition including the peptide conjugate as provided herein including embodiments thereof and a pharmaceutically acceptable carrier.

In an aspect is provided a method of treating cancer in a subject in need thereof. The method includes administering to the subject a therapeutically effective amount of a cell penetrating peptide conjugate as provided herein including embodiments thereof, thereby treating the cancer in the subject.

In an aspect is provided a method of increasing expression of p53 in a cancer cell, the method including contacting a cancer cell with an effective amount of a cell penetrating peptide conjugate as provided herein including embodiments thereof, thereby increasing expression of p53 in the cancer cell.

In an aspect is provided a method of inhibiting tumor vascularization in a subject in need thereof, the method including administering to the subject a therapeutically effective amount of a cell penetrating peptide conjugate as provided herein including embodiments thereof, thereby inhibiting tumor vascularization in the subject.

In an aspect is provided a method of treating an inflammatory disease in a subject in need thereof, the method including administering to the subject a therapeutically effective amount of a cell penetrating peptide conjugate as provided herein including embodiments thereof, thereby treating an inflammatory disease in the subject.

In an aspect is provided a method of treating pain in a subject in need thereof, the method including administering to the subject a therapeutically effective amount of a cell penetrating peptide conjugate as provided herein including embodiments thereof, thereby treating pain in the subject.

In an aspect is provided a method of treating a viral infection in a subject in need thereof, the method including administering to the subject a therapeutically effective amount of a cell penetrating peptide conjugate as provided herein including embodiments thereof, thereby treating the viral infection in the subject.

In an aspect is provided a method of inhibiting viral entry into a cell, the method including contacting a cell with an effective amount of a cell penetrating peptide conjugate as provided herein including embodiments thereof, thereby inhibiting viral entry into the cell.

In an aspect is provided a method of inhibiting IL6 receptor signaling in a cell, the method including contacting a cell with an effective amount of a cell penetrating peptide conjugate as provided herein including embodiments thereof, thereby inhibiting IL6 receptor signaling in the cell.

In an aspect is provided a method of delivering a non-cell penetrating peptide into a cell, the method including contacting a cell with the cell penetrating peptide conjugate as provided herein including embodiments thereof, thereby delivering the non-cell penetrating peptide into the cell.

BRIEF DESCRIPTION OF THE DRAWINGS

FIG. 3A. Human glioma U251 cells were incubated for 2 hrs with 10 µg/ml peptide as indicated (i.e., {STAT3}pept-wt [SEQ ID NO:6], {STAT3}pept-KR [SEQ ID NO:7], {STAT3}pept-acet.K [SEQ ID NO:3]). PS means that the peptide indicated peptide was elongated with phosphorothioate nucleic acids while PO means that the peptides were elongated with non-phosphorothioated nucleic acids. Fixed cells were analyzed by confocal microscopy for intracellular peptide localization. Scale, 20 µm. FIG. 3B. Human glioma U251 cells were incubated for 2 hrs with 1 µg/ml peptide as indicated ({STAT3}pept-wt [SEQ ID NO:6], {STAT3}pept-KR [SEQ ID NO:7], {STAT3}pept-acet.K [SEQ ID NO:3]) and analyzed by flow cytometry to assess immediate early cellular load of cells with modified peptide.

FIGS. 5A-5B: The STAT3 competitor peptide is acetylated at a central lysine. FIG. 5A. Peptide sequences derived from human STAT3 protein and the non-specific sequence of PS-ssDNA 20mer (SEQ ID NO:13) are shown. The lysine residue located in the center of the peptide corresponds to lysine 685 in STAT3 protein which is known to undergo acetylation in tumor and inflammatory responses of cells and tissue. Man-made lysine acetylated competitor peptide shows antitumoral activity, while lysine mutation to arginine R (middle) or wild-type (bottom) corresponding sequences has no or little effect on tumor growth kinetics. All peptides were extended into phosphorothioated ssDNA oligos to facilitate cellular internalization. FIG. 5B. The acetylated STAT3 competitor peptide engages with exportin 7 as shown from in vitro assay, precipitating the peptide using the FITC fluorophore as a tag which was incorporated into the linker region of peptides. Precipitates were analyzed by Western blotting for physical interaction with exportin 7 inside human glioma U251 cells.

FIG. 6A. Human colon cancer tumor bearing mice were treated daily with 20 mg peptide as indicated and tumor volume was assessed. SD shown, T-test: *) $P<<0.05$, **) $P<0.01$. FIG. 6B. Reduced interaction of STAT3 and exportin 7 was assessed from tumor tissue homogenates by co-precipitation analyzed by Western blotting.

FIG. 7A. Induced p53 tumor suppressor expression and elevated tumor cell death indicated by cleaved caspase 3 was assessed by Western blot analyses of tumor homogenates. FIG. 7B. Ki67+ proliferative activity and CD31+ tumor vessels were (FIG. 7C) significantly reduced as analyzed by confocal microscopy and its quantification. Scale, 100 µm. SD shown, T-test: ) $P<0.01$, *) $P<0.001$.

FIG. 12A. Peripheral blood was drawn and murine sera were subjected to electrophoretic protein separation by SDS-PAGE showing dramatically increased biostability upon PS-modification by detecting the FITC moiety of the PS-modifiedFITC+-STAT3-peptide. FIG. 12B. Organs as indicated were dissected upon systemic peptide treatment as indicated and analyzed for accumulation of peptides showing exclusively the PS-modified STAT3 peptide undergoes retention. CD31+ blood vessels were included to visualize potential blood vessel damage.

FIG. 13A. Shown is the one letter amino acid sequence covering a stretch of the gp130 protein. STAT3 docking sites were modified and man-made phosphorylated. To achieve cellular internalization, the peptide was extended at its C-terminus by a linker followed by a 20meric ssDNA stretch. It is critical that the sugar-phosphate backbone is phosphorothioated (PS; upper) indicated by (*) to achieve cellular internalization. Two non-specific sequences of PS-ssDNA 20mer (SEQ ID NO:13 and SEQ ID NO:14) are also shown. FIG. 13B. Scheme highlighting the STAT3 recruitment sites in gp130 which have been used to design the peptide motifs to compete for STAT3 recruitment and activation by the receptor tipping the balance to non-tyrosine phosphorylated STAT3.

FIG. 14A. Human multiple myeloma cells MM.1S were treated as indicated with 0.5 µM phosphorothioate elongated gp130-peptide (i.e., PS-2263165 is phosphorothioate elongated SEQ ID NO:4, PS-1209196 is phosphorothioate elongated SEQ ID NO:8, and PS-2263163 is phosphorothioate elongated SEQ ID NO:9) for either 30 or 90 min and cellular internalization was assessed by flow cytometry. FIG. 14B. Human hepatoma HepG2 cells were treated as indicated with 1.0 µM gp130-peptide (i.e., PS-2263165 is phosphorothioate elongated SEQ ID NO:4, PS-1209196 is phosphorothioate elongated SEQ ID NO:8, and PS-2263163 is phosphorothioate elongated SEQ ID NO:9) for either 60 min or 90 min and cellular internalization was assessed by confocal microscopy.

FIG. 19A and FIG. 19C show representative lung tissues excised from mice treated as described above. FIG. 19B shows the mean numbers of the colonies (n=5).

FIG. 20A. Phosphorothioated DNA oligonucleotide-modified STAT3 peptides efficiently penetrate human glioma cell line U251 and human colon cancer cell line HCT116, as assessed by flow cytometry. FIG. 20B. Cell penetration of the PS-acetyl-STAT3 peptide and its colocalization with STAT3 protein in U251 cells are shown by confocal microscopy. Scale, 50 µm. FIG. 20C and FIG. 20D. The PS acetyl-STAT3 peptide specifically binds to acetylated STAT3 protein and exportin 7, as assessed by ELISA, in which the plate is coated by an acetylated-STAT3 protein (containing amino acids 127-722), n=3. FIG. 20E and FIG. 20F. The specific interaction between acetyl-STAT3 peptide and STAT3/exportin 7 shown by immunoprecipitation of the FITC-labeled PS-acetyl-STAT3 peptide followed by Western blotting, shown in U251 cells. FIG. 20G. Downregulation of STAT3 phosphorylation, shown in HCT116 tumors by immunoprecipitation/Western blotting. FIG. 20H. PS-acetyl-STAT3 peptide treatment induces apoptosis of HCT116 colorectal cancer cells. FIG. 20I. Conjugating phosphorothioation DNA oligonucleotides to acetyl-STAT3 peptide increases its biostability, shown by Western blotting to detect FITC labeled-peptide in blood serum of C57BL/6 mice collected 24 h after treatment.

FIG. 21A. Growth kinetics of HCT116 tumors in NSG mice systemically treated with acetyl-STAT3 peptides (18.940 µM), with or without the PS oligonucleotide conjugation, every other day (n=5). SD shown; T-test; *; $P<0.001$; , $P<0.01$; *, $P<0.05$. FIG. 21B. Downregulation of STAT3 activity upon treatments with PS-acetyl-STAT3 peptides, as shown by immunoprecipitation followed by Western blotting.

FIG. 21C. Effects of downregulation of STAT3 activity on expression of proliferation- and apoptosis-related genes, as assessed by qRT-PCR in tumor homogenates from tumors shown in A. The mRNA expression levels in the tumor tissues from the control mice are set as 1. T-test; *; $P<0.001$; , $P<0.01$; *, $P<0.05$. FIG. 21D. Treatment with the PS-acetyl-STAT3 peptide induces apoptosis and inhibits proliferation and angiogenesis in tumors, as indicated by confocal imaging after H&E staining (upper panel), and immunostaining of Ki-67 and CD-31 proteins in the tumor sections (lower panels). The images are representative of 3 tumors per experimental group in A. Scale bars: 50 µm. The graphs show the quantification for Ki-67 expression levels and of the mean vessel diameter (data include 6 fields of view per group). SD shown. ** $P<0.01$.

FIG. 22A. Structures of non-phosphorothioated (PO) and phosphorothioated DNA oligonucleotide-modified acetyl-STAT3 peptides. Dimerization of the peptides is achieved by annealing anti- and sense DNA oligos. FIG. 22B. Dimerization of non-phosphorothioated and phosphorothioated DNA oligonucleotide-modified peptides is shown by SDS-PAGE. FIG. 22C. Dimerization enhances cell penetration of the peptide, assessed by flow cytometry. FIG. 22D. The enhanced anti-tumor effect of the dimerized PS-acetyl-STAT3 peptide is shown in HCT116 tumors grown in NSG mice (n=5). T-test; **, $P<0.01$; *, $P<0.05$. FIG. 22E. The dimerized PS-acetyl-STAT3 peptide more effectively downregulates pY705-STAT3 (upper panel) and induces p53 expression (lower panel) than its monomer counterpart, as analyzed by immunoprecipitation and Western blotting with tumor homogenates from the tumors in E. FIG. 22F. qRT-PCR showing mRNA levels of STAT3-regulated pro-apoptotic and pro-survival genes in HCT116 tumor tissues treated with the indicated STAT3 peptides. The mRNA expression levels in the tumor tissues treated with control vehicle are set as 1. T-test; *; $P<0.001$; , $P<0.01$; *, $P<0.05$. FIG. 22G. On-target effects of the dimerized PS-acetyl-STAT3 peptide, assessed by qRT-PCR. The graph shows the differential expression of the downstream genes of JAK/STAT3 signaling pathway in the HCT116 tumor tissues treated with dimerized PS-acetyl-STAT3 peptide compared to vehicle. FIG. 22H. Immunohistochemical analyses of tumor sections from tumors shown in E, followed by confocal microscopy. The anti-tumor effects of dimerized PS-acetyl-STAT3 peptide are compared to its monomer counterpart. Images are representative of 3 tumors per experimental group. Scale bars: 50 µM (upper panel). Lower panels show the quantified Ki-67 protein levels as well as mean of vessel diameter (data include 5 fields of view per group).

FIG. 23A. In vitro penetration of PS-acetyl-STAT3 peptide into CD8+ T cells, as assessed by flow cytometry. CD8+ T cells were isolated from C57BL/6 mouse spleens. FIG. 23B. ELISA shows that treating splenic CD8+ T cells with the PS-acetyl-STAT3 peptide upregulates IFNγ and IL-2 expression, as expected from STAT3 inhibition. T-test; *; $P<0.001$. Assays were done in triplicates. FIG. 23C. Downregulation of IL-6-induced pY705-STAT3 in splenic CD8+ T cells treated with PS-acetyl-STAT3 peptide compared to controls, as analyzed by Western blotting. FIG. 23D. The PS-acetyl-STAT3 peptide reduces B16 lung nodules in syngeneic mouse model compared with control treatments (left panel). Right panel shows numbers of lung nodules in mice treated with the indicated STAT3 peptides and vehicle (n=5). T-test; , $P<0.01$; *, $P<0.05$. n.s: not significant. FIG. 23E and FIG. 23F. Immunochemical staining followed by confocal microscopy to detect the CD69+ tumor infiltrating CD8+ T cells and CD4+FoxP3+ T cell population in B16 lung nodules (same as in D) upon treatment with vehicle, PO- and PS-acetyl-STAT3 peptides. Images are representative of 3 lungs per experimental group. The graphs show the quantification of CD8, CD69 and FoxP3+ expression levels (data include 6 fields of view per group). SD shown. ***; $P<0.001$; *, $P<0.05$.

FIGS. 24A-24C: The PS-acetyl-STAT3 peptide penetration and bio-functionality. FIG. 24A. Structures of the modified STAT3 peptides. FIG. 24B. The PS-STAT3 peptides penetrate into HCT116 cancer cells, shown by immunofluorescence. Scale bars: 20 µm. FIG. 24C. Treatment with the PS-acetyl-STAT3 peptide induces p53 overexpression in HCT116 colon cancer cells, assessed by Western blotting.

FIGS. 25A-25E: PS-acetyl-STAT3 peptide treatments suppress the growth of HCT116 colon tumors. FIG. 25A. Peritumoral treatment of subcutaneous (s.c.) HCT116 tumors in NSG mice with 18.940 µM PS-STAT3-WT, PS-STAT3-K685R or PS-STAT3-acet.-K685 peptides, starting 7 days after the mice were challenged with 5×106 HCT116 cells, n=4. Treatments were performed every day. SD shown. *; $P<0.001$; , $P<0.01$; *, $P<0.05$. FIG. 25B. Western blotting shows STAT3 activity levels upon treatments with indicated acetyl-STAT3 peptides. FIG. 25C. mRNA levels of STAT3-downstream proliferation- and apoptosis-related genes as assessed by qRT-PCR using tumor homogenates prepared from tumors shown in A. The mRNA expression levels in the tumors treated with control vehicle are set as 1. T-test; *; $P<0.001$; , $P<0.01$; *, $P<0.05$. FIG. 25D. Upregulation of pro-apoptotic proteins, p53 and cl. caspase 3, in HCT 116 tumor homogenates from tumors shown in A, assessed by Western blotting. FIG. 25E. The PS-acetyl-STAT3 peptide penetrates into HCT116 tumors shown in A, and downregulates tumor Ki-67 and CD31 proteins, as visualized by confocal microscopy following immunohistochemical staining. Scale bar: 100 µm. Quantifications for Ki-67 and CD31 proteins in the treated tumors are shown in right panels. The graphs show the quantification of Ki67 and CD31 (data include 6 fields of view per group). SD shown. $P<0.01$; *$P<0.001$.

FIG. 26A. The growth kinetic shows HCT116 tumors in NSG mice, treated with 18.940 µM PO- or PS-acetyl-STAT3 peptides locally every day (n=4). SD is shown by asterisks. T-test; * $P<0.05$. FIG. 26B. PS-acetyl-STAT3 peptide binds to exportin 7, shown by immunoprecipitation and Western blotting using tumor homogenates prepared from tumors shown in A. FIG. 26C. Treatment with PS-acetyl-STAT3 peptide induces tumor apoptosis, indicated by H&E staining (upper panel) and Cytochrome C and Lamin B1 protein expression levels (middle and lower panels). Panels show representative images from 3 tumors from each experimental group. Scale bars: 20 µm. Quantifications for Cytochrome C and Lamin B1 are shown in the right panels (data include 5 fields of view per group). SD is shown.  $P<0.01$. FIG. 26D. Ki-67 and CD31 protein expression levels in tumors treated with vehicle, PO- or PS-acetyl-STAT3 peptide, as analyzed by confocal microscopy. Scale bar: 100 µm. Right panels show quantifications of Ki-67 protein levels and mean of vessel diameter (data include 5 fields of view per group). SD is shown. *; $P<0.001$; **, $P<0.01$; *, $P<0.05$. FIG. 26E. Western blotting showing p53 and cl. caspase 3 overexpression in the tumors shown in A (left panel). The increased p53 protein expression in HCT116 tumors treated with the PS-acetyl-STAT3 peptide is shown by immunohistochemical staining followed by confocal microscopy imaging. The images represent tumor sections from 3 tumors per experimental group (n=3). Scales; 20 µm.

FIG. 26F. mRNA levels for CASP9, BIRC5 and Bcl2L1 in the same tumor tissues described above are assessed by qRT-PCR. The mRNA levels of the same genes from tumors without peptide treatments are set as 1. SD is shown. ***P<0.001.

FIG. 28A. Growth kinetics of paclitaxel-resistant MDA-MB-231 TNBC tumors in NSG mice. Tumors were systemically treated with vehicle (HBSS−/−) and the PS-acetyl-STAT3 peptide every other day. FIG. 28B. Downregulation of STAT3 phosphorylation by the PS-acetyl-STAT3 peptides in TNBC tumors shown in A. FIG. 28C. Confocal images of indicated immunochemical staining show apoptotic and proliferation degrees in tumor tissues shown in A (left panels). Images representatively show tissue sections from 3 tumors per experimental group. Scales; 50 and 100 μm. Right panel is the quantification of Ki67 expression levels (data include 6 fields of view per group). SD shown. *; P<0.001. FIG. 28D. qRT-PCR shows mRNA levels of the indicated proliferation and apoptosis genes in the TNBC tumor tissues. The mRNA expression levels in the tumor tissues from the mice without peptide treatment are set as 1. SD shown *, P<0.001; **, P<0.01; *, P<0.05.

FIG. 29A. Cell penetration of FITC-PS-GP130- and PS-c-MYC-inhibitory peptides in W76964 (mouse pancreatic cancer cell line) cells. c-MYC-inhibitory peptide directly binds to c-MYC protein and prevents the full-length c-MYC from interacting with Max and thus blocking c-MYC-Max dimerization. $1\times10^6$ cells were incubated with 10 μg of PS-GP130- or PS-c-MYC-peptide for 2 hours at 37° C. The efficiency of cell penetration was determined by flow cytometry. FIG. 29B. W76964 cells were engrafted in C57BL/6 mice to generate tumors. After tumor size reached approximately 80 mm³, PO-Gp130 or PS-GP130 was mixed with PS-c-MYC-inhibitory peptide (1:1 ratio) to treat mice systemically (i.v.) at 20 μg every other day. Tumor size was measured by a caliber. Tumor volume was calculated (V=(L×W×W)), where V is tumor volume, W is tumor width, L is tumor length. When some tumors start to reach 600 mm³, all groups of mice were euthanized at the same time using protocols approved by IACUC of City of Hope. N=6 as indicated.

DETAILED DESCRIPTION OF THE INVENTION

Definitions

Figure 1:
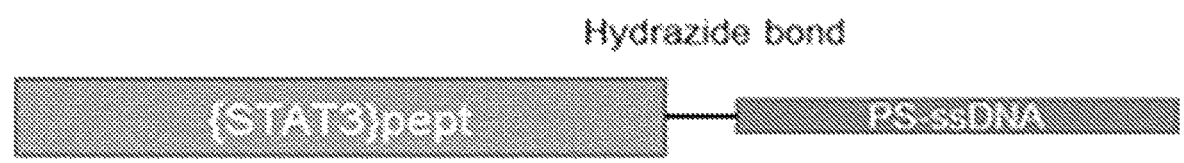
FIG. 1: Cartoon illustrating the connection of modified peptide sequences derived from the human STAT3 protein (STAT3-peptide) via a Linker to a phosphorothioate ssDNA (PS-ssDNA).

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂-. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and –R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section or Drawings.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, monophosphate (or derivatives thereof), diphosphate (or derivatives thereof), triphosphate (or derivatives thereof), in a number ranging from zero to (2 m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$-, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R")$_d$—, where s and d are independently integers of from 0 to 3, and X' is —O—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC═(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC═(O)H, —NHC(O)—OH, —NHOH, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —NHNH$_2$, —ONH$_2$, —NHC(O) NHNH$_2$, —NHC(O) NH$_2$, —NHSO$_2$H, —NHC═(O)H, —NHC(O)—OH, —NHOH, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The symbol "⌇" denotes the point of attachment of a chemical moiety to the remainder of a molecule or chemical formula.

A "chemical linker" or "linker" as provided herein is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties can be chemically different.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted C$_1$-C$_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple $R^1$ substituents are present, each $R^1$ substituent may be distinguished as $R^{1A}$, $R^{1B}$, $R^{1C}$, $R^{1D}$, etc., wherein each of $R^{1A}$, $R^{1B}$, $R^{1C}$, $R^{1D}$, etc. is defined within the scope of the definition of $R^1$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "phosphorothioate nucleic acid" refers to a nucleic acid in which one or more internucleotide linkages are through a phosphorothioate moiety (thiophosphate) moiety. The phosphorothioate moiety may be a monothiophosphate ($-P(O)_3(S)^{3-}-$) or a dithiophosphate ($-P(O)_2(S)_2^{3-}-$). In embodiments of all the aspects provided herein, the phosphorothioate moiety is a monothiophosphate ($-P(O)_3(S)^{3-}-$). That is, in embodiments of all the aspects provided herein, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety ($-P(O)_4^{3-}-$). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments. the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the interneucleotide linkages of a phosphorothioate nucleic acid can be phosphorothioate linkages. Optionally, 5%, 10%, 15%, 20%, 25%, 30%, 35%, 40%, 45%, 50%, 55%, 60%, 65%, 70%, 75%, 80%, 85%, 90%, 95%, or 99% of the internucleotide linkages of a phosphorothioate nucleic acid are phosphorothioate linkages. Optionally, 50%, 55%, 60%, 65%, 70%, 75%, 80%, 85%, 90%, 95%, or 99% of the internucleotide linkages of a phosphorothioate nucleic acid are phosphorothioate linkages. Optionally, 75%, 80%, 85%, 90%, 95%, or 99% of the internucleotide linkages of a phosphorothioate nucleic acid are phosphorothioate linkages. Optionally, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. Optionally, 50%, 55%, 60%, 65%, 70%, 75%, 80%, 85%, 90%, 95%, or 99%, of the intersugar linkages in a phosphorothioate polymer backbone can be phosphorothioate linkages. Optionally, 75%, 80%, 85%, 90%, 95%, or 99%, of the intersugar linkages in a phosphorothioate polymer backbone can be phosphorothioate linkages. Optionally, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, 100% of the intersugar linkages of the phosphorothioate polymer backbone are phosphorothioate linkages.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art. In embodiments, the phosphorothioate nucleic acid or phosphorothioate polymer backbone is connected to a detectable label through a chemical linker.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The phosphorothioate nucleic acids and phosphorothioate polymer backbones provided herein can include one or more reactive moieties, e.g., a covalent reactive moiety. A reactive moiety may be attached to the remainder of the phosphorothioate nucleic acids and phosphorothioate polymer backbones using any appropriate linker, such as a polymer linker known in the art or alternatively a polyethylene glygcol linker or equivalent. The linker may, in embodiments, include (i.e. be attached to) a detectable label as described herein. As used herein, the term "covalent reactive moiety" refers to a chemical moiety capable of chemically reactive with an amino acid of a non-cell penetrating protein, as described herein, to form a covalent bond and, thus, a conjugate as provided herein.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell.

The term "exogenous" refers to a molecule or substance (e.g., a compound, nucleic acid peptide, or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance (e.g., protein or peptide) that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., STAT3 or gp130) in other proteins with different numbering systems. For example, by performing a simple sequence alignment with a protein (e.g., STAT3 or gp130) the identity and location of residues corresponding to specific positions of said protein are identified in other protein sequences aligning to said protein. For example, a selected residue in a selected protein corresponds to lysine at position 685 when the selected residue occupies the same essential spatial or other structural relationship as a lysine at position 685. In some embodiments, where a selected protein is aligned for maximum homology with a protein, the position in the aligned selected protein aligning with lysine 685 is said to correspond to lysine 685. Instead of a primary sequence alignment, a three dimensional structural alignment can also be used, e.g., where the structure of the selected protein is aligned for maximum correspondence with the lysine at position 685, and the overall structures compared. In this case, an amino acid that occupies the same essential position as lysine 685 in the structural model is said to correspond to the lysine 685 residue.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The terms "STAT3," "STAT3 protein," "STAT3 peptide" as referred to herein include any of the recombinant or naturally-occurring forms of the Signal transducer and activator of transcription 3 (STAT3) protein or variants or homologs thereof that maintain STAT3 protein activity (e.g. within at least 50%, 80%, 90%, 95%, 96%, 97%, 98%, 99% or 100% activity compared to STAT3). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring STAT3 polypeptide. In embodiments, the STAT3 peptide is substantially identical to the protein identified by the UniProt reference number P40763 or a variant or homolog having substantial identity thereto. In embodiments, the STAT3 peptide includes the sequence of SEQ ID NO:1. In embodiments, the STAT3 peptide is the sequence of SEQ ID NO:1.

The term "exportin 7" as referred to herein includes any of the recombinant or naturally-occurring forms of the exportin 7 protein or variants or homologs thereof that maintain exportin 7 protein activity (e.g. within at least 50%, 80%, 90%, 95%, 96%, 97%, 98%, 99% or 100% activity compared to exportin 7). Exportin 7 is a member of the super-family karyopherins, which is comprised of factors including importins and exportins important for trafficking cargo into and out of the nucleus, respectively. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring exportin 7 polypeptide. In embodiments, the exportin 7 protein is substantially identical to the protein identified by the UniProt reference number Q9UIA9 or a variant or homolog having substantial identity thereto. In embodiments, the exportin 7 protein includes the sequence of SEQ ID NO:5. In embodiments, the exportin 7 protein is the sequence of SEQ ID NO:5.

The terms "MAX" or "MAX protein" as referred to herein includes any of the recombinant or naturally-occurring forms of the myc-associated factor X (MAX) or variants or homologs thereof that maintain MAX protein activity (e.g. within at least 50%, 80%, 90%, 95%, 96%, 97%, 98%, 99% or 100% activity compared to MAX). MAX is a transcription regulator, which forms a sequence-specific DNA-binding protein complex with MYC or MAD that may recognize the core sequence 5'-CAC[GA]TG-3'. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MAX polypeptide. In embodiments, the MAX protein is substantially identical to the protein identified by the UniProt reference number P61244 or a variant or homolog having substantial identity thereto. In embodiments, the MAX protein includes the sequence of SEQ ID NO:12. In embodiments, the MAX protein includes the sequence of SEQ ID NO:10. In embodiments, the MAX protein is the sequence of SEQ ID NO:12.

As used herein, the terms "cell-penetrating" or "cell-penetration" refer to the ability of a molecule (e.g. a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule to pass from the extracellular environment into a cell in a significant or effective amount. Thus, non-cell penetrating peptides or proteins generally are not capable of passing from the extracellular environment, through the cell membrane, and into a cell in order to achieve a significant biological effect on a population of cells, organ or organism. The term does not exclude the possibility that one or more of the small number of peptides or proteins may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins. Peptides or proteins can be determined to be non-cell penetrating using methods known to those of skill in the art. By way of example, a peptide or protein can be fluorescently labeled and the ability of the peptide or protein to pass from the extracellular environment into the cell can be determined in vitro by flow cytometric analysis or confocal microscopy. In some embodiments, a "non-cell penetrating protein" refers to a protein that penetrates a cell at least about 2, 3, 4, 5, 6, 7, 8, 9, 10, 20, 30, 40, 50, 60, 70, 80, 90, 100, 200, 300, 400, 500, 600, 700, 800, 900, 1000, 10,000 or 100,000 fold less than the same protein attached to a phosphorothioate nucleic acid or phosphorothioate polymer backbone. In some embodiments, a "non-cell penetrating protein" refers to a protein that does not measurably penetrate a cell.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating proteins provided herein bind. Binding can be direct or indirect. Optionally, the non-cell penetrating protein selectively binds the intracellular target. By selectively binds, selectively binding, or specifically binding refers to the agent (e.g., a non-cell penetrating protein) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIO-CONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the phosphorothioate nucleic acid and phosphorothioate backbone polymer are non-covalently attached to the protein through a non-covalent chemical reaction between a component of the phosphorothioate nucleic acid and phosphorothioate backbone polymer (e.g. a monothiophosphate) and a component of the protein (e.g. an amino acid).

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The term "activating," as used herein, refers to an nucleic acid-peptide conjugate capable of detectably increasing the expression or activity of a given gene or protein (e.g., p53). The activating nucleic acid-peptide conjugate can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid-peptide conjugate.

As defined herein, the term "inhibition", "inhibit", "inhibiting" and the like in reference to an nucleic acid-peptide conjugate interaction means negatively affecting (e.g. decreasing) the activity or function of a protein (e.g., exportin 7) relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a non-cell penetrating peptide (e.g., STAT3) as described herein and an intracellular target (e.g., exportin 7).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

The terms "subject," "patient," "individual," etc. are not intended to be limiting and can be generally interchanged. That is, an individual described as a "patient" does not necessarily have a given disease, but may be merely seeking medical advice.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (cutaneous T-cell lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

Nucleic Acid-Peptide Conjugates

Provided herein are, inter alia, nucleic acid-peptide conjugates including a non-cell penetrating protein attached at its C-terminus to a phosphorothioate nucleic acid. Attachment of the phosphorothioate nucleic acid to the non-cell penetrating protein conveys stability to and allows for efficient intracellular delivery of the non-cell penetrating peptide. Upon entry into a cell the non-cell penetrating peptides provided herein may target and modify the activity of intracellular molecules involved in disease pathology thereby improving disease outcome. The nucleic acid-peptide conjugates provided herein including embodiments thereof are useful, inter alia, for the treatment of cancer, inflammatory disease, pain, and viral infection.

Figure 22A:
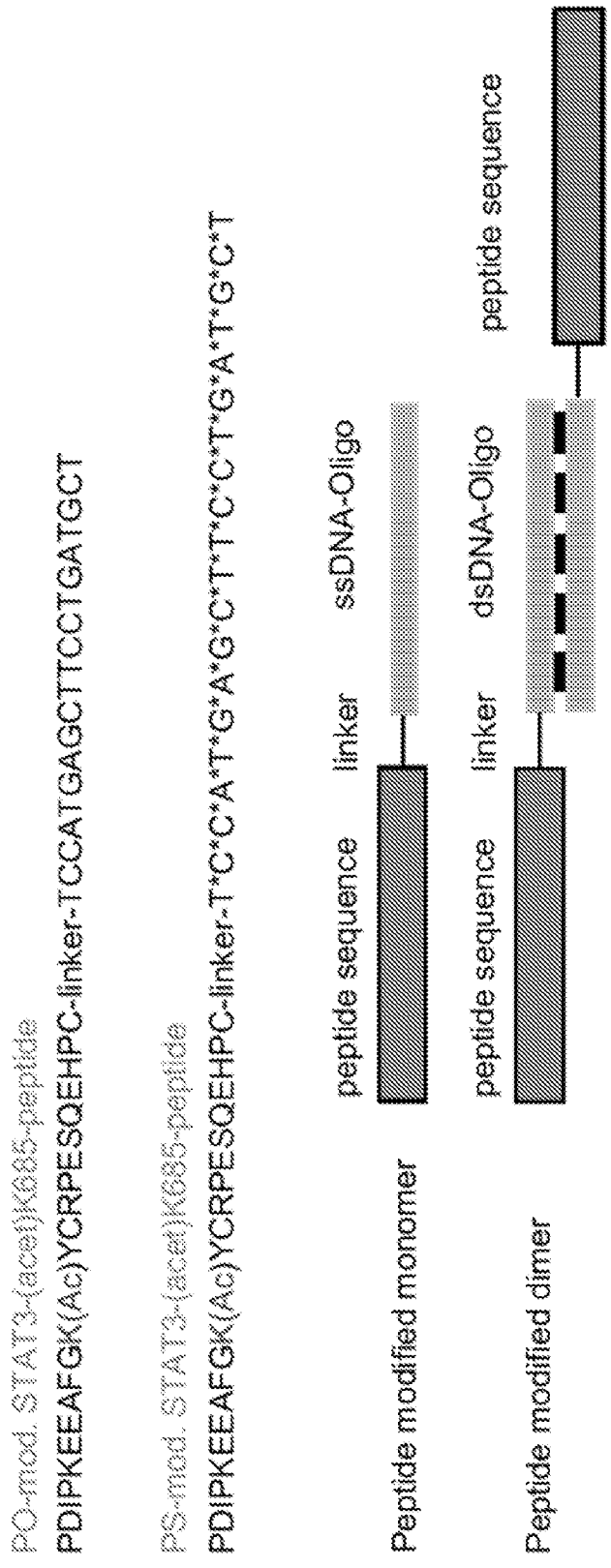
FIGS. 22A-22H: Dimerization of the PS-acetyl-STAT3 peptide increases its anti-tumor effects.

Further provided herein are conjugate dimers including a first nucleic acid-peptide conjugate as described herein and a second nucleic acid-peptide conjugate, wherein the second nucleic acid-peptide conjugate includes a second non-cell penetrating peptide as described herein and a non-phosphorothioated nucleic acid; and a second chemical linker attaching the non-phosphorothioated nucleic acid to the C-terminus of the second non-cell penetrating peptide. Through base pairing of the phosphorothioate nucleic acid of the first nucleic acid-peptide conjugate with the non-phosphorothioated nucleic acid of the second nucleic acid-peptide conjugate, the first nucleic acid-peptide conjugate forms a dimer with the second nucleic acid-peptide conjugate. The conjugate dimers provided herein are contemplated for all uses and compositions provided herein including embodiments thereof. Exemplary conjugate dimers useful for the invention provided are shown in FIG. 22A and FIG. 24A.

In an aspect is provided a conjugate dimer is provided. The conjugate dimer includes: (i) a first nucleic acid-peptide conjugate including: (a) a first non-cell penetrating peptide; (b) a phosphorothioate nucleic acid; and (c) a first chemical linker attaching the phosphorothioate nucleic acid to the C-terminus of the first non-cell penetrating peptide; and (ii) a second nucleic acid-peptide conjugate including: (a) a second non-cell penetrating peptide; (b) a non-phosphorothioated nucleic acid; and (c) a second chemical linker attaching the non-phosphorothioated nucleic acid to the C-terminus of the second non-cell penetrating peptide; wherein the phosphorothioate nucleic acid and the non-phosphorothioated nucleic acid are hybridized to bind the first nucleic acid-peptide conjugate to the second nucleic acid-peptide conjugate thereby forming a conjugate dimer.

In an aspect is provided a nucleic acid-peptide conjugate including: (i) a non-cell penetrating peptide; (ii) a phosphorothioate nucleic acid; and (iii) a chemical linker attaching the phosphorothioate nucleic acid to the C-terminus of the non-cell penetrating peptide; wherein the phosphorothioate nucleic acid enhances intracellular delivery of the non-cell penetrating peptide.

As used herein, the term "C-terminus" is synonymous with carboxyl-terminus, carboxy-terminus, C-terminal tail, C-terminal end, and COOH-terminus, is used in accordance with its ordinary meaning in biology and refers to the termination moiety of an amino acid sequence. For example, the C-terminus may refer to the last amino acid in an amino acid sequence, e.g.,

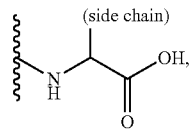

wherein side chain refers to the amino acid side chain). In embodiments, the C-terminus includes a carboxylic acid moiety.

In embodiments, the non-cell penetrating peptide is about 5, 10, 15, 20 or 25 amino acids in length. In embodiments, the non-cell penetrating peptide is about 5 amino acids in length. In embodiments, the non-cell penetrating peptide is 5 amino acids in length. In embodiments, the non-cell penetrating peptide is about 8 amino acids in length. In embodiments, the non-cell penetrating peptide is 8 amino acids in length. In embodiments, the non-cell penetrating peptide is about 10 amino acids in length. In embodiments, the non-cell penetrating peptide is 10 amino acids in length. In embodiments, the non-cell penetrating peptide is about 11 amino acids in length. In embodiments, the non-cell penetrating peptide is 11 amino acids in length. In embodiments, the non-cell penetrating peptide is about 13 amino acids in length. In embodiments, the non-cell penetrating peptide is 13 amino acids in length. In embodiments, the non-cell penetrating peptide is about 15 amino acids in length. In embodiments, the non-cell penetrating peptide is 15 amino acids in length. In embodiments, the non-cell penetrating peptide is about 22 amino acids in length. In embodiments, the non-cell penetrating peptide is 22 amino acids in length. In embodiments, the non-cell penetrating peptide is about 20 amino acids in length. In embodiments, the non-cell penetrating peptide is 20 amino acids in length. In embodiments, the non-cell penetrating peptide is about 25 amino acids in length. In embodiments, the non-cell penetrating peptide is 25 amino acids in length.

In embodiments, the non-cell penetrating peptide is at least 5 (e.g., 5, 6, 7, 8, 9, 10, 11, 12, 13, 14, 15, 16, 17, 18, 19, 20, 21, 22, 23, 24, 25, 26, 26, 28, 29, 30, 35, 40, 45, 50) amino acids in length. In embodiments, the non-cell penetrating peptide is at least 6 amino acids in length. In embodiments, the non-cell penetrating peptide is at least 7 amino acids in length. In embodiments, the non-cell penetrating peptide is at least 8 amino acids in length. In embodiments, the non-cell penetrating peptide is at least 9 amino acids in length. In embodiments, the non-cell penetrating peptide is at least 10 amino acids in length. In embodiments, the non-cell penetrating peptide is at least at least 11 amino acids in length. In embodiments, the non-cell penetrating peptide is at least 12 amino acids in length. In embodiments, the non-cell penetrating peptide is at least 13 amino acids in length. In embodiments, the non-cell penetrating peptide is at least 14 amino acids in length. In embodiments, the non-cell penetrating peptide is at least 15 amino acids in length. In embodiments, the non-cell penetrating peptide is at least 16 amino acids in length. In embodiments, the non-cell penetrating peptide is at least 17 amino acids in length. In embodiments, the non-cell penetrating peptide is at least 18 amino acids in length. In embodiments, the non-cell penetrating peptide is at least 19 amino acids in length. In embodiments, the non-cell penetrating peptide is at least 20 amino acids in length. In embodiments, the non-cell penetrating peptide is at least 21 amino acids in length. In embodiments, the non-cell penetrating peptide is at least 22 amino acids in length. In embodiments, the non-cell penetrating peptide is at least 23 amino acids in length. In embodiments, the non-cell penetrating peptide is at least 24 amino acids in length. In embodiments, the non-cell penetrating peptide is at least 25 amino acids in length. In embodiments, the non-cell penetrating peptide is at least 26 amino acids in length. In embodiments, the non-cell penetrating peptide is at least 27 amino acids in length. In embodiments, the non-cell penetrating peptide is at least 28 amino acids in length. In embodiments, the non-cell penetrating peptide is at least 29 amino acids in length. In embodiments, the non-cell penetrating peptide is at least 30 amino acids in length. In embodiments, the non-cell penetrating peptide is at least 35 amino acids in length. In embodiments, the non-cell penetrating peptide is at least 40 amino acids in length. In embodiments, the non-cell penetrating peptide is at least 45 amino acids in length. In embodiments, the non-cell penetrating peptide is at least 50 amino acids in length.

In embodiments, the non-cell penetrating peptide has a molecular weight of less than about 25 kD (e.g., 24, 23, 22, 21, 20, 19, 18, 17, 16, 15, 14, 13, 12, 11, 10, 5, 1 kD). In embodiments, the non-cell penetrating peptide has a molecular weight of less than about 24 kD. In embodiments, the non-cell penetrating peptide has a molecular weight of less than about 23 kD. In embodiments, the non-cell penetrating peptide has a molecular weight of less than about 22 kD. In embodiments, the non-cell penetrating peptide has a molecular weight of less than about 21 kD. In embodiments, the non-cell penetrating peptide has a molecular weight of less than about 20 kD. In embodiments, the non-cell penetrating peptide has a molecular weight of less than about 19 kD. In embodiments, the non-cell penetrating peptide has a molecular weight of less than about 18 kD. In embodiments, the non-cell penetrating peptide has a molecular weight of less than about 17 kD. In embodiments, the non-cell penetrating peptide has a molecular weight of less than about 16 kD. In embodiments, the non-cell penetrating peptide has a molecular weight of less than about 15 kD. In embodiments, the non-cell penetrating peptide has a molecular weight of less than about 14 kD. In embodiments, the non-cell penetrating peptide has a molecular weight of less than about 13 kD. In embodiments, the non-cell penetrating peptide has a molecular weight of less than about 12 kD. In embodiments, the non-cell penetrating peptide has a molecular weight of less than about 11 kD. In embodiments, the non-cell penetrating peptide has a molecular weight of less than about 10 kD. In embodiments, the non-cell penetrating peptide has a molecular weight of less than about 5 kD. In embodiments, the non-cell penetrating peptide has a molecular weight of less than about 1 kD. In embodiments, the non-cell penetrating peptide has a molecular weight of less than 25 kD. In embodiments, the non-cell penetrating peptide has a molecular weight of less than 24 kD. In embodiments, the non-cell penetrating peptide has a molecular weight of less than 23 kD. In embodiments, the non-cell penetrating peptide has a molecular weight of less than 22 kD. In embodiments, the non-cell penetrating peptide has a molecular weight of less than 21 kD. In embodiments, the non-cell penetrating peptide has a molecular weight of less than 20 kD. In embodiments, the non-cell penetrating peptide has a molecular weight of less than 19 kD. In embodiments, the non-cell penetrating peptide has a molecular weight of less than 18 kD. In embodiments, the non-cell penetrating peptide has a molecular weight of less than 17 kD. In embodiments, the non-cell penetrating peptide has a molecular weight of less than 16 kD. In embodiments, the non-cell penetrating peptide has a molecular weight of less than 15 kD. In embodiments, the non-cell penetrating peptide has a molecular weight of less than 14 kD. In embodiments, the non-cell penetrating peptide has a molecular weight of less than 13 kD. In embodiments, the non-cell penetrating peptide has a molecular weight of less than 12 kD. In embodiments, the non-cell penetrating peptide has a molecular weight of less than 11 kD. In embodiments, the non-cell penetrating peptide has a molecular weight of less than 10 kD. In embodiments, the non-cell penetrating peptide has a molecular weight of less than about 5 kD. In embodiments, the non-cell penetrating peptide has a molecular weight of less than 1 kD.

In embodiments, the non-cell penetrating peptide is not an antibody or an antibody fragment. In embodiments, the non-cell penetrating peptide is less than about 25 amino acids in length. In embodiments, the non-cell penetrating peptide is less than 25 amino acids in length. In embodiments, the non-cell penetrating peptide is less than about 24 amino acids in length. In embodiments, the non-cell penetrating peptide is less than 24 amino acids in length. In embodiments, the non-cell penetrating peptide is less than about 23 amino acids in length. In embodiments, the non-cell penetrating peptide is less than 23 amino acids in length. In embodiments, the non-cell penetrating peptide is less than about 22 amino acids in length. In embodiments, the non-cell penetrating peptide is less than 22 amino acids in length. In embodiments, the non-cell penetrating peptide is less than about 21 amino acids in length. In embodiments, the non-cell penetrating peptide is less than 21 amino acids in length. In embodiments, the non-cell penetrating peptide is less than about 20 amino acids in length. In embodiments, the non-cell penetrating peptide is less than 20 amino acids in length. In embodiments, the non-cell penetrating peptide is less than about 15 amino acids in length. In embodiments, the non-cell penetrating peptide is less than 15 amino acids in length. In embodiments, the non-cell penetrating peptide is less than about 10 amino acids in length. In embodiments, the non-cell penetrating peptide is less than 10 amino acids in length.

The non-cell penetrating peptides provided herein including embodiments thereof may include modified amino acids. Examples of modified amino acids include without limitation, chemically modified naturally occurring amino acids, chemically modified synthetic amino acids, as well as chemically modified amino acid analogs and amino acid mimetics. Modified naturally occurring amino acids may be modified post-translationally in a cell or synthetically in a reaction vessel. The presence of a modified amino acid may convey alternate functional and/or structural features to the peptide it forms part of relative to the corresponding non-modified amino acid.

In embodiments, the modified amino acid is an acetylated amino acid. Where the modified amino acid is an acetylated amino acid, the non-cell penetrating peptide includes an amino acid residue attached to an acetyl ($-CH_3C(O)$) moiety. In embodiments, the non-cell penetrating peptide is a STAT3 peptide including an acetylated amino acid at a position corresponding to amino acid position 685 of SEQ ID NO:1.

In embodiments, the modified amino acid is a phosphorylated amino acid. Where the modified amino acid is a phosphorylated amino acid, the non-cell penetrating peptide includes an amino acid residue attached to a phosphoryl ($-PO_3$) moiety. In embodiments, the non-cell penetrating peptide is a gp130 peptide including a phosphorylated amino acid at a position corresponding to amino acid position 767 of SEQ ID NO:2. In embodiments, the non-cell penetrating peptide is a gp130 peptide including a phosphorylated amino acid at a position corresponding to amino acid position 905 of SEQ ID NO:2. In embodiments, the non-cell penetrating peptide comprises a gp130 peptide including a phosphorylated amino acid at a position corresponding to amino acid position 915 of SEQ ID NO:2.

The non-cell penetrating peptides provided herein including embodiments thereof are useful for the treatment of cancer, inflammatory disease, pain, and/or viral infection by modifying the activity of intracellular molecules. Thus, in embodiments, the non-cell penetrating peptide binds an intracellular target. In embodiments, the intracellular target is a signaling molecule or transcription factor. In embodiments, the intracellular target is a signaling molecule. In embodiments, the signaling molecule is a phosphatase or kinase. In embodiments, the signaling molecule is a phosphatase. In embodiments, the signaling molecule is a kinase.

In embodiments, the intracellular target is a karyopherin. In embodiments, the karyopherin is an exportin. In embodiments, the intracellular target is exportin 7. In embodiments, the intracellular target is an exportin 7 protein including the amino acid sequence of SEQ ID NO:5. In embodiments, the intracellular target is the amino acid sequence of SEQ ID NO:5. In embodiments, the intracellular target is the amino acid sequence of SEQ ID NO:11.

In embodiments, the non-cell penetrating peptide is a STAT3 peptide. In embodiments, the non-cell penetrating peptide is an acetylated STAT3 peptide. In embodiments, the non-cell penetrating peptide includes the sequence of SEQ ID NO:3. In embodiments, the non-cell penetrating peptide is the sequence of SEQ ID NO:3.

In embodiments, the intracellular target is a transcription factor. In embodiments, the intracellular target is STAT3. In embodiments, the intracellular target is a STAT3 protein including the amino acid sequence of SEQ ID NO:1. In embodiments, the intracellular target is the amino acid sequence of SEQ ID NO:1.

In embodiments, the non-cell penetrating peptide is a gp130 peptide. The term "gp130" or "gp130 protein" as used herein refers to any of the recombinant or naturally-occurring forms of the glycoprotein 130 (gp130) or variants or homologs thereof that maintain gp130 protein activity (e.g. within at least 50%, 80%, 90%, 95%, 96%, 97%, 98%, 99% or 100% activity compared to gp130). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring gp130 polypeptide. In embodiments, the gp130 polypeptide is substantially identical to the protein identified by the UniProt reference number P40189 or a variant or homolog having substantial identity thereto. In embodiments, the gp130 polypeptide includes the sequence of SEQ ID NO:2. In embodiments, the gp130 polypeptide is the sequence of SEQ ID NO:2.

In embodiments, the non-cell penetrating peptide is a phosphorylated gp130 peptide. In embodiments, the non-cell penetrating peptide includes the sequence of SEQ ID NO:4, SEQ ID NO:8 or SEQ ID NO:9. In embodiments, the non-cell penetrating peptide includes the sequence of SEQ ID NO:4. In embodiments, the non-cell penetrating peptide is the sequence of SEQ ID NO:4. In embodiments, the non-cell penetrating peptide includes the sequence of SEQ ID NO:8. In embodiments, the non-cell penetrating peptide is the sequence of SEQ ID NO:8. In embodiments, the non-cell penetrating peptide includes the sequence of SEQ ID NO:9. In embodiments, the non-cell penetrating peptide is the sequence of SEQ ID NO:9.

In embodiments, the non-cell penetrating peptide is a c-MYC binding peptide. A "c-MYC binding peptide" provided herein refers to a peptide capable of binding, covalently or non-covalently, to a c-MYC protein. The terms "c-MYC" or "c-MYC protein" as used herein refer to any of the recombinant or naturally-occurring forms of the c-MYC protein or variants or homologs thereof that maintain c-MYC protein activity (e.g. within at least 50%, 80%, 90%, 95%, 96%, 97%, 98%, 99% or 100% activity compared to c-MYC). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring c-MYC polypeptide. In embodiments, the c-MYC protein is substantially identical to the protein identified by the Uni- Prot reference number P01106 or a variant or homolog having substantial identity thereto. In embodiments, the c-MYC protein includes the sequence of SEQ ID NO:11. In embodiments, the c-MYC protein is the sequence of SEQ ID NO:11.

In embodiments, the non-cell penetrating peptide competes with a cellular protein or cellular peptide for binding an intracellular target. A "cellular protein or cellular peptide" refers to a protein or peptide that is endogenous to a cell (i.e., is native to, or originates within, a given cell). In embodiments, the cellular protein or cellular peptide includes the sequence of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10 or SEQ ID NO:12. In embodiments, the cellular protein or cellular peptide includes the sequence of SEQ ID NO:1. In embodiments, the cellular protein or cellular peptide includes the sequence of SEQ ID NO:2. In embodiments, the cellular protein or cellular peptide includes the sequence of SEQ ID NO:3. In embodiments, the cellular protein or cellular peptide includes the sequence of SEQ ID NO:4. In embodiments, the cellular protein or cellular peptide includes the sequence of SEQ ID NO:6. In embodiments, the cellular protein or cellular peptide includes the sequence of SEQ ID NO:7. In embodiments, the cellular protein or cellular peptide includes the sequence of SEQ ID NO:8. In embodiments, the cellular protein or cellular peptide includes the sequence of SEQ ID NO:9. In embodiments, the cellular protein or cellular peptide includes the sequence of SEQ ID NO:10. In embodiments, the cellular protein or cellular peptide includes the sequence of SEQ ID NO:12. In embodiments, the cellular protein or cellular peptide is the sequence of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10 or SEQ ID NO:12. In embodiments, the cellular protein or cellular peptide is the sequence of SEQ ID NO:1. In embodiments, the cellular protein or cellular peptide is the sequence of SEQ ID NO:2. In embodiments, the cellular protein or cellular peptide is the sequence of SEQ ID NO:3. In embodiments, the cellular protein or cellular peptide is the sequence of SEQ ID NO:4. In embodiments, the cellular protein or cellular peptide is the sequence of SEQ ID NO:6. In embodiments, the cellular protein or cellular peptide is the sequence of SEQ ID NO:7. In embodiments, the cellular protein or cellular peptide is the sequence of SEQ ID NO:8. In embodiments, the cellular protein or cellular peptide is the sequence of SEQ ID NO:9. In embodiments, the cellular protein or cellular peptide is the sequence of SEQ ID NO:10. In embodiments, the cellular protein or cellular peptide is the sequence of SEQ ID NO:12.

In embodiments, the cellular protein or cellular peptide is a STAT3 protein or fragment thereof. In embodiments, the cellular protein or cellular peptide is a gp130 protein or fragment thereof. In embodiments, the cellular protein or cellular peptide is a MAX protein or fragment thereof.

In embodiments, the phosphorothioate nucleic acid is about 10, 20, 30, 40, 50, 60, 70, 80, 90, 100 or more nucleic acid residues in length. In embodiments, the phosphorothioate nucleic acid is about 10 nucleic acid residues in length. In embodiments, the phosphorothioate nucleic acid is about 20 nucleic acid residues in length. In embodiments, the phosphorothioate nucleic acid is about 30 nucleic acid residues in length. In embodiments, the phosphorothioate nucleic acid is about 40 nucleic acid residues in length. In embodiments, the phosphorothioate nucleic acid is about 50 nucleic acid residues in length. In embodiments, the phosphorothioate nucleic acid is about 60 nucleic acid residues in length. In embodiments, the phosphorothioate nucleic acid is about 70 nucleic acid residues in length. In embodiments, the phosphorothioate nucleic acid is about 80 nucleic acid residues in length. In embodiments, the phosphorothioate nucleic acid is about 90 nucleic acid residues in length. In embodiments, the phosphorothioate nucleic acid is about 100 nucleic acid residues in length. In embodiments, the phosphorothioate nucleic acid is about more than 100 nucleic acid residues in length. In embodiments, the phosphorothioate nucleic acid is 10, 20, 30, 40, 50, 60, 70, 80, 90, 100 or more nucleic acid residues in length.

In embodiments, the phosphorothioate nucleic acid is from about 10 to about 30 nucleic acid residues in length. In embodiments, the phosphorothioate nucleic acid is from about 11 to about 30 nucleic acid residues in length. In embodiments, the phosphorothioate nucleic acid is from about 12 to about 30 nucleic acid residues in length. In embodiments, the phosphorothioate nucleic acid is from about 13 to about 30 nucleic acid residues in length. In embodiments, the phosphorothioate nucleic acid is from about 14 to about 30 nucleic acid residues in length. In embodiments, the phosphorothioate nucleic acid is from about 15 to about 30 nucleic acid residues in length. In embodiments, the phosphorothioate nucleic acid is from about 16 to about 30 nucleic acid residues in length. In embodiments, the phosphorothioate nucleic acid is from about 17 to about 30 nucleic acid residues in length. In embodiments, the phosphorothioate nucleic acid is from about 18 to about 30 nucleic acid residues in length. In embodiments, the phosphorothioate nucleic acid is from about 19 to about 30 nucleic acid residues in length. In embodiments, the phosphorothioate nucleic acid is from about 20 to about 30 nucleic acid residues in length. In embodiments, the phosphorothioate nucleic acid is from about 21 to about 30 nucleic acid residues in length. In embodiments, the phosphorothioate nucleic acid is from about 22 to about 30 nucleic acid residues in length. In embodiments, the phosphorothioate nucleic acid is from about 23 to about 30 nucleic acid residues in length. In embodiments, the phosphorothioate nucleic acid is from about 24 to about 30 nucleic acid residues in length. In embodiments, the phosphorothioate nucleic acid is from about 25 to about 30 nucleic acid residues in length. In embodiments, the phosphorothioate nucleic acid is from about 26 to about 30 nucleic acid residues in length. In embodiments, the phosphorothioate nucleic acid is from about 27 to about 30 nucleic acid residues in length. In embodiments, the phosphorothioate nucleic acid is from about 28 to about 30 nucleic acid residues in length. In embodiments, the phosphorothioate nucleic acid is from about 29 to about 30 nucleic acid residues in length. In embodiments, the phosphorothioate nucleic acid is about 30 nucleic acid residues in length.

In embodiments, the phosphorothioate nucleic acid is from about 10 to about 29 nucleic acid residues in length. In embodiments, the phosphorothioate nucleic acid is from about 10 to about 28 nucleic acid residues in length. In embodiments, the phosphorothioate nucleic acid is from about 10 to about 27 nucleic acid residues in length. In embodiments, the phosphorothioate nucleic acid is from about 10 to about 26 nucleic acid residues in length. In embodiments, the phosphorothioate nucleic acid is from about 10 to about 25 nucleic acid residues in length. In embodiments, the phosphorothioate nucleic acid is from about 10 to about 24 nucleic acid residues in length. In embodiments, the phosphorothioate nucleic acid is from about 10 to about 23 nucleic acid residues in length. In embodiments, the phosphorothioate nucleic acid is from about 10 to about 22 nucleic acid residues in length. In embodiments, the phosphorothioate nucleic acid is from about 10 to about 21 nucleic acid residues in length. In embodiments, the phosphorothioate nucleic acid is from about 10 to about 20 nucleic acid residues in length. In embodiments, the phosphorothioate nucleic acid is from about 10 to about 19 nucleic acid residues in length. In embodiments, the phosphorothioate nucleic acid is from about 10 to about 18 nucleic acid residues in length. In embodiments, the phosphorothioate nucleic acid is from about 10 to about 17 nucleic acid residues in length. In embodiments, the phosphorothioate nucleic acid is from about 10 to about 16 nucleic acid residues in length. In embodiments, the phosphorothioate nucleic acid is from about 10 to about 15 nucleic acid residues in length. In embodiments, the phosphorothioate nucleic acid is from about 10 to about 14 nucleic acid residues in length. In embodiments, the phosphorothioate nucleic acid is from about 10 to about 13 nucleic acid residues in length. In embodiments, the phosphorothioate nucleic acid is from about 10 to about 12 nucleic acid residues in length. In embodiments, the phosphorothioate nucleic acid is from about 10 to about 11 nucleic acid residues in length. In embodiments, the phosphorothioate nucleic acid is about 10 nucleic acid residues in length. In embodiments, the phosphorothioate nucleic acid is 10, 11, 12, 13, 14, 15, 16, 17, 18, 19, 20, 21, 22, 23, 24, 25, 26, 27, 28, 29, or 30 nucleic acid residues in length.

In embodiments, the phosphorothioate nucleic acid is about 20 nucleic acid residues in length. In embodiments, the phosphorothioate nucleic acid is 20 nucleic acid residues in length.

In embodiments, the phosphorothioate nucleic acid is a single stranded nucleic acid. In embodiments, the phosphorothioate nucleic acid is a phosphorothioate deoxyribonucleic acid.

In embodiments, the chemical linker is a covalent linker. In embodiments, the linker includes the structure of formula:

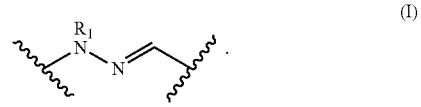

(I)

In formula (I), $R^1$ is hydrogen, halogen, —CF$_3$, —CN, —CCl$_3$, —COOH, —CH$_2$COOH, —CONH$_2$, —OH, —SH, —NO$_2$, —NH$_2$, —NHNH$_2$, —ONH$_2$, —NHC=(O)NHNH$_2$, substituted (e.g., substituted with substituent group(s), size-limited substituent group(s), or lower substituent group(s)) or unsubstituted alkyl, substituted (e.g., substituted with substituent group(s), size-limited substituent group(s), or lower substituent group(s)) or unsubstituted heteroalkyl, substituted (e.g., substituted with substituent group(s), size-limited substituent group(s), or lower substituent group(s)) or unsubstituted cycloalkyl, substituted (e.g., substituted with substituent group(s), size-limited substituent group(s), or lower substituent group(s)) or unsubstituted heterocycloalkyl, substituted (e.g., substituted with substituent group(s), size-limited substituent group(s), or lower substituent group(s)) or unsubstituted aryl, or substituted (e.g., substituted with substituent group(s), size-limited substituent group(s), or lower substituent group(s)) or unsubstituted heteroaryl.

In embodiments, $R^1$ is hydrogen, halogen, —$CF_3$, —CN, —$CCl_3$, —COOH, —$CH_2$COOH, —$CONH_2$, —OH, —SH, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the linker is -$L^1$-$L^2$-$L^3$-$L^4$-$L^5$-$L^6$-$L^7$-. In embodiments, $L^1$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^2$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^3$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^4$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^5$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^6$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^7$ is a bond, —NH—N=CH—, —$S(O)_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s))

or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, the linker is a non-immunogenic linker. In embodiments, the linker is substituted with a detectable moiety.

In embodiments, the conjugate includes a detectable moiety. In embodiments, the detectable moiety is attached to the non-cell penetrating peptide. In embodiments, the detectable moiety is attached to the phosphorothioate nucleic acid. In embodiments, the detectable moiety forms part of the linker. In embodiments, the detectable moiety is covalently attached to the linker.

In embodiments, the conjugate as provided herein including embodiments thereof is bound to an intracellular target.

In an aspect is provided a cell including a peptide conjugate as described herein including embodiments thereof.

In one embodiment, the non-cell penetrating peptide is a peptide of SEQ ID NO:3, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:6, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:7, the phosphorthioate nucleic acid is a single stranded nucleic acid 20 nucleic acid residues in length and the chemical linker includes the structure of formula (I).

In one embodiment, the non-cell penetrating peptide is an acetylated peptide of SEQ ID NO:3, the phosphorthioate nucleic acid is a single stranded nucleic acid 20 nucleic acid residues in length and the chemical linker includes the structure of formula (I).

In one embodiment, the non-cell penetrating peptide is an acetylated peptide of SEQ ID NO:6, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:4, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:8, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:9, the phosphorthioate nucleic acid is a single stranded nucleic acid 20 nucleic acid residues in length and the chemical linker includes the structure of formula (I).

In one embodiment, the non-cell penetrating peptide is a phosphorylated peptide of SEQ ID NO:4, the phosphorthioate nucleic acid is a single stranded nucleic acid 20 nucleic acid residues in length and the chemical linker includes the structure of formula (I).

In one embodiment, the non-cell penetrating peptide is a phosphorylated peptide of SEQ ID NO:8, the phosphorthioate nucleic acid is a single stranded nucleic acid 20 nucleic acid residues in length and the chemical linker includes the structure of formula (I).

In one embodiment, the non-cell penetrating peptide is a phosphorylated peptide of SEQ ID NO:9, the phosphorthioate nucleic acid is a single stranded nucleic acid 20 nucleic acid residues in length and the chemical linker includes the structure of formula (I).

In one embodiment, the non-cell penetrating peptide is a peptide of SEQ ID NO:10, the phosphorthioate nucleic acid is a single stranded nucleic acid 20 nucleic acid residues in length and the chemical linker includes the structure of formula (I).

Dimer Compositions

The nucleic acid-peptide conjugates provided herein including embodiments thereof may be non-covalently bound (e.g., through hybridization) to a second nucleic acid-peptide conjugate. Thus, in embodiments the nucleic acid-peptide conjugate forms a conjugate dimer with a second nucleic acid-peptide conjugate. The second nucleic acid-peptide conjugate includes (1) a second non-cell penetrating peptide, (2) a non-phosphorothioated nucleic acid hybridized to the phosphorothioate nucleic acid and (3) a second chemical linker attaching the complementary non-phosphorothioated nucleic acid to the C-terminus of the second non-cell penetrating peptide.

In one aspect, a conjugate dimer is provided. The conjugate dimer includes:
(i) a first nucleic acid-peptide conjugate including:
 (a) a first non-cell penetrating peptide;
 (b) a phosphorothioate nucleic acid; and
 (c) a first chemical linker attaching said phosphorothioate nucleic acid to the C-terminus of the first non-cell penetrating peptide;
(ii) a second nucleic acid-peptide conjugate including:
 (a) a second non-cell penetrating peptide;
 (b) a non-phosphorothioated nucleic acid; and
 (c) a second chemical linker attaching the non-phosphorothioated nucleic acid to the C-terminus of the second non-cell penetrating peptide;
  wherein the phosphorothioate nucleic acid and the non-phosphorothioated nucleic acid are hybridized to bind said first nucleic acid-peptide conjugate to said second nucleic acid-peptide conjugate thereby forming a conjugate dimer.

The first nucleic acid-peptide conjugate and the second nucleic acid-peptide conjugate may be any one of the nucleic acid-peptide conjugates described herein including embodiments thereof. Thus, the first non-cell penetrating peptide and the second non-cell penetrating peptide may be any one of the non-cell penetrating peptides provide herein including embodiments thereof (e.g., a peptide of SEQ ID NO:3. SEQ ID NO:4, SEQ ID NO:6, SEQ ID NO:7, SEQ ID NO:8, SEQ ID NO:9, or SEQ ID NO:10). Likewise, the first chemical linker and the second chemical linker may be any of the chemical linker described herein including embodiments thereof (e.g., a chemical linker of formula (I)). The first non-cell penetrating peptide and the second non-cell penetrating peptide may be chemically identical or different. The phosphorothioate nucleic acid may be any one of the phosphorothioate nucleic acids provided herein including embodiments thereof (e.g., having a length of 20 nucleic acid residues). A "non-phosphorothioated nucleic acid" as provided herein is a nucleic acid that does not include a phosphorothioate nucleotide. Non-phosphorothioated nucleic acids provided herein may be from about 5, 6, 7, 8, 9, 10, 12, 15, 25, 30, 40, 50 or more nucleotides in length, up to about 100 nucleotides in length. Non-phosphorothioated nucleic acids may also be longer in lengths, e.g., 200, 300, 500, 1000, 2000, 3000, 5000, 7000, 10,000, etc.

In embodiments, the first non-cell penetrating peptide has the sequence of SEQ ID NO:3 and the second non-cell penetrating peptide has the sequence of SEQ ID NO:3. In embodiments, the conjugate dimer is a dimer as shown in FIG. 22A. In embodiments, the conjugate dimer is a dimer as shown in FIG. 24A.

Like conjugate compositions provided herein, the conjugate dimers provided herein including embodiments thereof may form part of pharmaceutical compositions provided herein and may be used for any of the methods described herein.

Pharmaceutical Compositions

The conjugates provided herein including embodiments thereof are further contemplated as forming part of a pharmaceutical composition. Therefore, in an aspect is provided a pharmaceutical composition including the peptide conjugate as described herein including embodiments thereof and a pharmaceutically acceptable carrier.

Pharmaceutical compositions provided by the present invention include compositions wherein the active ingredient (e.g. compositions described herein, including embodiments thereof) is contained in a therapeutically effective amount, i.e., in an amount effective to achieve its intended purpose. The actual amount effective for a particular application will depend, inter alia, on the condition being treated. When administered in methods to treat a disease, the conjugates described herein will contain an amount of active ingredient effective to achieve the desired result, e.g., modulating the activity of a target molecule, and/or reducing, eliminating, or slowing the progression of disease symptoms. Determination of a therapeutically effective amount of a conjugate of the invention is within the capabilities of those skilled in the art.

The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the conjugates provided herein including embodiments thereof) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Methods of Treating Cancer

The conjugates as provided herein including embodiments thereof are useful, inter alia, for the treatment of cancer. Thus, in an aspect, a method for treating cancer in a subject in need thereof is provided. The method includes administering to the subject a therapeutically effective amount of a cell penetrating peptide conjugate as described herein including embodiments thereof, thereby treating the cancer in the subject.

In embodiments, the cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma. In embodiments, the cancer is metastatic lung cancer.

In embodiments, the method further includes administering an effective amount of a second therapeutic agent to the subject.

Suitable additional therapeutic agents include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

In embodiments, the second therapeutic agent is a nucleic acid-peptide conjugate as provided herein. Therefore, a first nucleic acid-peptide conjugate and a second nucleic acid-peptide conjugate may be administered and the first and second nucleic acid-peptide conjugate are independently a nucleic acid-peptide conjugate as provided herein including embodiments thereof. The first nucleic acid-peptide conjugate and the second nucleic acid-peptide conjugate may be chemically different or the same. For example, the first nucleic acid-peptide conjugate may include a first non-cell penetrating peptide, wherein the first non-cell penetrating peptide is a STAT3 peptide provided herein including embodiments thereof, and the second nucleic acid-peptide conjugate may include a second non-cell penetrating peptide, wherein the second non-cell penetrating peptide may be a gp130 peptide provided herein including embodiments thereof. In other embodiments, the first nucleic acid-peptide conjugate includes a first non-cell penetrating peptide, wherein the first non-cell penetrating peptide is a gp130 peptide provided herein including embodiments thereof, and the second nucleic acid-peptide conjugate includes a second non-cell penetrating peptide, wherein the second non-cell penetrating peptide is a c-MYC binding peptide provided herein including embodiments thereof.

Thus, in embodiments, the second therapeutic agent is a second nucleic acid-peptide conjugate. In embodiments, the second nucleic acid-peptide conjugate includes a second non-cell penetrating peptide. In embodiments, the second non-cell penetrating peptide is a STAT3 peptide. In embodiments, the second non-cell penetrating peptide is an acetylated STAT3 peptide. In embodiments, the second non-cell penetrating peptide includes the sequence of SEQ ID NO:3, SEQ ID NO:6 or SEQ ID NO:7. In embodiments, second non-cell penetrating peptide includes the sequence of SEQ ID NO:3. In embodiments, the second non-cell penetrating peptide is the sequence of SEQ ID NO:3. In embodiments, the second non-cell penetrating peptide includes the sequence of SEQ ID NO:6. In embodiments, the second non-cell penetrating peptide is the sequence of SEQ ID NO:6. In embodiments, the second non-cell penetrating peptide includes the sequence of SEQ ID NO:7. In embodiments, the second non-cell penetrating peptide is the sequence of SEQ ID NO:7.

In embodiments, the second non-cell penetrating peptide is a gp130 peptide. In embodiments, the second non-cell penetrating peptide includes the sequence of SEQ ID NO:4. In embodiments, the second non-cell penetrating peptide is the sequence of SEQ ID NO:4.

In embodiments, the second non-cell penetrating peptide is a phosphorylated gp130 peptide. In embodiments, the second non-cell penetrating peptide includes the sequence of SEQ ID NO:4, SEQ ID NO:8 or SEQ ID NO:9. In embodiments, the second non-cell penetrating peptide includes the sequence of SEQ ID NO:4. In embodiments, the second non-cell penetrating peptide is the sequence of SEQ ID NO:4. In embodiments, the second non-cell penetrating peptide includes the sequence of SEQ ID NO:8. In embodiments, the second non-cell penetrating peptide is the sequence of SEQ ID NO:8. In embodiments, the second non-cell penetrating peptide includes the sequence of SEQ ID NO:9. In embodiments, the second non-cell penetrating peptide is the sequence of SEQ ID NO:9.

In embodiments, the second non-cell penetrating peptide is a c-MYC binding peptide. In embodiments, the second non-cell penetrating peptide includes the sequence of SEQ ID NO:10. In embodiments, the second non-cell penetrating peptide is the sequence of SEQ ID NO:10.

In embodiments, the second non-cell penetrating peptide is a STAT3 peptide including an acetylated amino acid at a position corresponding to amino acid position 685 of SEQ ID NO:1.

In embodiments, the second non-cell penetrating peptide is a gp130 peptide including a phosphorylated amino acid at a position corresponding to amino acid position 767 of SEQ ID NO:2. In embodiments, the second non-cell penetrating peptide is a gp130 peptide including a phosphorylated amino acid at a position corresponding to amino acid position 905 of SEQ ID NO:2. In embodiments, the second non-cell penetrating peptide is a gp130 peptide including a phosphorylated amino acid at a position corresponding to amino acid position 915 of SEQ ID NO:2.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

In embodiments, the method includes decreasing in the subject an expression level of BIRC5 or BclXL or PD-L1 relative to a standard control. In embodiments, the method includes decreasing in the subject an expression level of BIRC5 relative to a standard control. In embodiments, the method includes decreasing in the subject an expression level of BclXL relative to a standard control. In embodiments, the standard control is an expression level of BIRC5 or BclXL detected in the absence of a cell penetrating peptide conjugate as described herein including embodiments thereof.

The term "BIRC5," also known as "survivin", as referred to herein includes any of the recombinant or naturally-occurring forms of the gene encoding baculoviral inhibitor of apoptosis repeat-containing 5 (BIRC5), homologs or variants thereof that maintain BIRC5 activity (e.g. within at least 50%, 80%, 90%, 95%, 96%, 97%, 98%, 99% or 100% activity compared to BIRC5). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BIRC5 polypeptide. In embodiments, the BIRC5 gene is substantially identical to the nucleic acid identified by the ENSEMBLE reference number ENSG00000089685 or a variant having substantial identity thereto. The expression level of BRICS may be determined by detecting levels of BIRC5 mRNA or protein using methods known in the art. In embodiments, the BIRC5 mRNA is the nucleic acid sequence as identified by the Ensembl ID: ENST00000301633.8, homolog or functional fragment thereof. In embodiments, the BIRC5 protein is the amino acid sequence as identified by Uniprot reference number 015392, homolog or functional fragment thereof.

The term "BclXL," also known as BCL2L1, as referred to herein includes any of the recombinant or naturally-occurring forms of the gene encoding B-cell lymphoma-extra large (BclXL), homologs or variants thereof that maintain BclXL activity (e.g. within at least 50%, 80%, 90%, 95%, 96%, 97%, 98%, 99% or 100% activity compared to BclXL). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BclXL polypeptide. In embodiments, the BclXL gene is substantially identical to the nucleic acid identified by the ENSEMBLE reference number ENSG00000171552 or a variant having substantial identity thereto. The expression level of BclXL may be determined by detecting levels of BclXL mRNA or protein using methods known in the art. In embodiments, the BclXL mRNA is the nucleic acid sequence as identified by the Ensembl ID: ENST00000307677.4, homolog or functional fragment thereof. In embodiments, the BclXL protein is the amino acid sequence as identified by Uniprot reference number Q07817, homolog or functional fragment thereof.

The term "PD-L1," also known as CD274 or B7-H1, as referred to herein includes any of the recombinant or naturally-occurring forms of the gene encoding Programmed cell death 1 ligand 1 (PD-L1), homologs or variants thereof that maintain PD-L1 activity (e.g. within at least 50%, 80%, 90%, 95%, 96%, 97%, 98%, 99% or 100% activity compared to PD-L1). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 polypeptide. In embodiments, the PD-L1 gene is substantially identical to the nucleic acid identified by the ENSEMBLE reference number ENSG00000120217 or a variant having substantial identity thereto. The expression level of PD-L1 may be determined by detecting levels of PD-L1 mRNA or protein using methods known in the art. In embodiments, the PD-mRNA is the nucleic acid sequence as identified by the Ensembl ID: ENSG00000120217, homolog or functional fragment thereof. In embodiments, the PD-L1 protein is the amino acid sequence as identified by Uniprot reference number Q9NZQ7, homolog or functional fragment thereof.

Methods of Increasing P53 in a Cell

The conjugates provided herein including embodiments thereof are further contemplated as a means of increasing p53 in a cell. "p53 protein" or "p53" as referred to herein includes any of the recombinant or naturally-occurring forms of the tumor protein p53 (p53) or variants or homologs thereof that maintain p53 activity (e.g. within at least 50%, 80%, 90%, 95%, 96%, 97%, 98%, 99% or 100% activity compared top 53). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring p53 protein. In embodiments, the p53 protein is substantially identical to the protein identified by the UniProt reference number P04637 or a variant or homolog having substantial identity thereto.

In an aspect, a method of increasing expression of p53 in a cancer cell is provided, the method including contacting a cancer cell with an effective amount of a cell penetrating peptide conjugate as described herein including embodiments thereof, thereby increasing expression of p53 in the cancer cell.

Methods of Inhibiting Tumor Vascularization

The conjugates provided herein including embodiments thereof are useful for the treatment of cancer through inhibition of tumor vascularization. Thus, in another aspect, a method of inhibiting tumor vascularization in a subject in need thereof is provided, the method including administering to the subject a therapeutically effective amount of a cell penetrating peptide conjugate as described herein including embodiments thereof, thereby inhibiting tumor vascularization in the subject.

Methods of Treating an Inflammatory Disease

The conjugates provided herein including embodiments thereof are also useful for the treatment of inflammatory disease. Therefore, in another aspect, a method of treating an inflammatory disease in a subject in need thereof is provided, the method including administering to the subject a therapeutically effective amount of a cell penetrating peptide conjugate as described herein including embodiments thereof, thereby treating an inflammatory disease in the subject.

As used herein, the term "inflammatory disease" refers to a disease or condition characterized by aberrant inflammation (e.g., an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In embodiments, the method includes decreasing in the subject an expression level of FGA, IL1B or SERPINA3 relative to a standard control. In embodiments, the method includes decreasing in the subject an expression level of FGA relative to a standard control. In embodiments, the method includes decreasing in the subject an expression level of IL1B relative to a standard control. In embodiments, the method includes decreasing in the subject an expression level of SERPINA3 relative to a standard control. In embodiments, the standard control is an expression level of FGA, IL1B or SERPINA3 detected in the absence of a cell penetrating peptide conjugate as described herein including embodiments thereof.

The term "FGA" as referred to herein includes any of the recombinant or naturally-occurring forms of the gene encoding fibrinogens alpha chain (FGA), homologs or variants thereof that maintain FGA activity (e.g. within at least 50%, 80%, 90%, 95%, 96%, 97%, 98%, 99% or 100% activity compared to FGA). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FGA polypeptide. In embodiments, the FGA gene is substantially identical to the nucleic acid identified by the ENSEMBLE reference number ENSG00000171560 or a variant having substantial identity thereto. The expression level of FGA may be determined by detecting levels of FGA mRNA or protein using methods known in the art. In embodiments, the FGA mRNA is the nucleic acid sequence as identified by the Ensembl ID: ENST00000302053.7, homolog or functional fragment thereof. In embodiments, the FGA protein is the amino acid sequence as identified by Uniprot reference number P02671, homolog or functional fragment thereof.

The term "IL1B" as referred to herein includes any of the recombinant or naturally-occurring forms of the gene encoding interleukin 1 beta (IL1B), homologs or variants thereof that maintain IL1B activity (e.g. within at least 50%, 80%, 90%, 95%, 96%, 97%, 98%, 99% or 100% activity compared to IL1B). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL1B polypeptide. In embodiments, the IL1B gene is substantially identical to the nucleic acid identified by the ENSEMBLE reference number ENSG00000125538 or a variant having substantial identity thereto. The expression level of IL1B may be determined by detecting levels of IL1B mRNA or protein using methods known in the art. In embodiments, the IL1B mRNA is the nucleic acid sequence as identified by the Ensembl ID: ENST00000263341.6, homolog or functional fragment thereof. In embodiments, the IL1B protein is the amino acid sequence as identified by Uniprot reference number P01584, homolog or functional fragment thereof.

The term "SERPINA3" as referred to herein includes any of the recombinant or naturally-occurring forms of the gene encoding alpha 1-antichymotrypsin, homologs or variants thereof that maintain alpha 1-antichymotrypsin activity (e.g. within at least 50%, 80%, 90%, 95%, 96%, 97%, 98%, 99% or 100% activity compared to alpha 1-antichymotrypsin). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring alpha 1-antichymotrypsin polypeptide. In embodiments, the SERPINA3 gene is substantially identical to the nucleic acid identified by the ENSEMBLE reference number ENSG00000196136 or a variant having substantial identity thereto. The expression level of SERPINA3 may be determined by detecting levels of SERPINA3 mRNA or protein using methods known in the art. In embodiments, the SERPINA mRNA is the nucleic acid sequence as identified by the Ensembl ID: ENST00000467132.5, homolog or functional fragment thereof. In embodiments, the alpha 1-antichymotrypsin protein is the amino acid sequence as identified by Uniprot reference number P01011, homolog or functional fragment thereof.

Non-Opioid-Based Methods of Treating Pain

Opioids are a class of compound among the most widely used for treatment of pain. Opioid drugs produce effects by interacting with opioid receptors. Opioids have opium- or morphine-like properties allowing them to act as opioid receptor agonists. However, opioids have other pharmacological effects including drowsiness, respiratory depression, and constipation, as well as abuse potential and tolerance. The negative side-effects of opioid use have spurred a need for non-opioid-based pain treatments. Provided herein are, inter alia, non-opioid-based methods for treating pain in a subject in need thereof.

In an aspect, a method of treating pain in a subject in need thereof is provided. The method includes administering to the subject a therapeutically effective amount of a cell penetrating peptide conjugate as described herein including embodiments thereof, thereby treating pain in the subject.

The pain may emanate from a wide variety of sources or be derived from a wide variety of causes. Thus, the pain may be nociceptive pain (e.g., trauma, procedural, cut, sprains, bone fractures, burns, bumps, bruises), neuropathic pain (e.g., post herpetic neuralgia, reflex sympathetic dystrophy/causalgia, cancer pain, pain induced by treatment of cancer, HIV/AIDS or hepatitis, diabetes, phantom limb pain, entrapment neuropathy, chronic alcohol use, exposure to other toxins, vitamin deficiencies and idiopathic), inflammatory pain (e.g., arthritis, colitis, carditis, pulmonits, nephritis, myositis, vasculitis, endometriosis, neuritis, dermatitis and pain associated with other inflammatory conditions), chronic widespread pain (e.g., fibromyalgia, migraine, irritable bowel syndrome, syndrome X, interstitial bladder syndrome, chronic fatigue syndrome, post-traumatic stress disorder, pain associated with psychiatric illnesses such as anxiety and depression and stress-related pain conditions, and secondary to inflammatory or neuropathic pain syndromes) or mixed etiology (i.e., combinations of two or more of the above four categories).

In embodiments, the peptide conjugates useful for treating pain in the methods provided herein does not mediate its analgesic effect through opioid receptors. In embodiments, the peptide conjugate useful for treating pain in the methods provided herein does not have opium- or morphine-like properties. In embodiments, the peptide conjugate useful for treating pain in the methods provided herein is not an opioid receptor ligand. In embodiments, the peptide conjugate useful for treating pain in the methods provided herein does not bind to an opioid receptor. In embodiments, the peptide conjugate useful for treating pain in the methods provided herein is not an opioid receptor agonist.

In embodiments, the method includes decreasing in the subject an expression level of PTGS1, PTGS2, CALCA or SST relative to a standard control. In embodiments, the method includes decreasing in the subject an expression level of PTG51 relative to a standard control. In embodiments, the method includes decreasing in the subject an expression level of PTG52 relative to a standard control. In embodiments, the method includes decreasing in the subject an expression level of CALCA relative to a standard control. In embodiments, the method includes decreasing in the subject an expression level of SST relative to a standard control. In embodiments, the standard control is an expression level of PTGS1, PTGS2, CALCA or SST detected in the absence of a cell penetrating peptide conjugate as described herein including embodiments thereof.

The term "PTGS1" as referred to herein includes any of the recombinant or naturally-occurring forms of the gene encoding prostaglandin-endoperoxide synthase 1 (PTGS1), also known as COX-1, homologs or variants thereof that maintain PTGS1 activity (e.g. within at least 50%, 80%, 90%, 95%, 96%, 97%, 98%, 99% or 100% activity compared to PTGS1). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PTGS1 polypeptide. In embodiments, the PTGS1 gene is substantially identical to the nucleic acid identified by the ENSEMBLE reference number ENSG00000095303 or a variant having substantial identity thereto. The expression level of PTGS1 may be determined by detecting levels of PTGS1 mRNA or protein using methods known in the art. In embodiments, the PTGS1 mRNA is the nucleic acid sequence as identified by the Ensembl ID: ENST00000540753.5, homolog or functional fragment thereof. In embodiments, the PTGS1 protein is the amino acid sequence as identified by Uniprot reference number P23219, homolog or functional fragment thereof.

The term "PTGS2" as referred to herein includes any of the recombinant or naturally-occurring forms of the gene encoding prostaglandin-endoperoxide synthase 2 (PTGS2), also known as COX-2, homologs or variants thereof that maintain PTGS2 activity (e.g. within at least 50%, 80%, 90%, 95%, 96%, 97%, 98%, 99% or 100% activity compared to PTGS2). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PTGS2 polypeptide. In embodiments, the PTGS2 gene is substantially identical to the nucleic acid identified by the ENSEMBLE reference number ENSG00000073756 or a variant having substantial identity thereto. The expression level of PTGS2 may be determined by detecting levels of PTGS2 mRNA or protein using methods known in the art. In embodiments, the PTGS2 mRNA is the nucleic acid sequence as identified by the Ensembl ID: ENST00000367468.9, homolog or functional fragment thereof. In embodiments, the PTGS2 protein is the amino acid sequence as identified by Uniprot reference number P35354, homolog or functional fragment thereof.

The term "SST" as referred to herein includes any of the recombinant or naturally-occurring forms of the gene encoding somatostatin (SST), homologs or variants thereof that maintain SST activity (e.g. within at least 50%, 80%, 90%, 95%, 96%, 97%, 98%, 99% or 100% activity compared to SST). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SST polypeptide. In embodiments, the SST gene is substantially identical to the nucleic acid identified by the ENSEMBLE reference number ENSG00000157005 or a variant having substantial identity thereto. The expression level of SST may be determined by detecting levels of SST mRNA or protein using methods known in the art. In embodiments, the SST mRNA is the nucleic acid sequence as identified by the Ensembl ID: ENST00000287641.3, homolog or functional fragment thereof. In embodiments, the SST protein is the amino acid sequence as identified by Uniprot reference number P61278, homolog or functional fragment thereof.

The term "CALCA" as referred to herein includes any of the recombinant or naturally-occurring forms of the gene encoding calcitonin gene-related peptide (CGRP), homologs or variants thereof that maintain CALCA activity (e.g. within at least 50%, 80%, 90%, 95%, 96%, 97%, 98%, 99% or 100% activity compared to CALCA). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CALCA polypeptide. In embodiments, the CALCA gene is substantially identical to the nucleic acid identified by the ENSEMBLE reference number ENSG00000110680 or a variant having substantial identity thereto. The expression level of CALCA may be determined by detecting levels of CALCA mRNA or protein using methods known in the art. In embodiments, the CALCA mRNA is the nucleic acid sequence as identified by the Ensembl ID: ENST00000361010.7, homolog or functional fragment thereof. In embodiments, the CALCA protein is the amino acid sequence as identified by Uniprot reference numbers P01258, P06881, homolog or functional fragment thereof.

Methods of Treating Viral Infection and Viral Entry into a Cell

The conjugates provided herein including embodiments thereof are useful for inhibiting viral infection and viral entry into a cell. In an aspect, a method of treating a viral infection in a subject in need thereof is provided. The method includes administering to the subject a therapeutically effective amount of a cell penetrating peptide conjugate as described herein including embodiments thereof, thereby treating the viral infection in the subject.

In embodiments, the method comprising decreasing in the subject an expression level of CXCR4, CCR5 or CD155 relative to a standard control. In embodiments, the method comprising decreasing in the subject an expression level of CXCR4 relative to a standard control. In embodiments, the method comprising decreasing in the subject an expression level of CCR5 relative to a standard control. In embodiments, the method comprising decreasing in the subject an expression level of CD155 relative to a standard control. In embodiments, the standard control is an expression level of CXCR4, CCR5 or CD155 detected in the absence of a cell penetrating peptide conjugate as described herein including embodiments thereof.

The term "CXCR4" as referred to herein includes any of the recombinant or naturally-occurring forms of the gene encoding C-X-C chemokine receptor type 4 (CXCR4), homologs or variants thereof that maintain CXCR4 activity (e.g. within at least 50%, 80%, 90%, 95%, 96%, 97%, 98%, 99% or 100% activity compared to CXCR4). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CXCR4 polypeptide. In embodiments, the CXCR4 gene is substantially identical to the nucleic acid identified by the ENSEMBLE reference number ENSG00000121966 or a variant having substantial identity thereto. The expression level of CXCR4 may be determined by detecting levels of CXCR4 mRNA or protein using methods known in the art. In embodiments, the CXCR4 mRNA is the nucleic acid sequence as identified by the Ensembl ID: ENST00000409817.1, homolog or functional fragment thereof. In embodiments, the CXCR4 protein is the amino acid sequence as identified by Uniprot reference number P61073, homolog or functional fragment thereof.

The term "CCR5" as referred to herein includes any of the recombinant or naturally-occurring forms of the gene encoding C-C motif chemokine receptor 5 (CCR5), homologs or variants thereof that maintain CCR5 activity (e.g. within at least 50%, 80%, 90%, 95%, 96%, 97%, 98%, 99% or 100% activity compared to CCR5). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CCR5 polypeptide. In embodiments, the CCR5 gene is substantially identical to the nucleic acid identified by the ENSEMBLE reference number ENSG00000160791 or a variant having substantial identity thereto. The expression level of CCR5 may be determined by detecting levels of CCR5 mRNA or protein using methods known in the art. In embodiments, the CCR5 mRNA is the nucleic acid sequence as identified by the Ensembl ID: ENST00000292303.4, homolog or functional fragment thereof. In embodiments, the CCR5 protein is the amino acid sequence as identified by Uniprot reference number P51681, homolog or functional fragment thereof.

The term "CD155" as referred to herein includes any of the recombinant or naturally-occurring forms of the gene encoding cluster of differentiation 155 (CD155), also known as poliovirus receptor (PVR), homologs or variants thereof that maintain CD155 activity (e.g. within at least 50%, 80%, 90%, 95%, 96%, 97%, 98%, 99% or 100% activity compared to CD155). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD155 polypeptide. In embodiments, the CD155 gene is substantially identical to the nucleic acid identified by the ENSEMBLE reference number ENSG00000073008 or a variant having substantial identity thereto. The expression level of CD155 may be determined by detecting levels of CD155 mRNA or protein using methods known in the art. In embodiments, the CD155 mRNA is the nucleic acid sequence as identified by the Ensembl ID: ENST00000425690.7, homolog or functional fragment thereof. In embodiments, the CD155 protein is the amino acid sequence as identified by Uniprot reference number P15151, homolog or functional fragment thereof.

In embodiments, the viral infection is an HIV infection or a poliovirus infection.

In an aspect is provided a method of inhibiting viral entry into a cell, the method including contacting a cell with an effective amount of a cell penetrating peptide conjugate as provided herein including embodiments thereof, thereby inhibiting viral entry into the cell.

In embodiments, the method includes decreasing in the cell an expression level of CXCR4, CCR5 or CD155 relative to a standard control. In embodiments, the standard control is an expression level of CXCR4, CCR5 or CD155 detected in the absence of a cell penetrating peptide conjugate as described herein including embodiments thereof.

Methods of Decreasing IL6 Receptor Signaling in a Cell

The conjugates provided herein including embodiments thereof are useful for decreasing IL6 receptor signaling in a cell. Thus, in an aspect, a method of inhibiting IL6 receptor signaling in a cell is provided, the method including contacting a cell with an effective amount of a cell penetrating peptide conjugate as provided herein including embodiments thereof, thereby inhibiting IL6 receptor signaling in the cell.

An "IL6 receptor" as referred to herein includes any of the naturally-occurring forms of the interleukin 6 receptor or variants or homologs thereof that maintain IL6 receptor activity (e.g. within at least 50%, 80%, 90%, 95%, 96%, 97%, 98%, 99% or 100% activity compared to the IL6 receptor). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL6 receptor protein. In embodiments, the IL6 receptor protein is substantially identical to the protein identified by the UniProt reference number P08887 or a variant or homolog having substantial identity thereto.

Methods of Delivering a Non-Cell Penetrating Peptide into a Cell

The conjugates provided herein including embodiments thereof are useful for delivering non-cell penetrating peptides into a cell. In an aspect is provided a method of delivering a non-cell penetrating peptide into a cell, the method including contacting a cell with the cell penetrating peptide conjugate as provided herein including embodiments thereof, thereby delivering the non-cell penetrating peptide into the cell.

EXAMPLES

Applicants initially observed that lysine acetylation of tumor promoting transcription factor STAT3 at lysine K685 is critical to engage STAT3 with the karyopherin exportin 7. Exportin 7, once it recognizes acetylated STAT3, physically interacts with STAT3 and facilitates its nuclear egress and subsequent reactivation at the cell membrane in a dynamic cycle of activation (nuclear import; facilitated by importins)-deactivation (nuclear export; facilitated by exportins)-reactivation (nuclear import).[1] The STAT3 dynamic cycling (nucleocytoplasmic shuttling) is required to maintain persistent STAT3 dependent target gene activation and is therefore considered a promising point of therapeutic interference. Targeting the nucleocytoplasmic shuttling can function to either block the STAT3 activating kinase residing in the cytoplasm or members of karyopherin family (importins, exportins) known to shuttle STAT3 cargo in and out of the cell nucleus. Here, Applicants describe a sequence-specific peptide that competes with STAT3 protein for engagement with exportin 7 and effectively delays tumor growth. Treating human tumors in xenograft model with STAT3 competitor peptide results in gaining expression of tumor suppressor p53 and tumor cell apoptosis indicated by cleaved caspase 3 as well as significantly decreased proliferative activity and tumor blood vessel collapse.

Example 1: Production of Cell Internalizing Peptides Via Covalent Linkage to Phosphorothioated SSDNA Oligonucelotides Peptides either representing stretches of full-length proteins or "man-made" sequences were fused covalently via hydrazide binding to phosphorothioated ssDNA (PS) 20meric oligo to facilitate cellular internalization targeting intracellular molecular targets in an antagonistic or agonistic manner, respectively. A non-phosphorothioated ssDNA oligo (PO) extension of the peptide was employed as a non-internalizing control.

Figure 2:
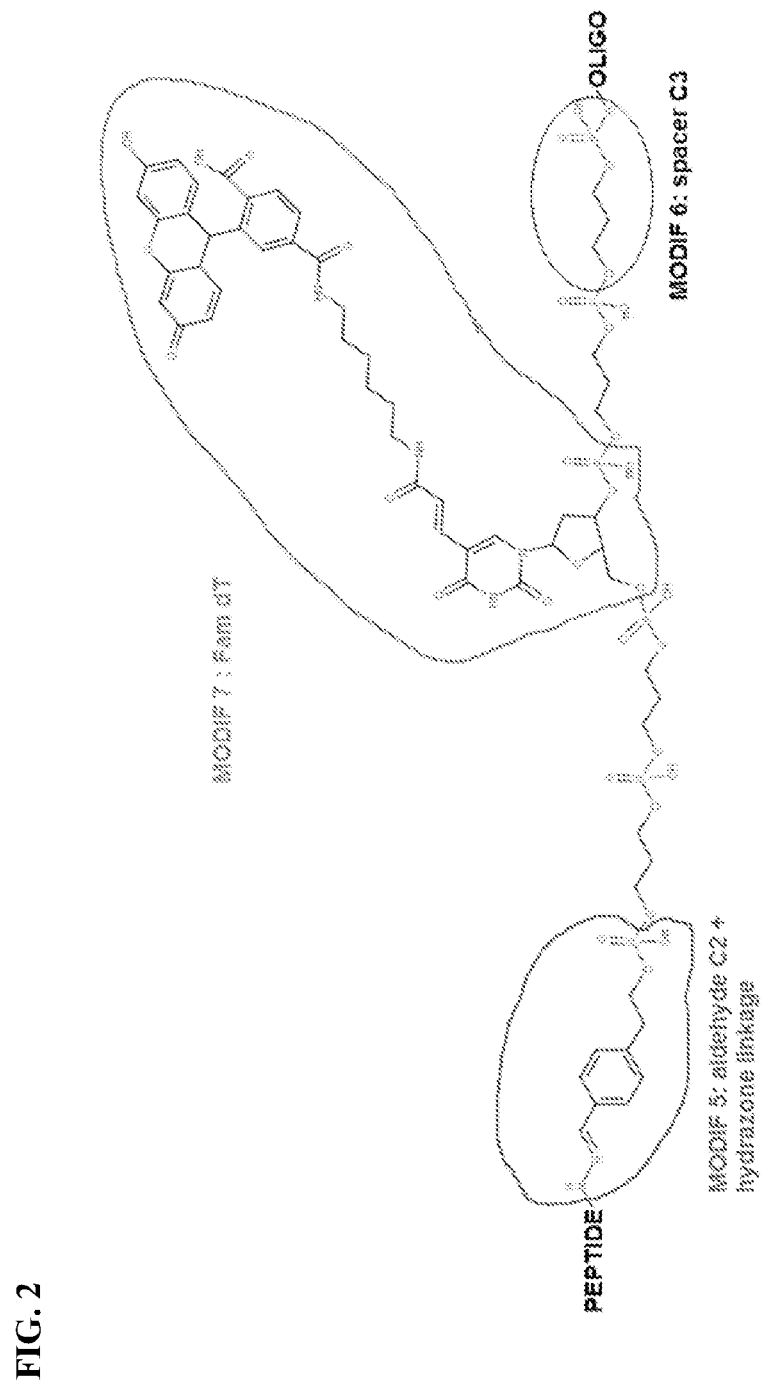
FIG. 2: Scheme of modified peptide sequences (peptide) connected via a Linker (aldehyde C2+hydrazine linkage) and spacers (C3) including a fluorescent tag (Fam dT) to a phosphorothioate ssDNA (oligo).

Applicants modified peptides representing a stretch of amino acids naturally occurring in the human transcription factor STAT3. Applicants chose a region that comprises 22 amino acids, where the lysine K685 undergoes acetylation in tumor cells and in cells participating in inflammatory responses. Applicants designed wildtype (STAT3-wt: PDIPKEEAFGK$_{685}$YCRPESQEHPC; SEQ ID NO:6), mutated (STAT3-K685R: PDIPKEEAFGR$_{685}$YCRPESQEHPC; SEQ ID NO:7), and acetylated (STAT3-acet.K685: PDIPKEEAFG(acet)K$_{685}$YCRPESQEHPC; SEQ ID NO:3) STAT3 peptides (FIG. 5A). The STAT3 peptides were elongated by phosphorothioated ssDNA oligonucleotides (FIG. 1 and FIG. 5A). Peptides were modified by hydrazide driven elongation (FIG. 1 and FIG. 2).

Figure 3A:
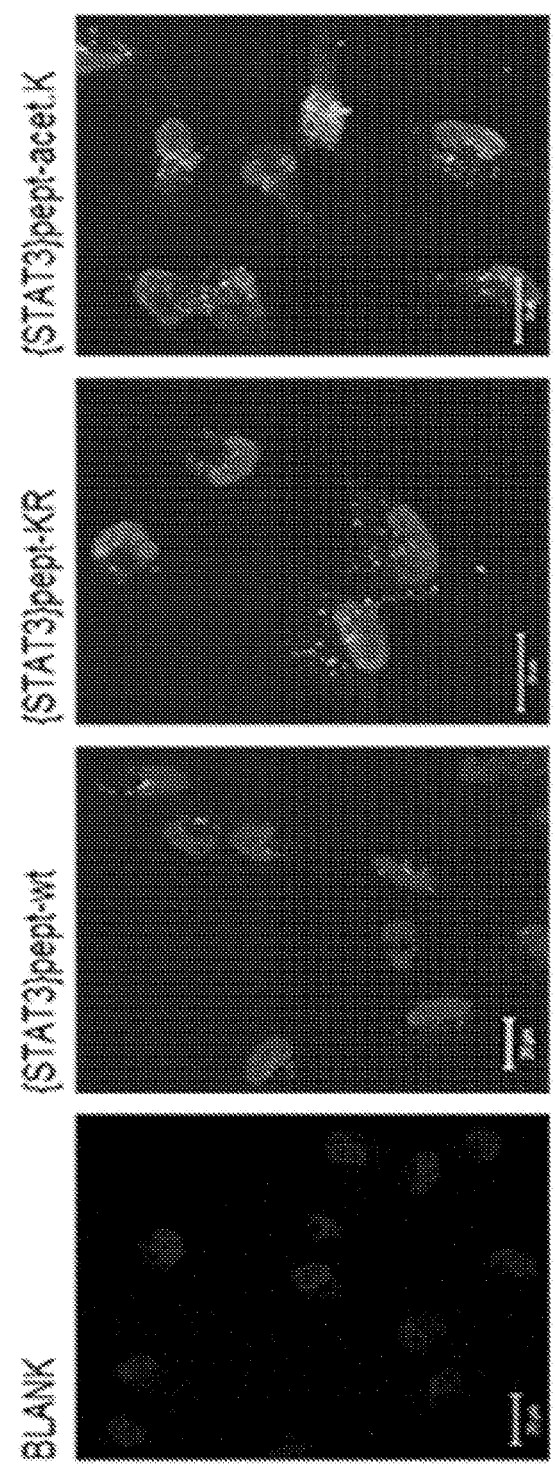
FIGS. 3A-3B.

Example 2: Modified STAT3 Peptides Elongated with Phosphorothioated SSDNA Oligonucleotides Undergo Immediate Early Cellular Internalization Once peptides were modified by hydrazide driven elongation and fluorescently marked to enable intracellular tracking of modified peptides, Applicants assessed immediate early cellular internalization of PS-modified peptides by confocal microscopy and flow cytometry including PO-modified peptides as negative non-internalizing controls. Human glioma U251 cells were incubated for 2 hours with 10 µg/ml of peptide as indicated (FIG. 3A). Fixed cells were analyzed b confocal microscopy for intracellular peptide localization (FIG. 3A).

Figure 3B:
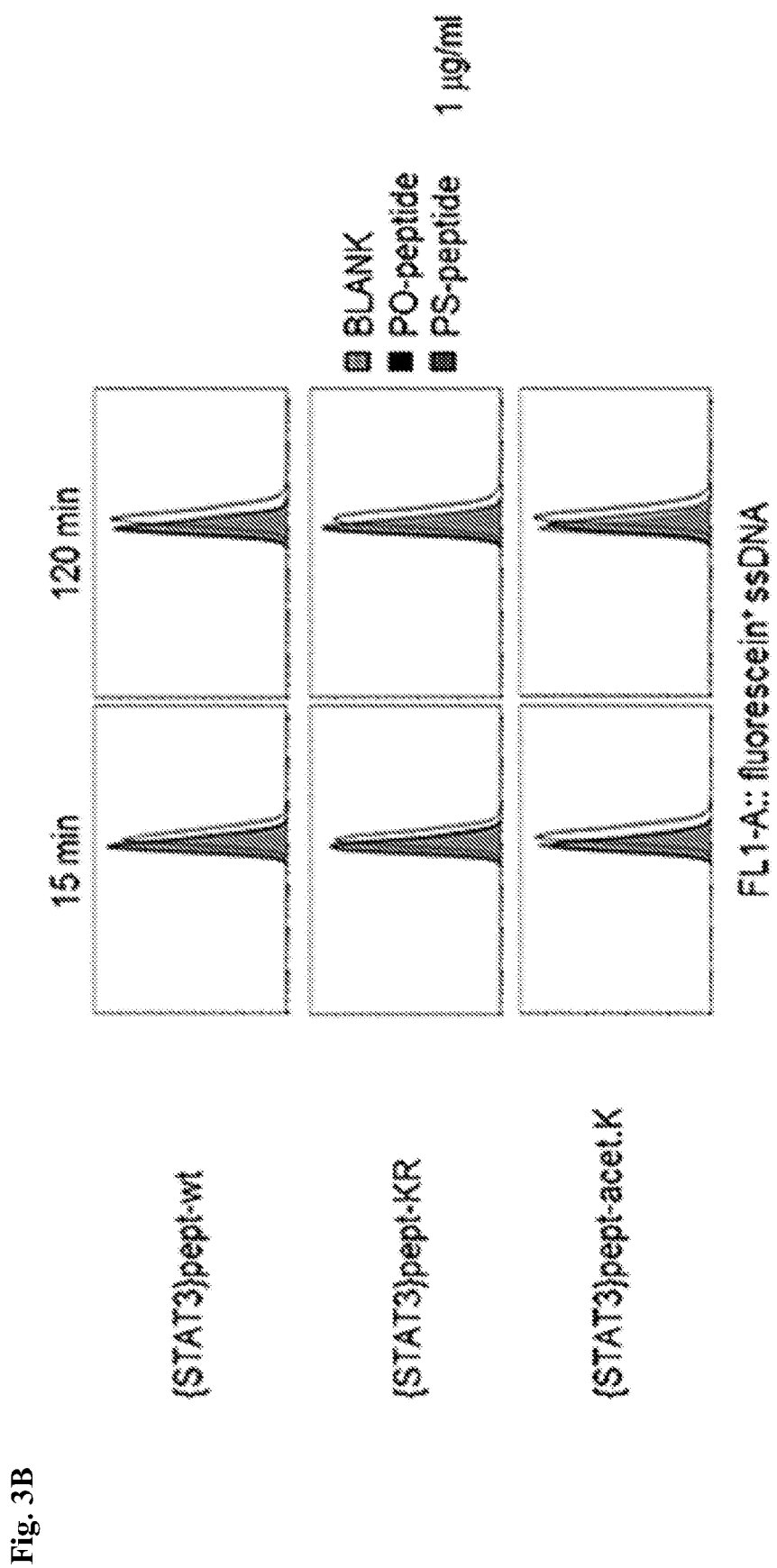

Human glioma U251 cells were incubated for 2 hrs with 1 μg/ml peptide as indicated and analyzed by flow cytometry to assess immediate early cellular load of cells with modified peptide. (FIG. 3B).

Figure 4:
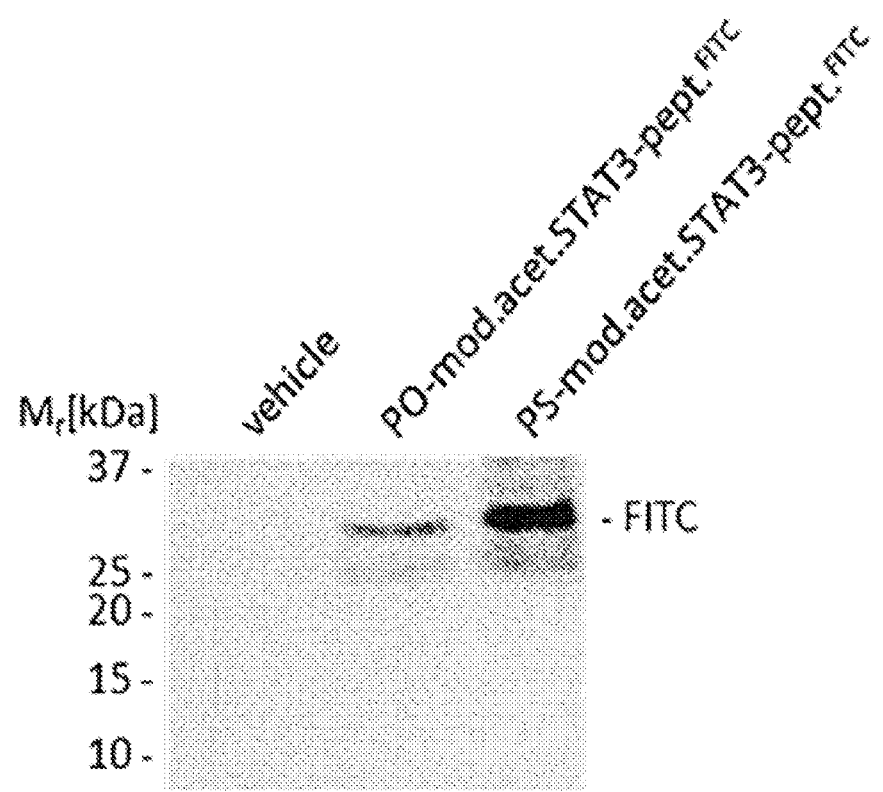
FIG. 4: Attachment of phosphorothioated (PS) ssDNA dramatically improves peptide biostability. Bloodplasma isolated from mice treated as indicated systemically i.v. daily for two weeks with 20 mg/dose was analyzed by Western blotting for modified peptides in peripheral bloodstream showing considerably improved biostability by PS-modification. PO-mod.acet.STAT2-pept.$^{FITC}$ refers to the sequence of SEQ ID NO:3 elongated with non-phosphorothioated control nucleic acids (PO) and including a fluorescent tag (FITC). PS-mod.acet.STAT2-pept.$^{FITC}$ refers to the sequence of SEQ ID NO:3 elongated with phosphorothioated nucleic acids (PS) and including a fluorescent tag (FITC).

Example 3: Attachment of Phosphorothioated (PS) SSDNA Dramatically Improves Peptide Biostatibility In Vivo Bloodplasma isolated from mice treated as indicated systemically (i.v.) daily for two weeks with 20 mg/dose was analyzed by Western blotting for modified peptides in peripheral bloodstream showing considerably improved biostability by PS-modification (FIG. 4).

Example 4: A Novel Acetylation-Specific Competitor Peptide Blocking STAT3 Activation Applicants initially observed that lysine acetylation of tumor promoting transcription factor STAT3 at lysine K685 is critical to engage STAT3 with the karyopherin exportin 7. Exportin 7, once it recognizes acetylated STAT3, physically interacts with STAT3 and facilitates its nuclear egress and subsequent reactivation at the cell membrane in a dynamic cycle of activation (nuclear import; facilitated by importins)-deactivation (nuclear export; facilitated by exportins)-reactivation (nuclear import).[1] The STAT3 dynamic cycling (nucleocytoplasmic shuttling) is required to maintain persistent STAT3 dependent target gene activation and is therefore considered a promising point of therapeutic interference. Without being bound by a particularly theory, targeting the nucleocytoplasmic shuttling can either block the STAT3 activating kinase residing in the cytoplasm or members of karyopherin family (importins, exportins) known to shuttle STAT3 cargo in and out of the cell nucleus. Here, Applicants describe a sequence-specific peptide that competes with STAT3 protein for engagement to exportin 7 and effectively delays tumor growth. Treating human tumors in xenograft model with STAT3 competitor peptide results in gaining expression of tumor suppressor p53 and tumor cell apoptosis indicated by cleaved caspase 3, as well as significantly decreased proliferative activity and tumor blood vessel collapse.

Figure 5B:
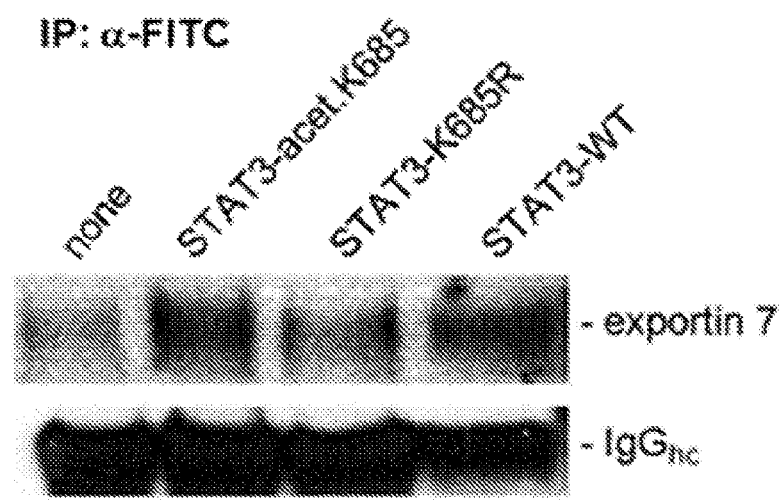

In FIG. 5A, peptide sequences derived from human STAT3 protein are shown. The lysine residue located in the center of the peptide corresponds to lysine 685 in STAT3 protein which is known to undergo acetylation in tumor and inflammatory responses of cells and tissue. Man-made lysine acetylated competitor peptide shows antitumoral activity, while lysine mutation to arginine R (middle) or wild-type (bottom) corresponding sequences has no or little effect on tumor growth kinetics. All peptides were extended into phosphorothioated ssDNA oligos to facilitate cellular internalization (FIG. 5A). The acetylated STAT3 competitor peptide engages with exportin 7 as shown from in vitro assay precipitating the peptide using the FITC fluorophore as a tag which was incorporated into the linker region of peptides (FIG. 5B). Precipitates were analyzed by Western blotting for physical interaction with exportin 7 inside human glioma U251 cells (FIG. 5B).

Figure 6A:
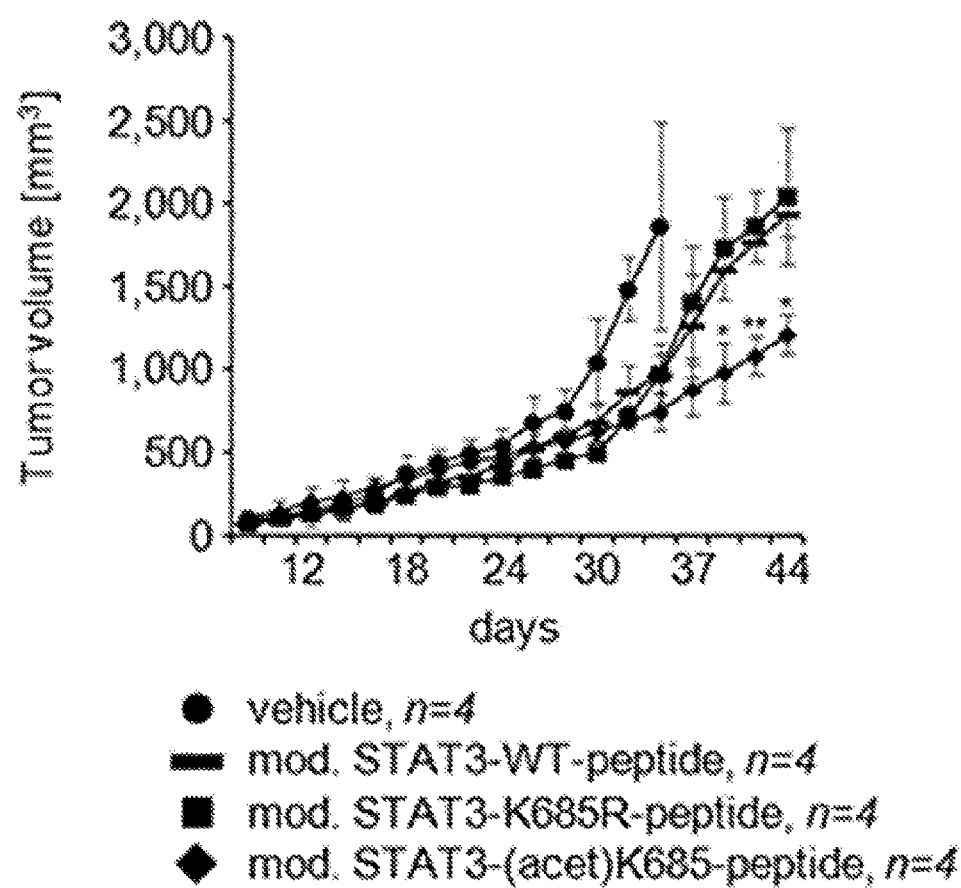
FIGS. 6A-6B: The PS modified STAT3 competitor peptide significantly reduces tumor growth and decreases STAT3 protein interaction with exportin 7 (competition).
Figure 6B:
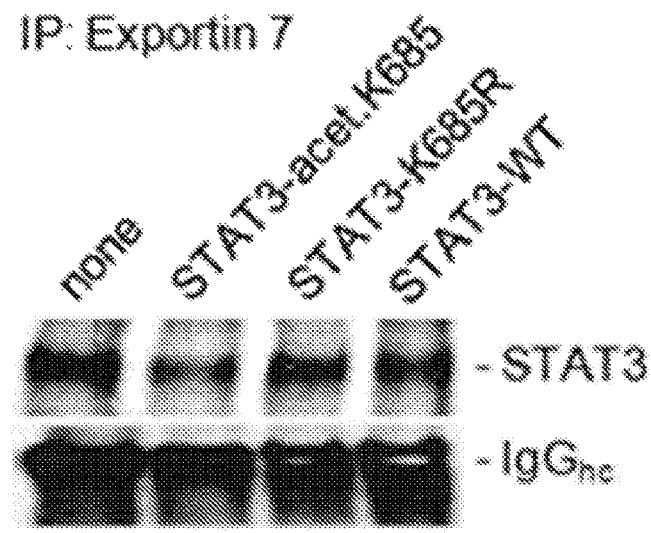

Daily in vivo administration of the STAT3 competitor peptide into human colon cancer (HCT116) bearing mice resulted in significant tumor growth delay. As analyzed from tumor tissue homogenates, the STAT3 competitor peptide considerably reduced the physical interaction of STAT3 protein and exportin 7 (FIGS. 6A and 6B).

The STAT3 competitor peptide significantly reduces tumor growth and decreases STAT3 protein interaction with exportin 7 (competition). Human colon cancer tumor bearing mice were treated daily with 20 mg peptide as inducated and tumor volume was assessed (FIG. 6A). Reduced interaction of STAT3 and exportin 7 was assessed from tumor tissue homogenates by co-precipitation analyzed by Western blotting (FIG. 6B).

Figure 7A:
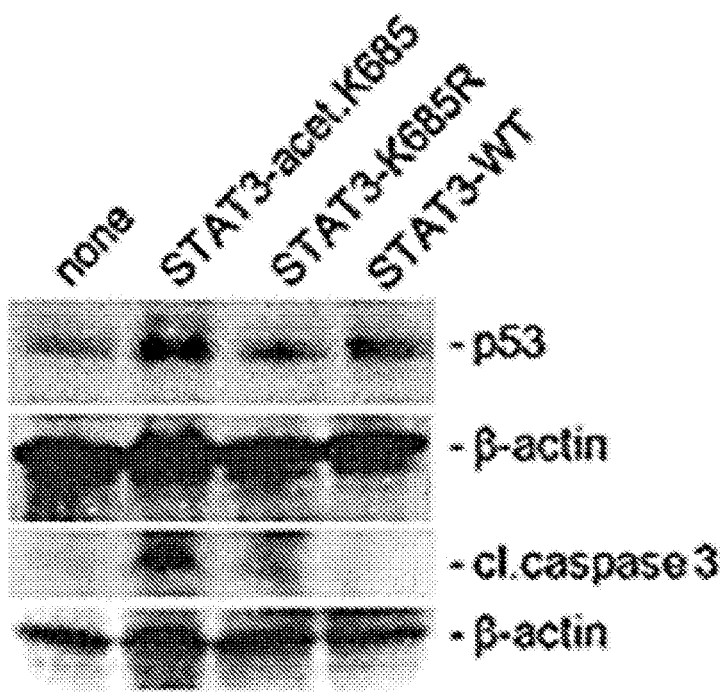
FIGS. 7A-7C: The PS modified STAT3 competitor peptide (STAT3-acet.K685) induced antitumoral responses in human colon cancer tumors in vivo.
Figure 7B:
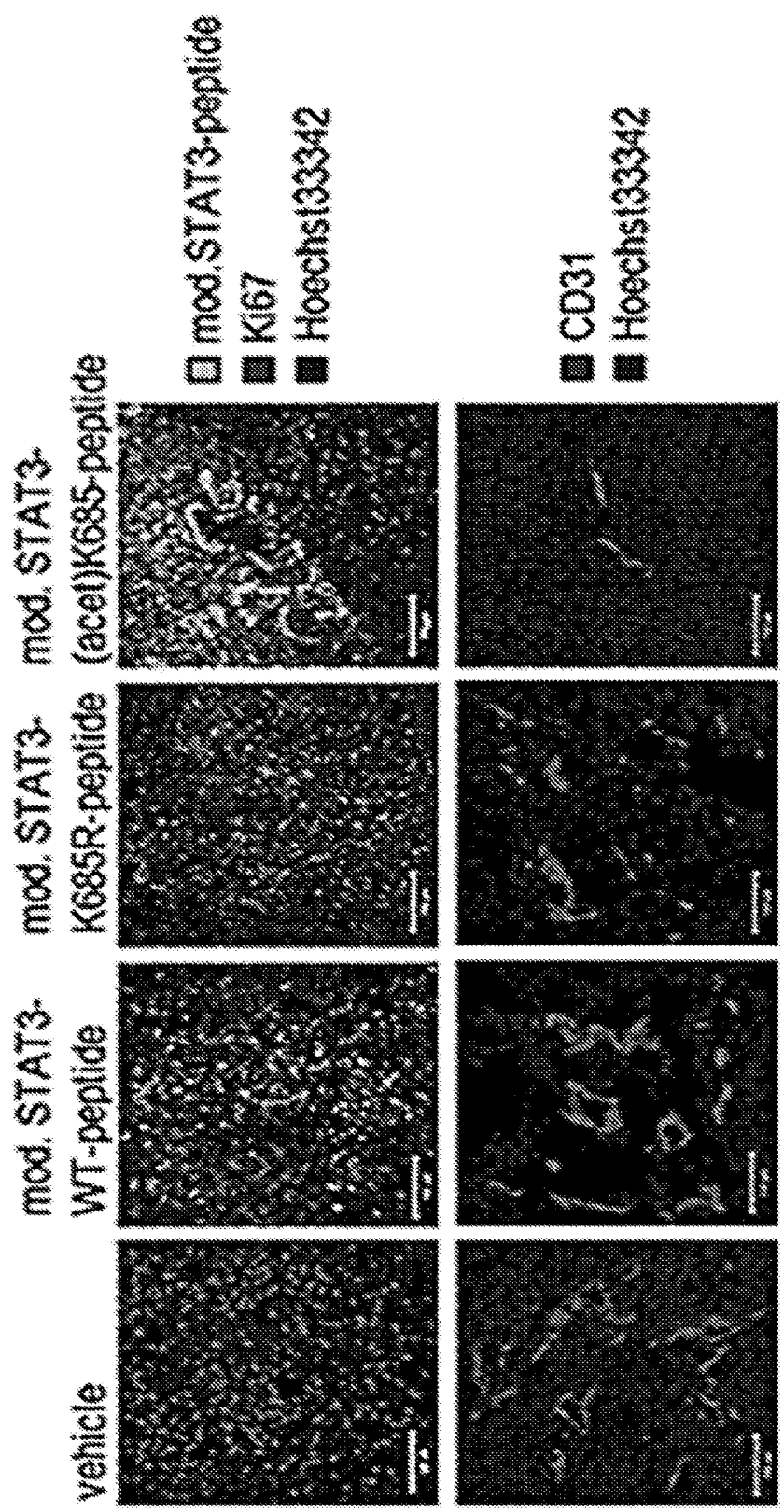
Figure 7C:
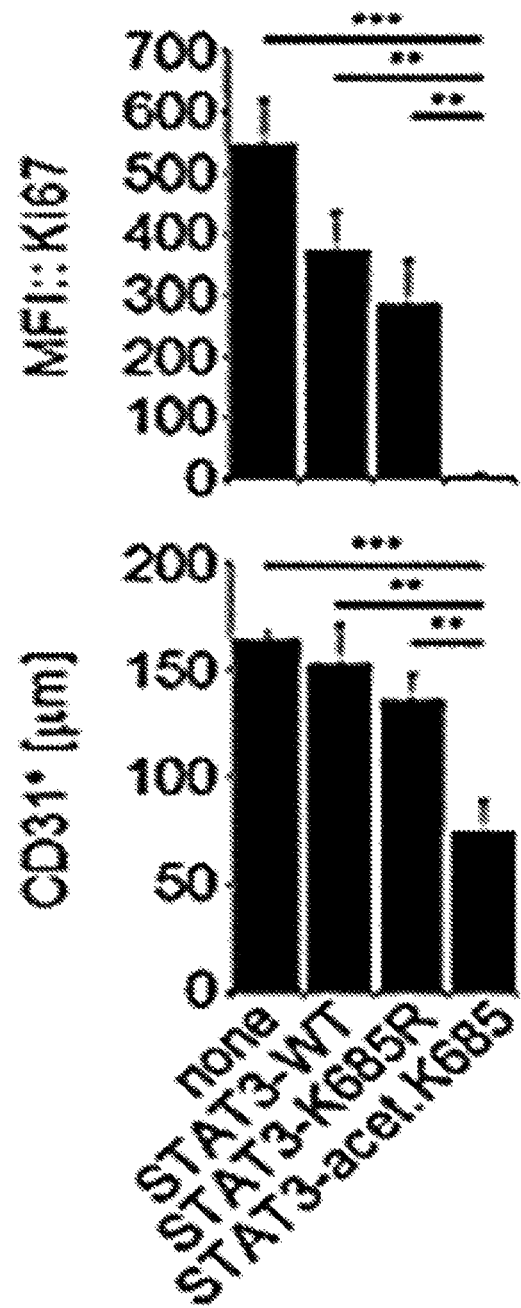

Importantly, in vivo administration of the STAT3 competitor peptide into human colon cancer (HCT116) bearing mice resulted in desired antitumoral activity by upregulating tumor suppressor expression p53 and elevated levels of cleaved caspase 3 indicating induced tumor cell death. Moreover, treating tumor with STAT3 competitor peptide significantly decreased tumor cell proliferation and diminished tumor vessel formation or induced blood vessel collapse (FIGS. 7A-7C).

The STAT3 competitor peptide induced antitumoral responses in human colon cancer tumors in vivo. FIG. 7A shows induced p53 tumor suppressor expression and elevated tumor cell death indicated by cleaved caspase 3 was assessed by Western blot analyses of tumor homogenates. Ki67+ proliferative activity and CD31+ tumor vessels were significantly reduced as analyzed by confocal microscopy (FIG. 7B) and its quantification (FIG. 7C).

Example 5: Inflammatory Response Reducing Peptide

Figure 8:
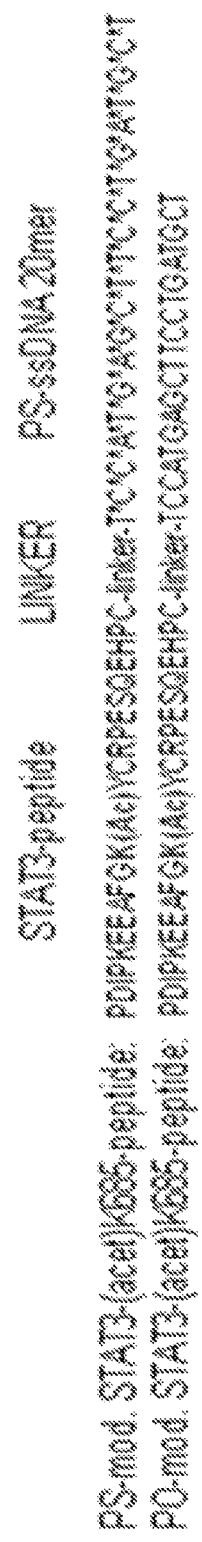
FIG. 8: STAT3 peptide sequence. Shown is the one letter amino acid sequence covering a stretch of the STAT3 protein. In addition, the non-specific sequences of PS-ssDNA 20mer (SEQ ID NO:13) and PO-ssDNA 20mer (SEQ ID NO:13) are also shown. Lysine K685 was modified and man-made acetylated. To achieve cellular internalization, the peptide was extended at its C-terminus by a linker followed by a 20meric ssDNA stretch. It is critical that the sugar-phosphate backbone is phosphorothioated (PS; upper) indicated by (*) to achieve cellular internalization; a control peptide was used without phosphorothioation (phosphodiester, PO; lower)
Figure 9:
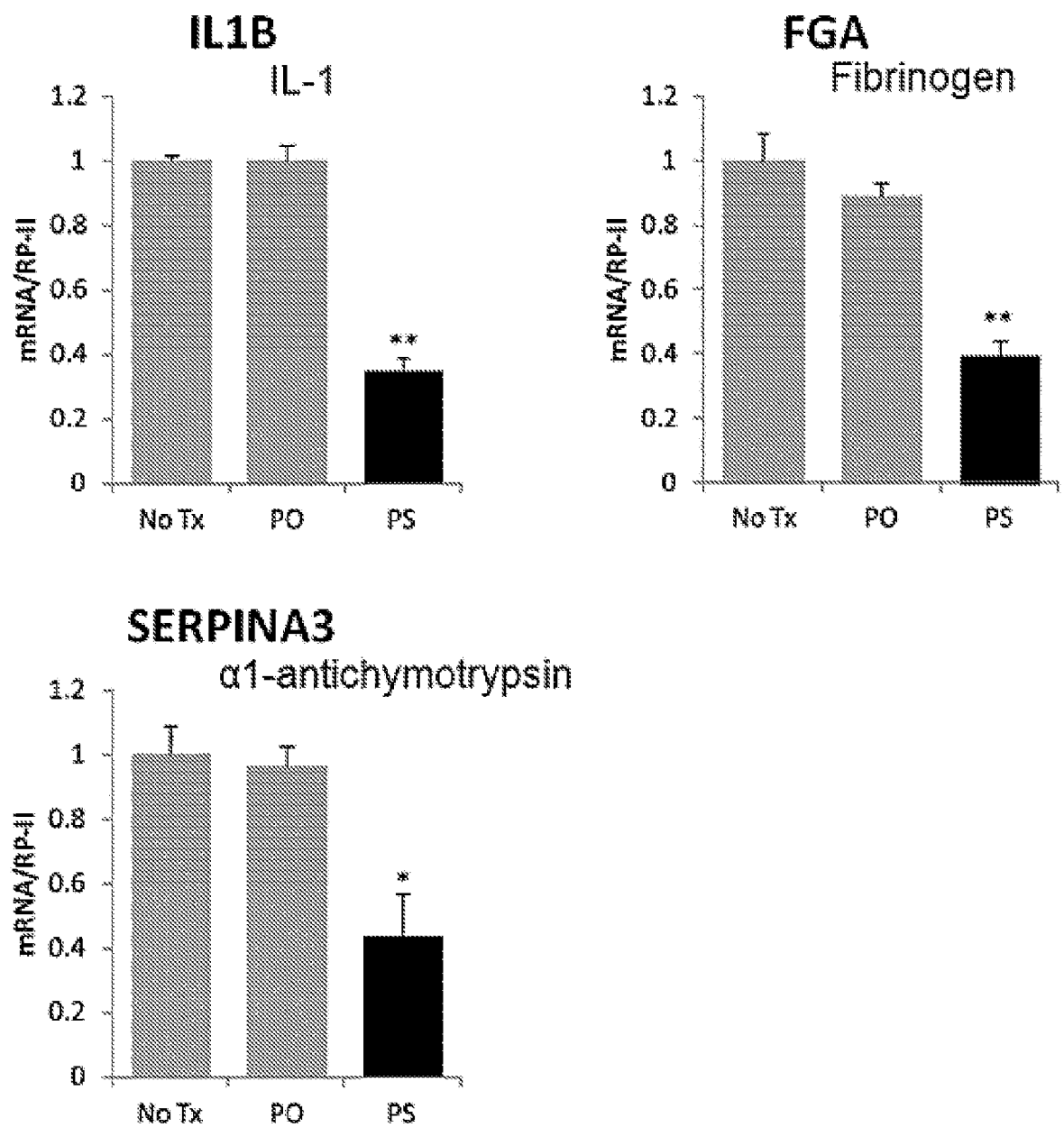
FIG. 9: Cell penetrating, sequence-specific, artificially acetylated STAT3-peptide driven reduction of genes critically involved in the inflammatory response inside tumor. Human colon cancer tumors were treated as indicated with a daily dose of 10 µg peptide locally. Treatment groups: phosphorothioated and artificially acetylated STAT3-peptide (PS), artificially acetylated, non-cell penetrating STAT3-peptide (PO), or no treatment (No Tx). Once tumors were dissected, mRNA was harvested and RT-PCR on a repertoire of human genes critically involved in inflammatory responses was analyzed. SD shown; T-test: *) $P<0.05$, **) $P<0.01$.

Applicants observed that sequence-specific, artificially acetylated STAT3-peptides modified by phosphorothioated ssDNA extension (FIG. 8) significantly reduce a repertoire of molecules involved in molecular regulation of inflammation (FIG. 9).

Shown in FIG. 8 is the one letter amino acid sequence covering a stretch of the STAT3 protein. Lysine K685 was modified and artificially acetylated, as indicated by (Ac). To achieve cellular internalization, the peptide was extended at its C-terminus by a linker followed by a 20meric ssDNA stretch. It is critical that the sugar-phosphate backbone is phosphorothioated, indicated by (*), to achieve cellular internalization (FIG. 8 PS; upper). A control peptide was used without phosphorothioation (FIG. 8; phosphodiester, PO; lower).

Applicants determined the influence of artificially acetylated, cell penetrating phosphorothioated STAT3-peptide on expression of genes critically involved in the inflammatory response inside tumors. Human colon cancer tumors were treated with either artificially acetylated and phosphorothioated STAT3-peptide (PS), artificially acetylated and non-cell penetrating STAT3-peptide (PO), or received no treatment (No Tx). Treated human colon cancer tumors received a daily dose of 10 μg of peptide locally. Once tumors were dissected, mRNA was harvested and RT-PCR on a repertoire of human genes critically involved in inflammatory responses was analyzed. Shown in FIG. 9 are mRNA expression levels normalized by RP-II for IL-1, encoded by the IL1B gene, fibrinogen, encoded by the FBA gene, and al-antichymotrypsin, encoded by the SERPINA3 gene. Treatment with PS, but not PO, resulted in a significant reduction in expression of these genes (FIG. 9).

Example 6: Non-Opioid Pain Reducing Peptide Conjugates

Figure 10:
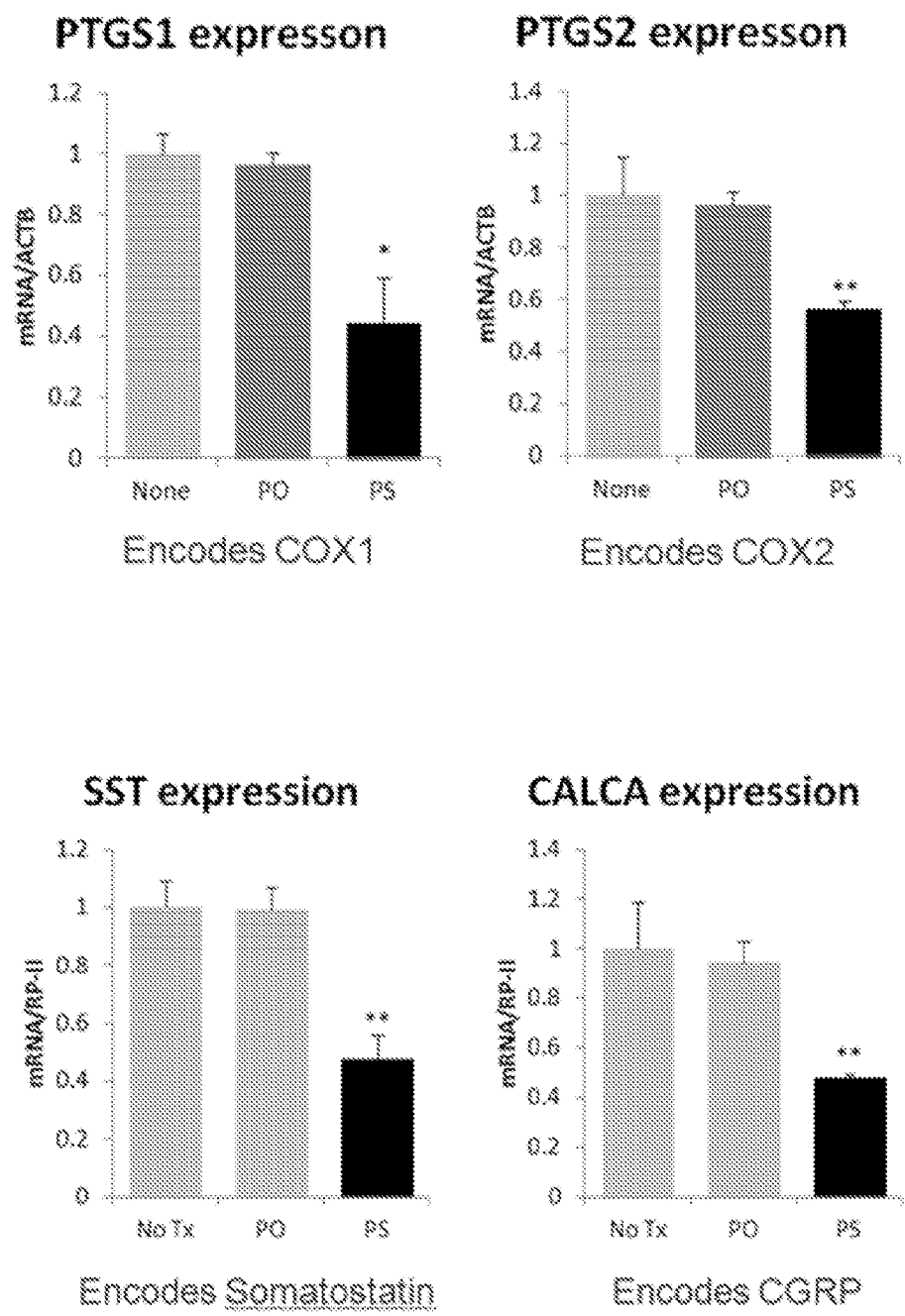
FIG. 10: Cell penetrating, sequence-specific, artificially acetylated STAT3-peptide driven reduction of genes critically involved in pain regulation. Human colon cancer tumors were treated as indicated with a daily dose of 10 µg of peptide locally. Treatment groups: phosphorothioated and artificially acetylated STAT3-peptide (PS), artificially acetylated, non-cell penetrating STAT3-peptide (PO), or no treatment (No Tx or None). Once tumors were dissected, mRNA was harvested and RT-PCR on a repertoire of human genes (i.e., PTGS1, PTGS2, SST, and CALCA) critically involved in pain regulation was analyzed. SD shown; T-test: *) $P<<0.05$, **) $P<0.01$.

Applicants observed that sequence-specific, artificially acetylated STAT3-peptides modified by phosphorothioated ssDNA extension (FIG. 8) significantly reduced a repertoire of molecules involved in the molecular regulation of pain (FIG. 10).

To determine the influence of artificially acetylated, cell penetrating phosphorothioated STAT3-peptide on expression of genes critically involved in pain regulation, human colon cancer tumors were treated with either artificially acetylated and phosphorothioated STAT3-peptide (PS), artificially acetylated and non-cell penetrating STAT3-peptide (PO), or received no treatment (No Tx or None). Treated human colon cancer tumors received a daily dose of 10 μg of peptide locally. Once tumors were dissected, mRNA was harvested and RT-PCR on a repertoire of human genes critically involved in pain regulation was analyzed. FIG. 10 shows mRNA expression levels normalized by either RP-II or ACTB for PTGSI which encodes COX1, PTGS2 which encodes COX2, SST which encodes Somatostatin, and CALCA which encodes CGRP. Treatment with PS, but not PO, resulted in a significant reduction in expression of these genes (FIG. 10).

Figure 11:
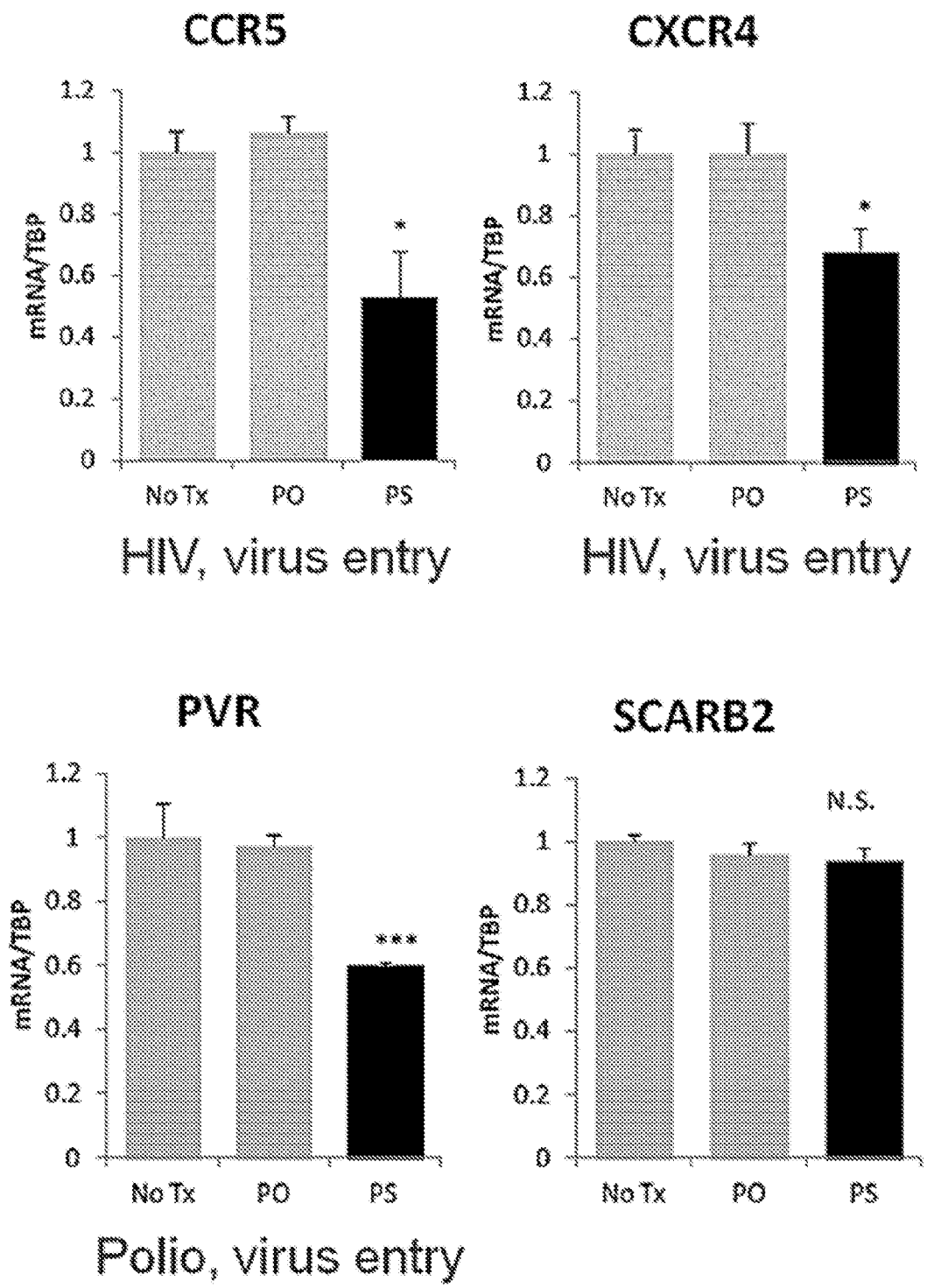
FIG. 11: STAT3-peptide driven reduction of expression of virus receptors. Human colon cancer tumors were treated as indicated with a daily dose of 10 µs peptide locally. Treatment groups: phosphorothioated and artificially acetylated STAT3-peptide (PS), artificially acetylated, non-cell penetrating STAT3-peptide (PO), or no treatment (No Tx). Once tumors were dissected, mRNA was harvested and RT-PCR on a repertoire of human genes critically involved in virus particle entry into cells was analyzed. SD shown; T-test: *) $P<0.05$, ***) $P<0.001$, NS) Not Significant.
Figure 12A:
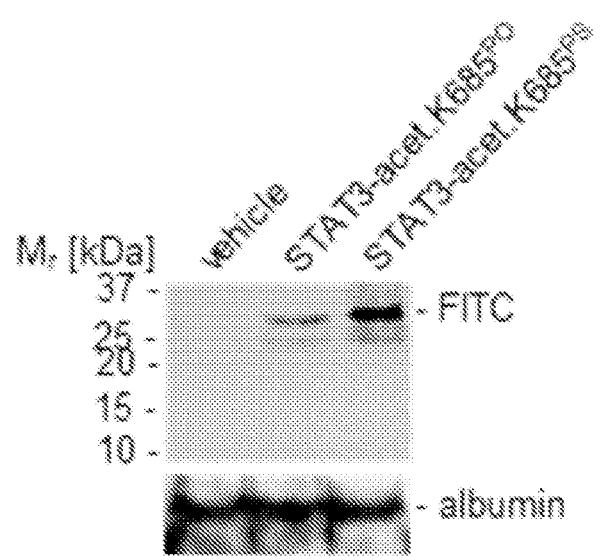
FIGS. 12A-12B: PS-modified acetylated STAT3 peptide has improved biostability and biodistribution capacities. Mice bearing human colon carcinoma tumors were treated with peptides as indicated via systemic administration daily.
Figure 12B:
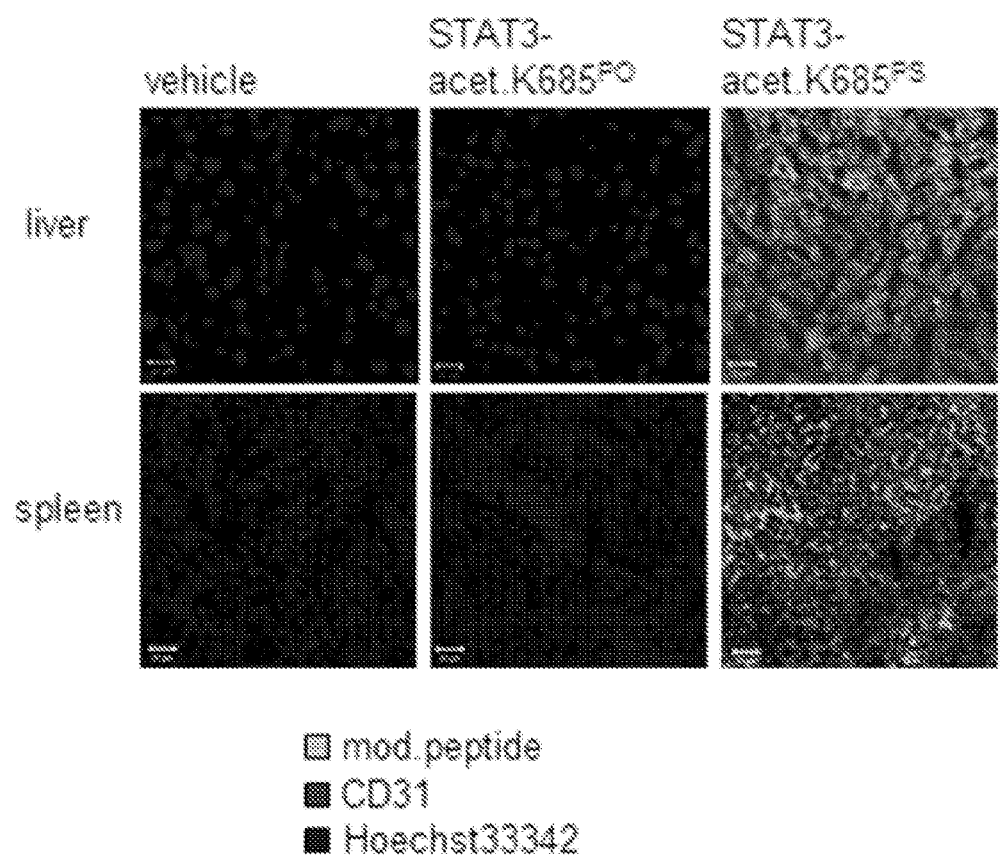
Figure 12B:
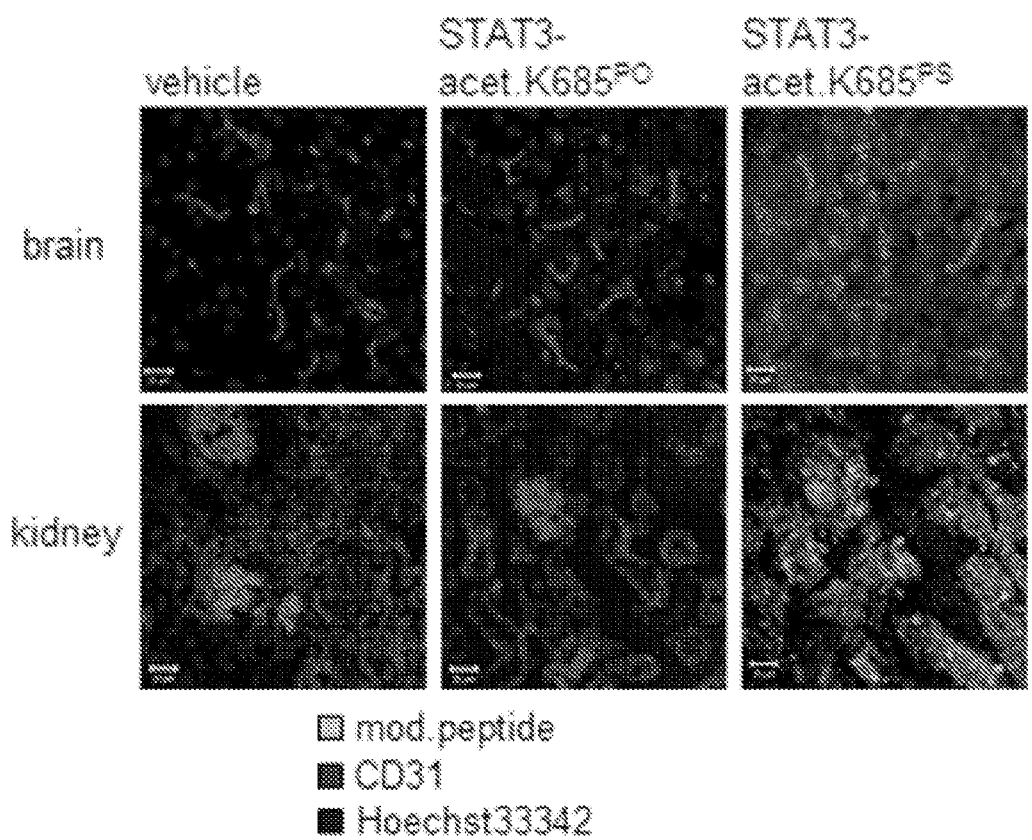

Example 7: A Cell Penetrating Peptide that Reduces Virus Infection Susceptibility Applicants observed that sequence-specific, artificially acetylated STAT3-peptides modified by phosphorothioated ssDNA extension (FIG. 8) significantly reduced the expression of virus surface receptors involved in virus entry (FIG. 11). Notably, affected virus receptors are CCR5 and CXCR4; CCR5 (CD195) and CXCR4 (CD184) are receptors that initially engage HIV particles and facilitate cellular entry. Moreover, the poliovirus receptor PVR (CD155) is significantly reduced in transcriptional expression once cells were treated with the cell-penetrating peptide. General endocytic molecule encoded by the SCARB2 gene was not affected and served as a control gene in the analyses.

Example 8: Modified GP130-Peptides Reducing Acute-Phase Inflammatory Response

Figures 13A, 13B:
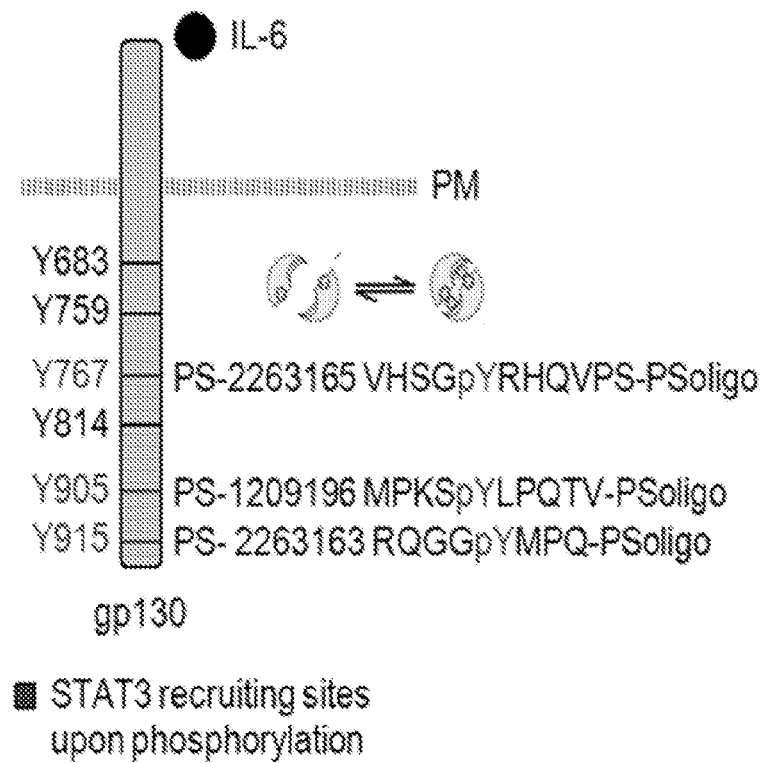
FIGS. 13A-13B: IL-6Rbeta (gp130) peptide sequence.
Figure 14A:
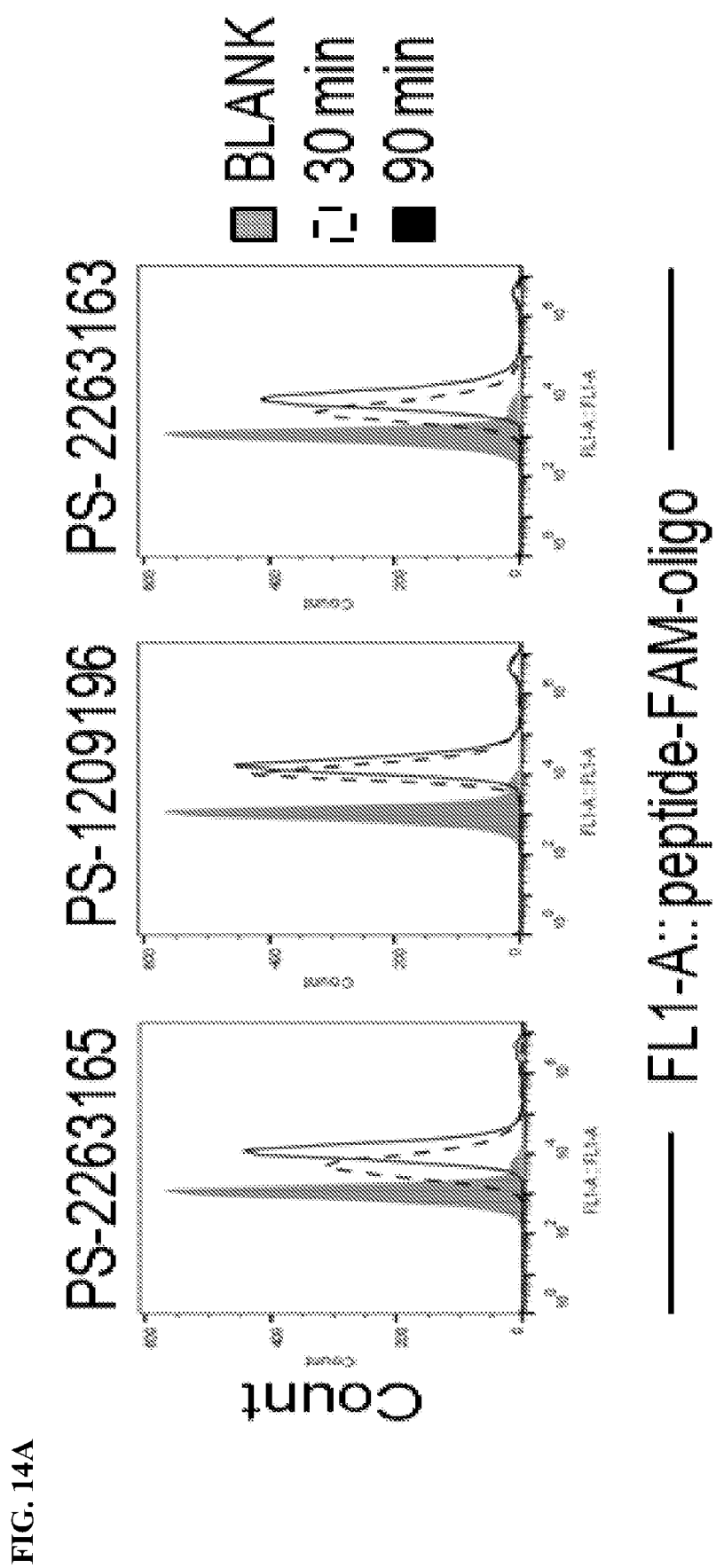
FIGS. 14A-14B: gp130-peptide internalization by tumor cells.
Figure 14B:
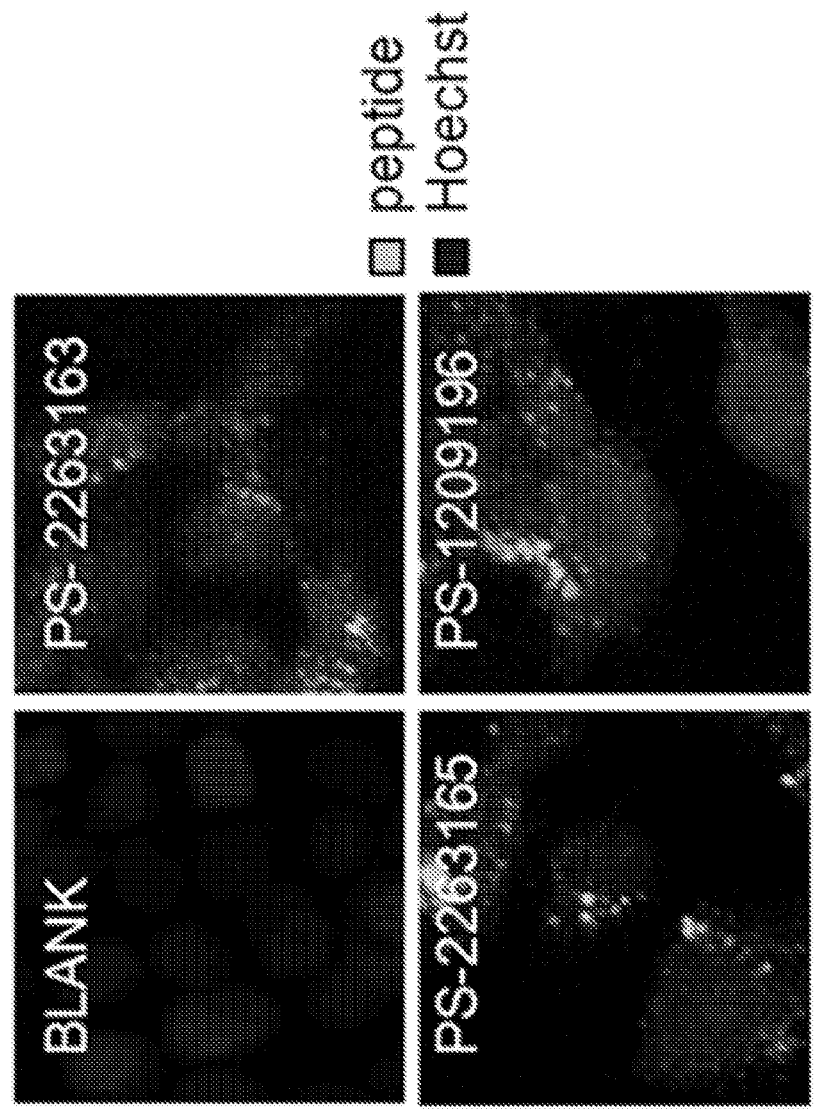
Figure 15:
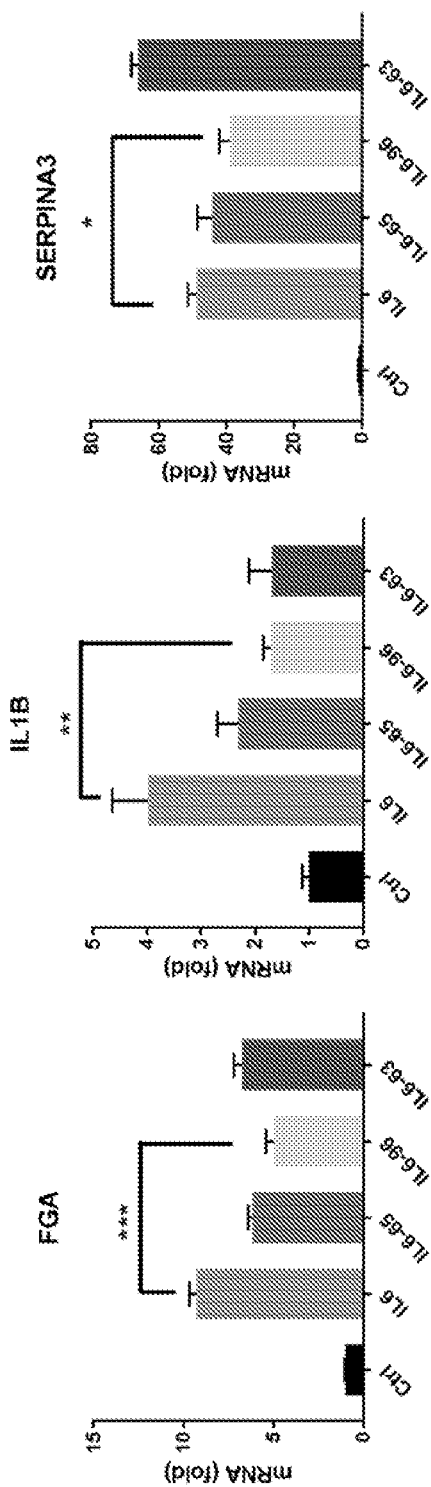
FIG. 15: gp130-peptide treatment of cancer cells significantly reduces IL-6/gp130/STAT3 target genes. Human hepatoma cells HepG2 were treated as indicated with 1.0 µM gp130-peptide (i.e., IL6-65 represents phosphorothioate elongated SEQ ID NO:4, IL6-96 represents phosphorothioate elongated SEQ ID NO:8, and IL-63 represents phosphorothioate elongated SEQ ID NO:9) for 24 h upon IL-6 stimulation. mRNA was isolated and target gene expression was assessed by RT-PCR. SD shown; T-test: *) $P<0.05$, ) $P<0.01$, *) $P<0.001$.

Interleukin-6 (IL-6) signaling feeds intracellular STAT3 activity by binding to the extracellular domain of IL-6Ralpha (gp80) recruiting the signaling co-receptors IL-6Rbeta (gp130). IL-6 engagement to these receptors leads to the phosphorylation of 6 tyrosine residues in the cytoplasmic tail of gp130; 3 of those phospho-tyrosines (pY767, pY905 and pY915) serve as the major docking sites recognized by STAT3s SH2 domain initiating STAT3 intracellular signaling. Applicants disclose these three gp130-peptides modified by phosphorothioated ssDNA extension (FIG. 13) considerably reduce expression of a repertoire of IL-6/gp130/STAT3 target genes orchestrating the acute-phase inflammatory response (FIG. 15) once they undergo cellular internalization (FIG. 14).

Example 9: Interleukin-6 Signaling Reducing GP130-Peptide in Cancer Cells

Interleukin-6 (IL-6) signaling feeds intracellular STAT3 activity by binding to the extracellular domain of IL-6Ralpha (gp80) recruiting the signaling co-receptors IL-6Rbeta (gp130). IL-6 engagement to these receptors leads to the phosphorylation of 6 tyrosine residues in the cytoplasmic tail of gp130; 3 of those phosphor-tyrosines (pY767 [SEQ ID NO:4], pY905 [SEQ ID NO:8], and pY915 [SEQ ID NO:9]) serve as the major docking sites recognized by STAT3s SH2 domain initiating STAT3 intracellular signaling Applicants disclose those three gp130-peptides modified by phosphorothioated ssDNA extension (FIG. 13) significantly reducing STAT3 activity (FIG. 15) once they undergo cellular internalization (FIG. 14).

Figure 16:
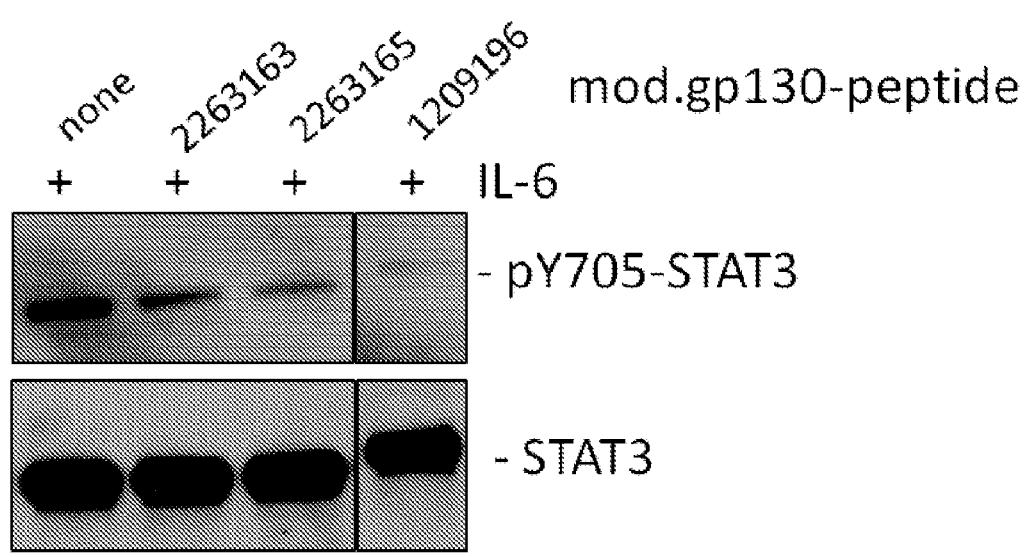
FIG. 16: gp130-peptide treatment of cancer cells inhibits pY-STAT3 activation. Human hepatoma cells HepG2 were treated as indicated with 1.0 µM gp130-peptide peptide (i.e., 2263165 is phosphorothioate elongated SEQ ID NO:4, 1209196 is phosphorothioate elongated SEQ ID NO:8, and 2263163 is phosphorothioate elongated SEQ ID NO:9) for either 30 min prior to IL-6 stimulation. Whole cell lysates were subjected to electrophoretic protein separation and STAT3 activity was assessed by Western blot detecting phospho-tyrosine. Total STAT3 protein staining was included as a loading control. All three modified gp130-peptides show inhibitory efficacy on pY-STAT3 levels in cancer cells.

Human hepatoma cells HepG2 were treated as indicated with 1.0 uM gp130-peptide for either 30 min prior to IL-6 stimulation. Whole cell lysates were subjected to electrophoretic protein separation and STAT3 activity was assessed by Western blot detecting phospho-tyrosine. Total STAT3 protein staining was included as a loading control. All three modified gp130-peptides show inhibitory efficacy on pY-STAT3 levels in cancer cells (FIG. 16).

Figure 17:
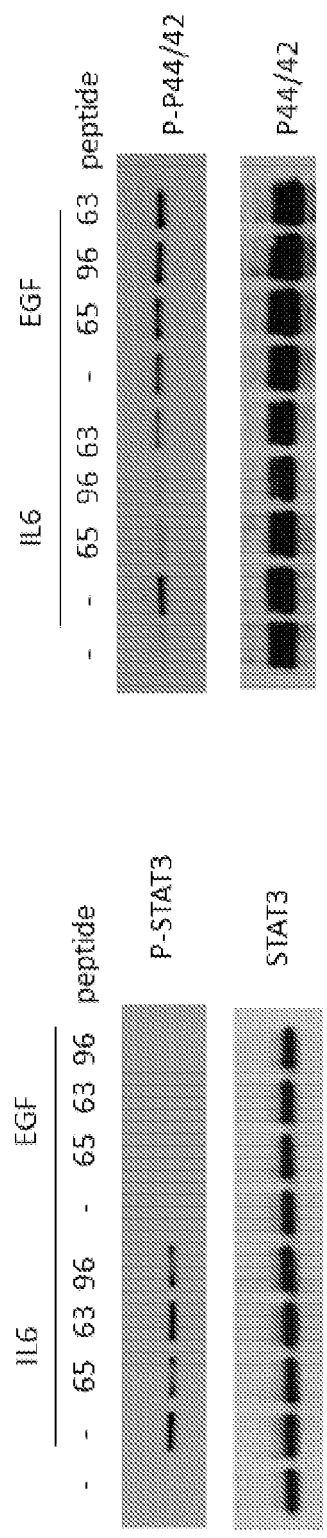
FIG. 17: gp130-peptide treatment of cancer cells specifically inhibits IL-6/gp130 signaling but not EGFR signaling. Human hepatoma cells HepG2 were treated as indicated with 1.0 µM gp130-peptide peptide (i.e., 65 is phosphorothioate elongated SEQ ID NO:4, 96 is phosphorothioate elongated SEQ ID NO:8, and 63 is phosphorothioate elongated SEQ ID NO:9) for either 30 min prior to IL-6 or EGF stimulation. Whole cell lysates were subjected to electrophoretic protein separation and STAT3 as well as MAPK (p42/44) activity was assessed by Western blot. Total STAT3 and MAPK (p42/44) protein staining was included as a loading control.

In an additional experiment, Applicants were able to show that the three modified gp130 peptides are restricted specifically to IL-6 cytokine signaling employing gp130 but not to EGF signaling, where EGF serves as an extracellular ligand to the EGF-receptor (EGFR) (FIG. 17).

Figure 18:
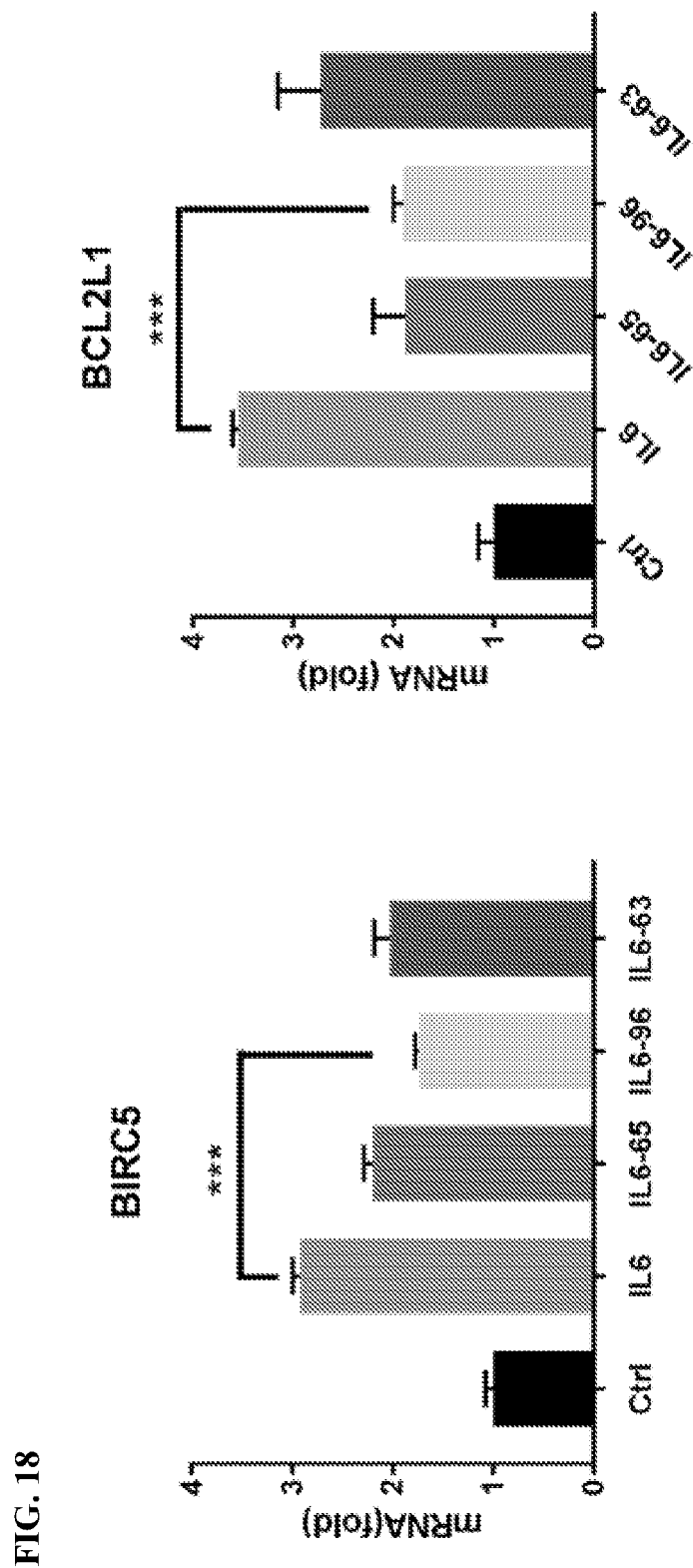
FIG. 18: gp130-peptide treatment of cancer cells significantly reduces IL-6/gp130/STAT3 target genes. Human hepatoma cells HepG2 were treated as indicated with 1.0 µM gp130-peptide (i.e., IL6-65 represents phosphorothioate elongated SEQ ID NO:4, IL6-96 represents phosphorothioate elongated SEQ ID NO:8, and IL-63 represents phosphorothioate elongated SEQ ID NO:9) for 24 h upon IL-6 stimulation. mRNA was isolated and target gene expression was assessed by RT-PCR. SD shown; T-test: ***) $P<0.001$.
Figure 19A:
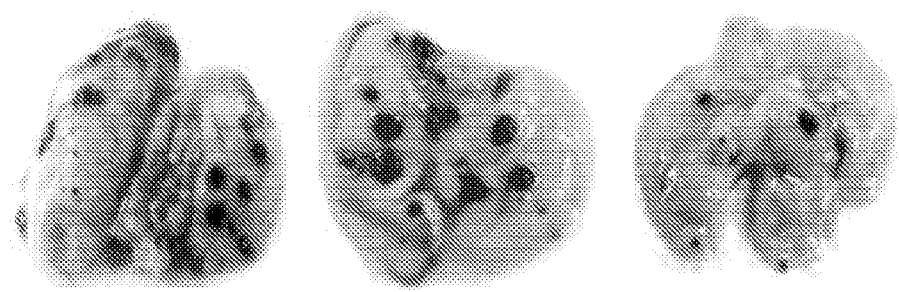
FIGS. 19A-19C: Systemic treatment with modified STAT3-peptide reduces tumor growth. B16 murine melanoma cell line was retro-orbitally injected into C57BL/6 mice. One day after tumor injection, mice were treated daily with 19 µM (19 µM=40 µg/mouse) control-modified STAT3-peptide, modified STAT3 peptide and (HBSS) until the control mice were moribund.
Figure 19B:
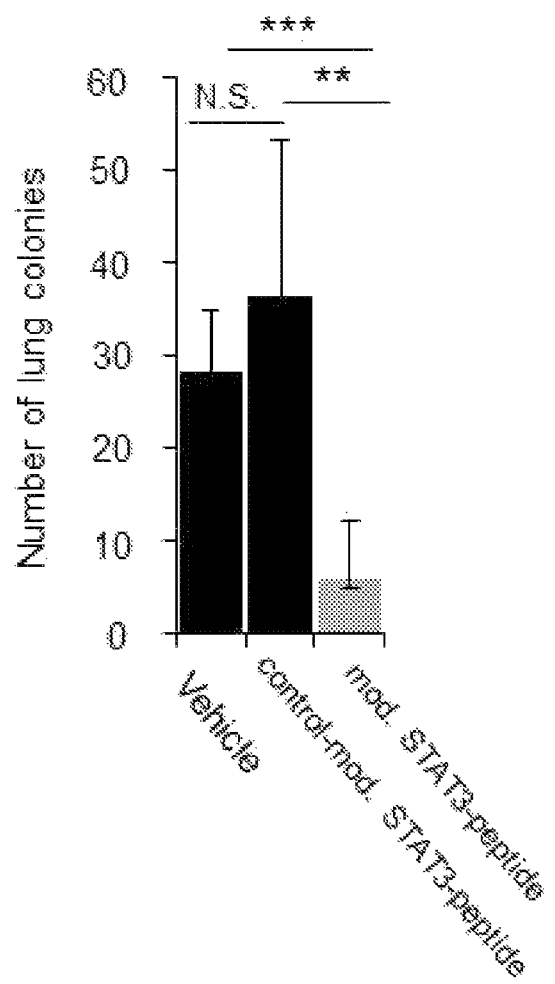
Figure 19C:
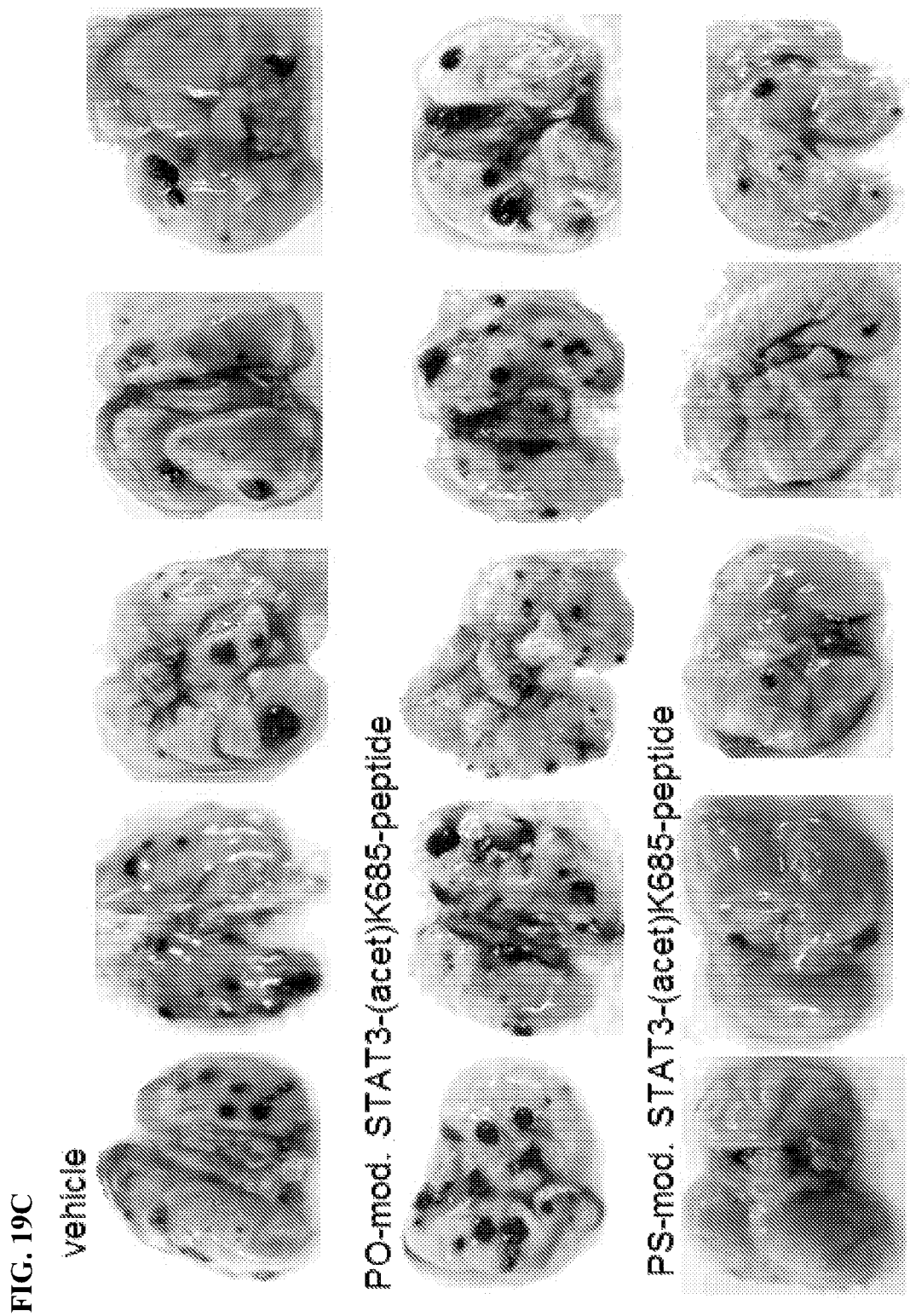

Moreover, treatment of cancer cells with modified gp130 peptides significantly reduced the expression of cancer cell survival genes such as survivin (BIRC5) and BclXL (BCL2L1) as assessed by RT-PCR upon treating human hepatoma HepG2 cells with peptides as indicated (FIG. 18).

Figure 20B:
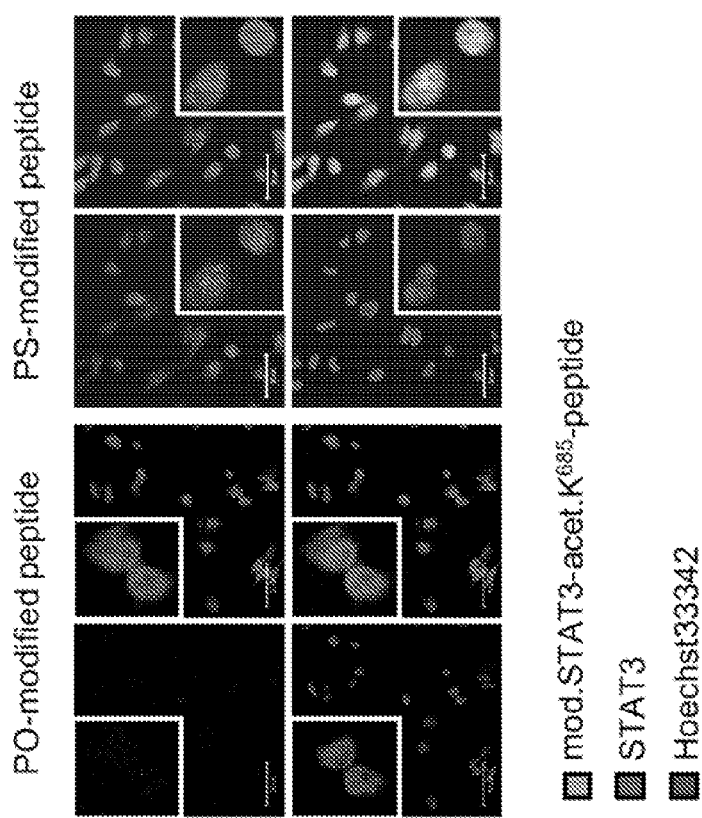
FIGS. 20A-20I: Conjugating phosphorothioated DNA oligonucleotides (PS) enables acetyl-STAT3 peptide cell penetration and specific interaction with STAT3 and exportin 7 proteins as well as downregulation of STAT3 activation.
Figure 20A:
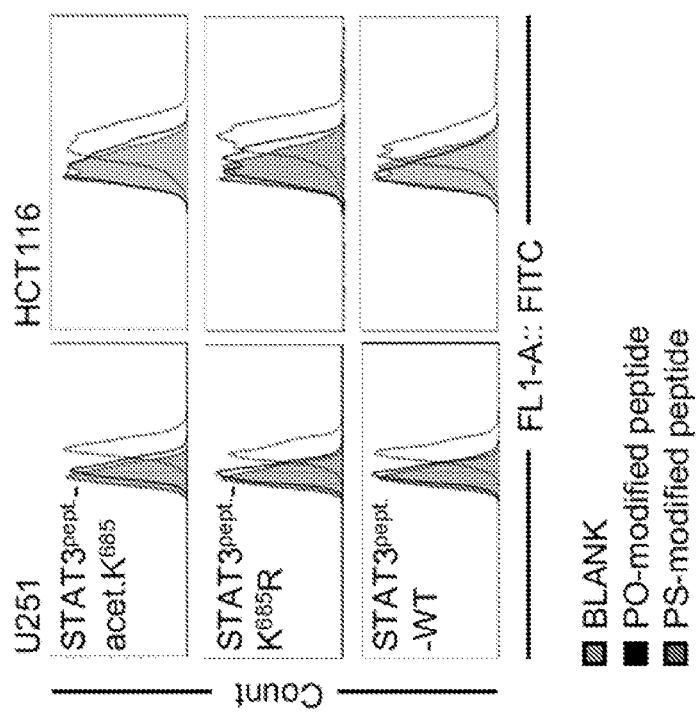

Example 10: Conjugating Phosphorothioated DNA Oligonucleotides (PS) Enabling Acetyl-STAT3 Peptide Cell Penetration, Specific Interaction with STAT3 and Exportin 7 Proteins and Downregulation of STAT3 Activation Phosphorothioated DNA oligonucleotide-modified STAT3 peptides efficiently penetrate human glioma cell line U251 and human colon cancer cell line HCT116, as assessed by flow cytometry (FIG. 20A). Applicants disclose cell penetration of the PS-acetyl-STAT3 peptide and its colocalization with STAT3 protein in U251 cells by confocal microscopy (FIG. 20B) (Scale bars: 50 μm).

Figure 20C:
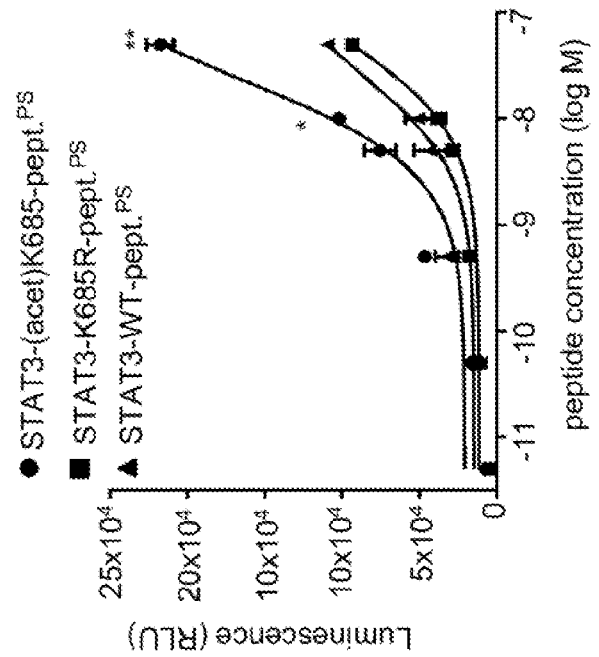
Figure 20D:
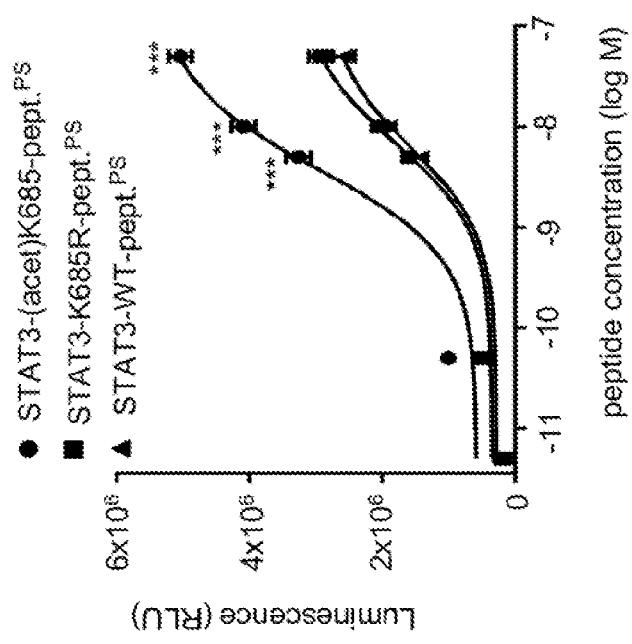
Figure 20F:
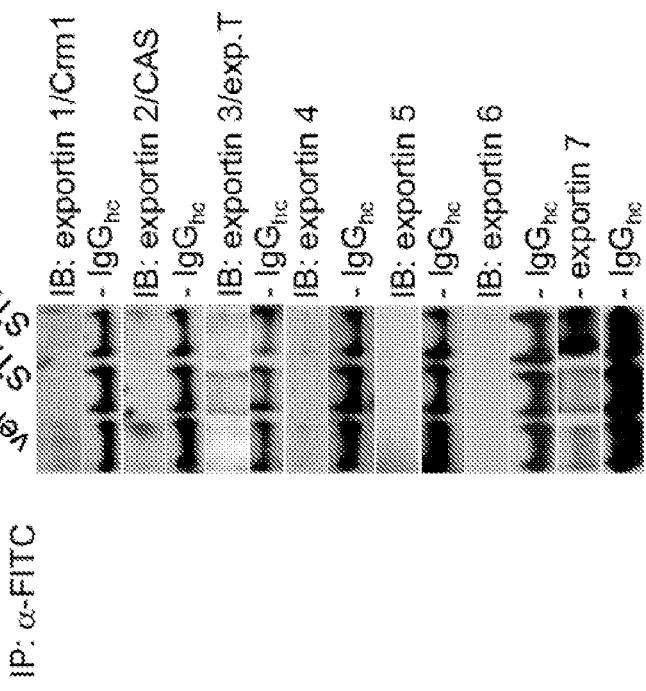
Figure 20E:
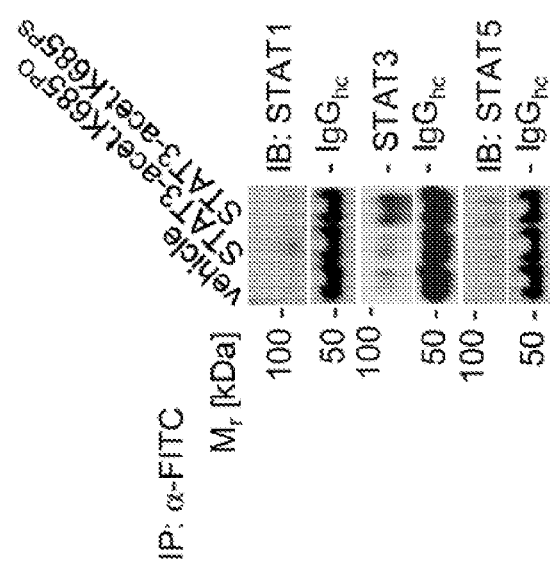

The PS acetyl-STAT3 peptide specifically binds to acetylated STAT3 protein and exportin 7, as assessed by ELISA, in which the plate is coated by an acetylated-STAT3 protein (containing amino acids 127-722), n=3 (FIG. 20C and FIG. 20D). Applica discloses the specific interaction between acetyl-STAT3 peptide and STAT3/exportin 7 by immunoprecipitation of the FITC-labeled PS-acetyl-STAT3 peptide followed by Western blotting, shown in U251 cells (FIG. 20E and FIG. 20F).

Figure 20H:
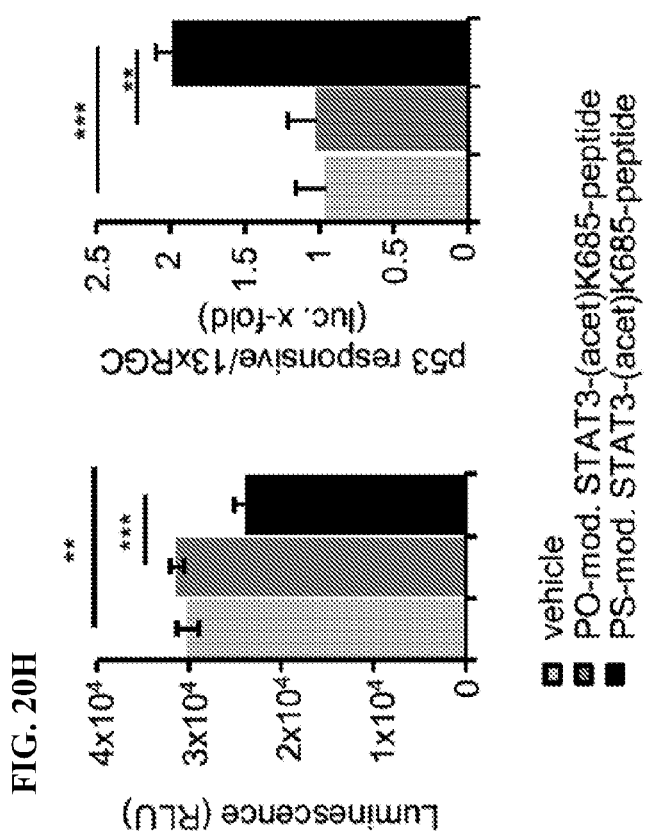
Figure 20G:
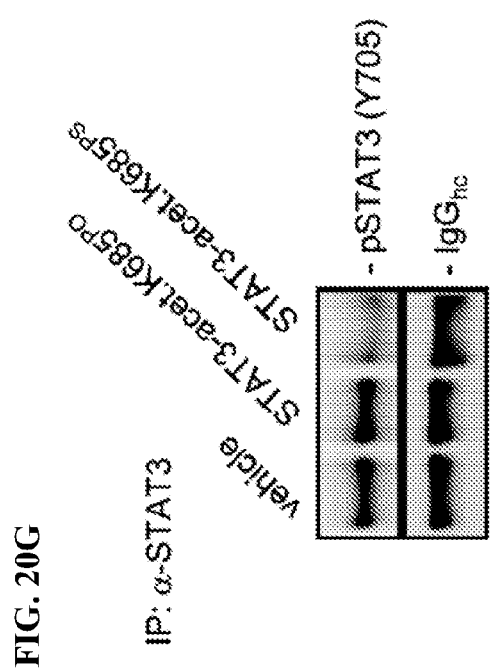
Figure 20I:
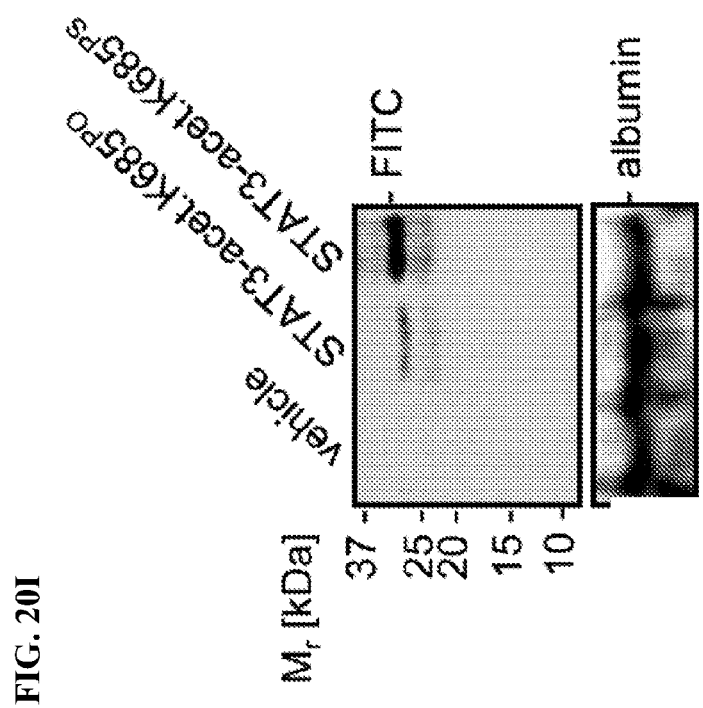

Applicant also discloses downregulation of STAT3 phosphorylation, shown in HCT116 tumors by immunoprecipitation/Western blotting (FIG. 20G). PS-acetyl-STAT3 peptide treatment induces apoptosis of HCT116 colorectal cancer cells (FIG. 20H). Conjugating phosphorothioation DNA oligonucleotides to acetyl-STAT3 peptide increases its biostability, shown by Western blotting to detect FITC labeled-peptide in blood serum of $C_{57}BL/6$ mice collected 24 h after treatment (FIG. 20I).

Figure 21B:
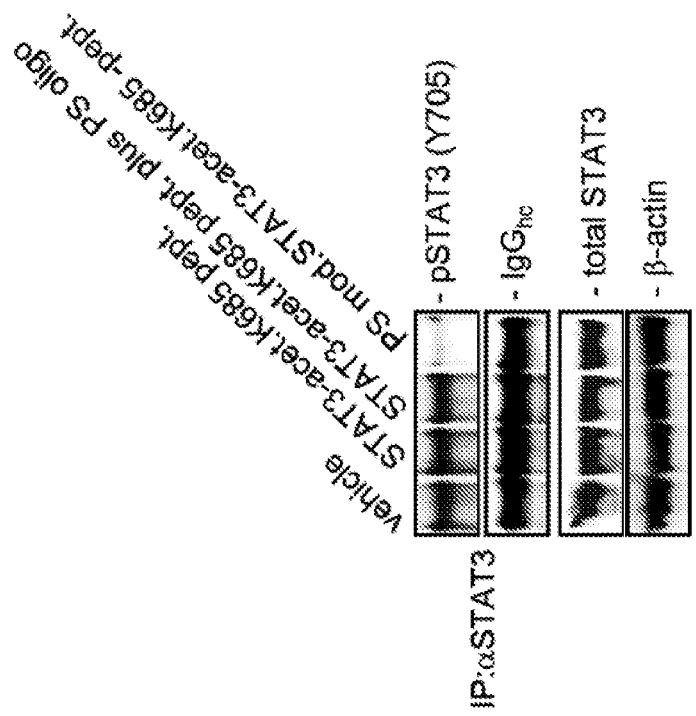
FIGS. 21A-21D: Treatments with the PS-acetyl-STAT3 peptide suppress growth of HCT116 xenograft tumors.
Figure 21A:
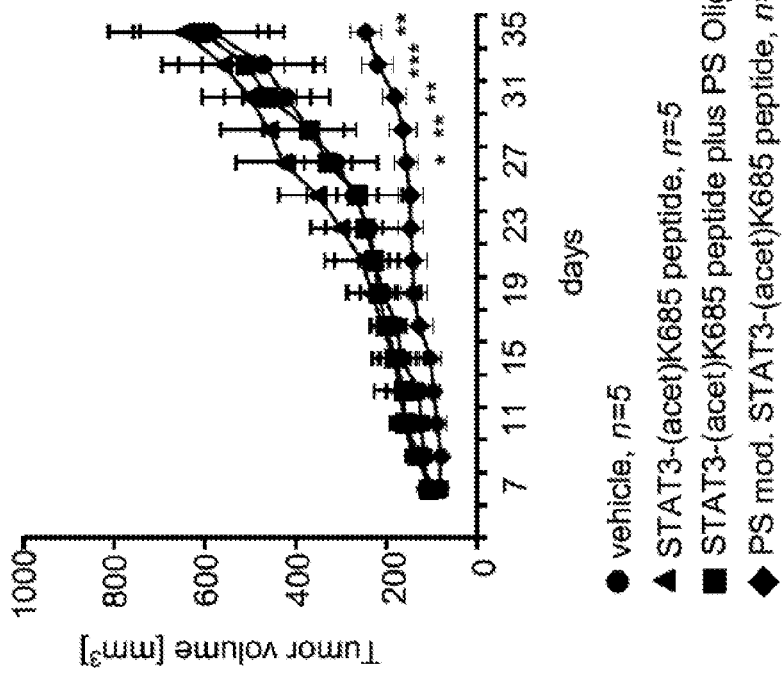
Figure 21C:
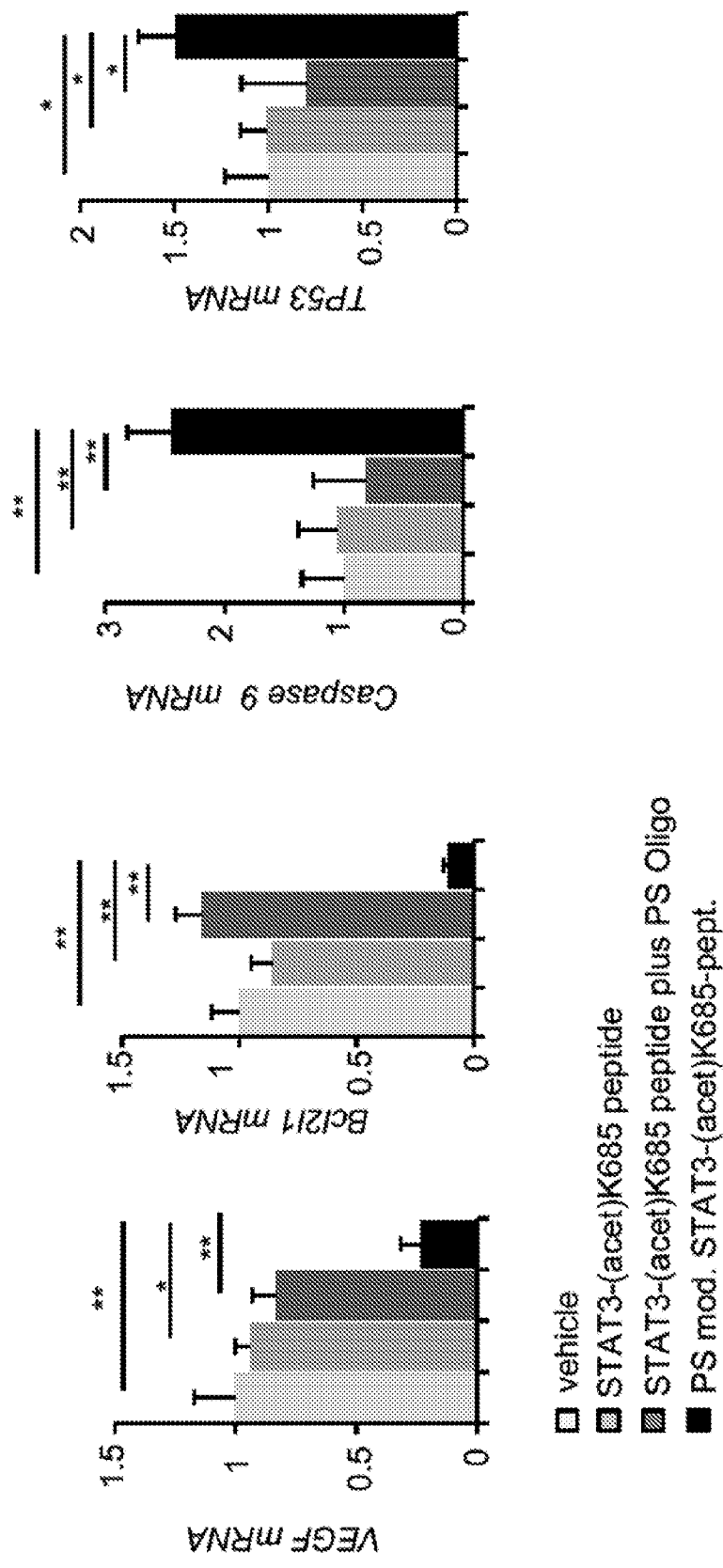

Example 11: Treatments with the PS-Acetyl-STAT3 Peptide Suppressing Growth of HCT116 Xenograft Tumors Growth kinetics of HCT116 tumors in NSG mice systemically treated with acetyl-STAT3 peptides (18.940 μM), with or without the PS oligonucleotide conjugation, every other day (n=5) (FIG. 21A). SD is shown by asterisks. T-test; *; P<0.001; , P<0.01; *, P<0.05. Applicants disclose downregulation of STAT3 activity upon treatments with PS-acetyl-STAT3 peptides, as shown by immunoprecipitation followed by Western blotting (FIG. 21B). Effects of downregulation of STAT3 activity on expression of proliferation- and apoptosis-related genes, as assessed by qRT-PCR in tumor homogenates from tumors are shown in A (FIG. 21C). The mRNA expression levels in the tumor tissues from the control mice are set as 1. T-test; *; P<0.001; , P<0.01; *, P<0.05.

Figure 21D:
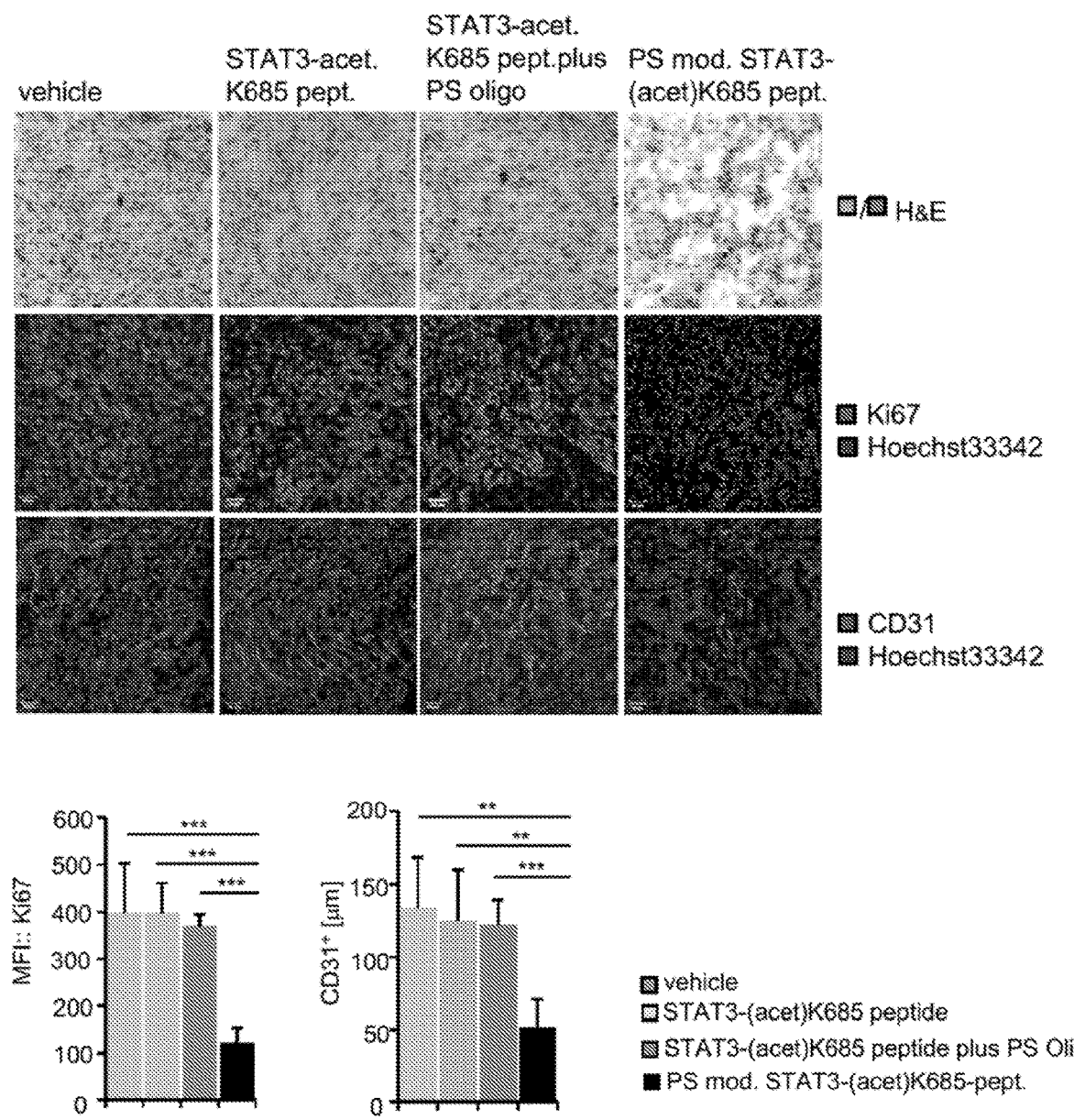

Treatment with the PS-acetyl-STAT3 peptide induces apoptosis and inhibits proliferation and angiogenesis in tumors, as indicated by confocal imaging after H&E staining (upper panel), and immunostaining of Ki-67 and CD-31 proteins in the tumor sections (lower panels) (FIG. 21D). The images are representative of 3 tumors per experimental group in A. Scale bars: 50 µm. The graphs show the quantification for Ki-67 expression levels and of the mean vessel diameter (data include 6 fields of view per group). SD is shown. ** P<0.01.

Figure 22C:
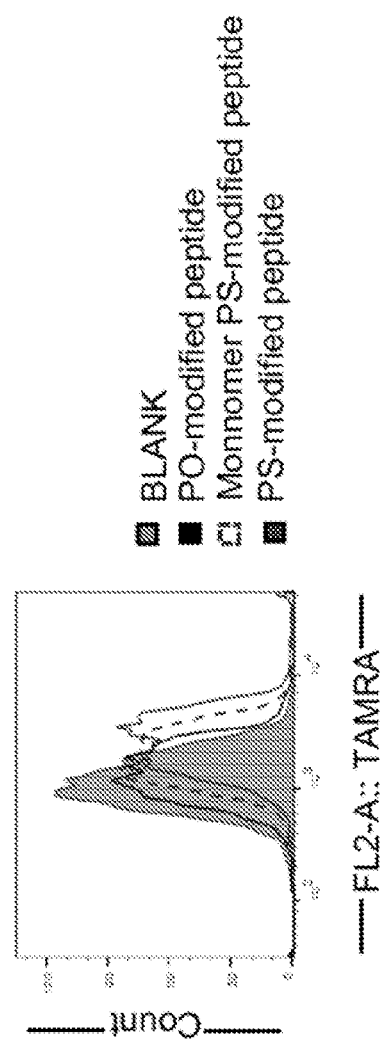
Figure 22B:
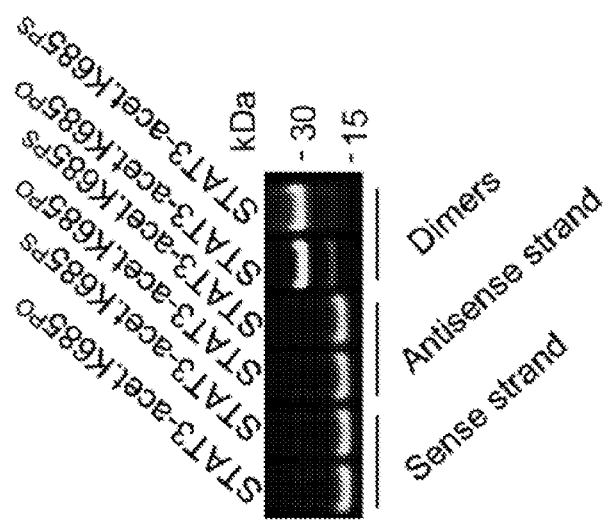

Example 12: Dimerization of the PS-Acetyl-STAT3 Peptide Increasing its Anti-Tumor Effects Applicants disclose structures of non-phosphorothioated (PO) and phosphorothioated DNA oligonucleotide-modified acetyl-STAT3 peptides (FIG. 22A). Dimerization of the peptides is achieved by annealing anti- and sense DNA oligos. Applicants disclose dimerization of non-phosphorothioated and phosphorothioated DNA oligonucleotide-modified peptides by SDS-PAGE (FIG. 22B). Dimerization enhances cell penetration of the peptide, assessed by flow cytometry (FIG. 22C). The enhanced anti-tumor effect of the dimerized PS-acetyl-STAT3 peptide is shown in HCT116 tumors grown in NSG mice (n=5) (FIG. 22D). T-test; **, P<0.01; *, P<0.05.

Figure 22E:
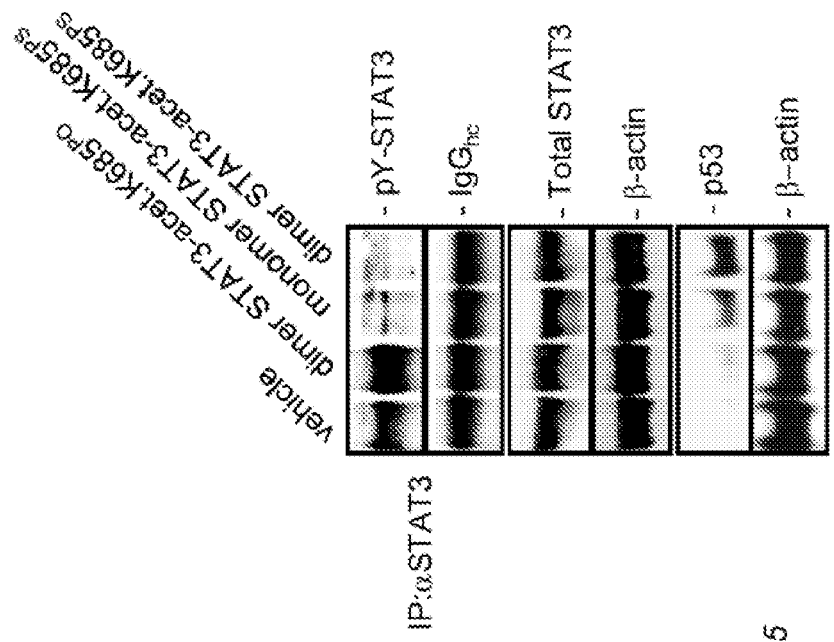
Figure 22D:
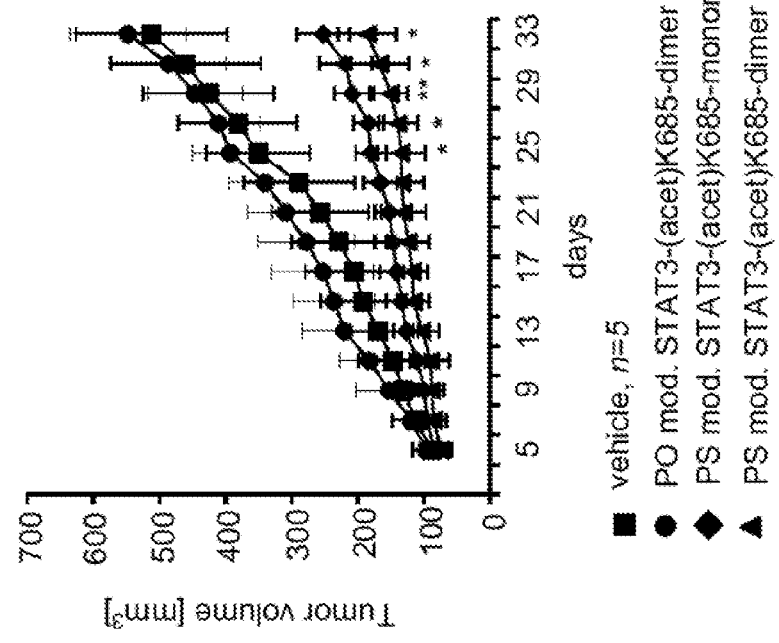
Figure 22F:
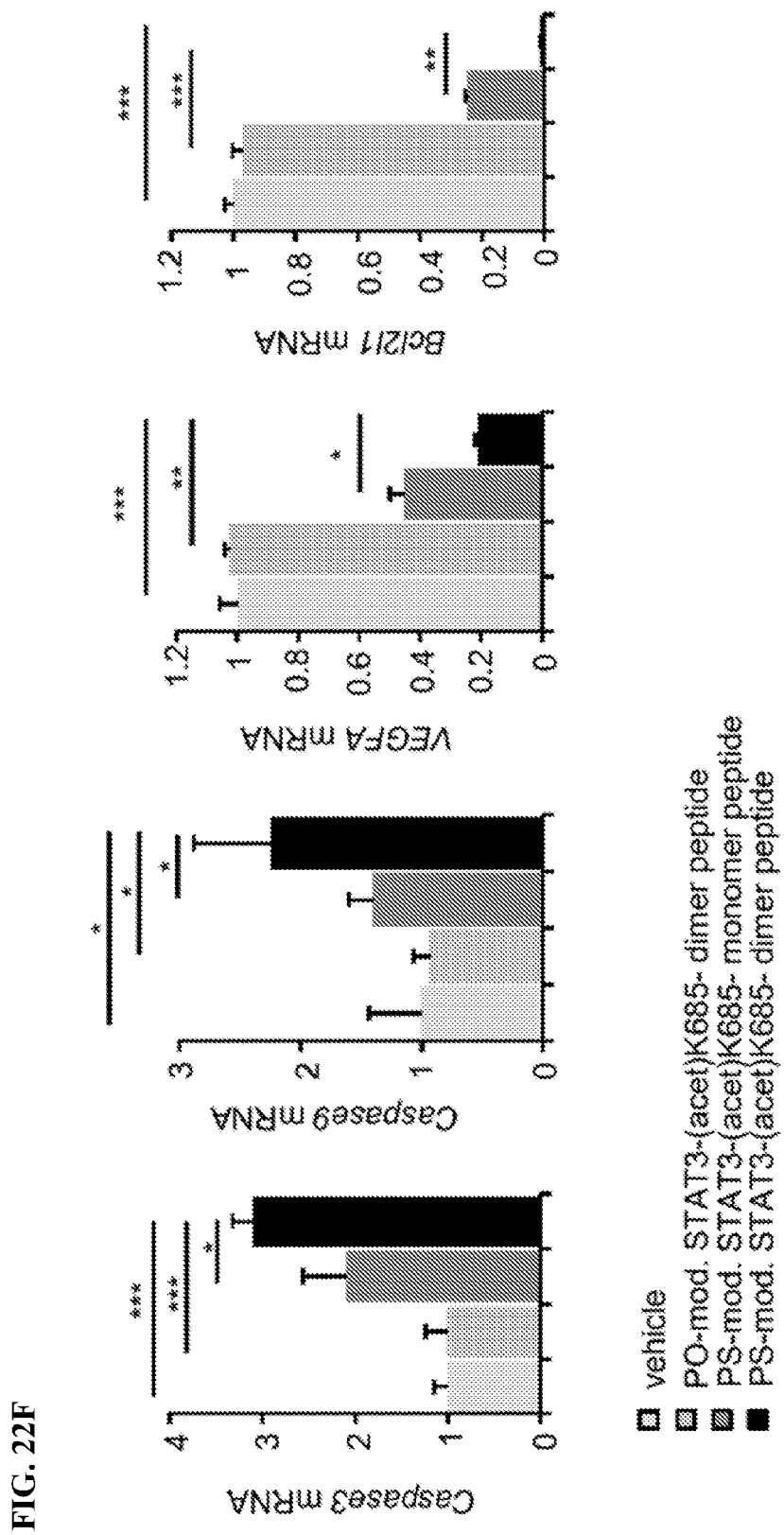

The dimerized PS-acetyl-STAT3 peptide more effectively downregulates pY705-STAT3 (upper panel) and induces p53 expression (lower panel) than its monomer counterpart, as analyzed by immunoprecipitation and Western blotting with tumor homogenates from the tumors in E (FIG. 22E). Applicants disclose qRT-PCR showing mRNA levels of STAT3-regulated pro-apoptotic and pro-survival genes in HCT116 tumor tissues treated with the indicated STAT3 peptides (FIG. 22F). The mRNA expression levels in the tumor tissues treated with control vehicle are set as 1. T-test; *; P<0.001; , P<0.01; *, P<0.05.

Figure 22G:
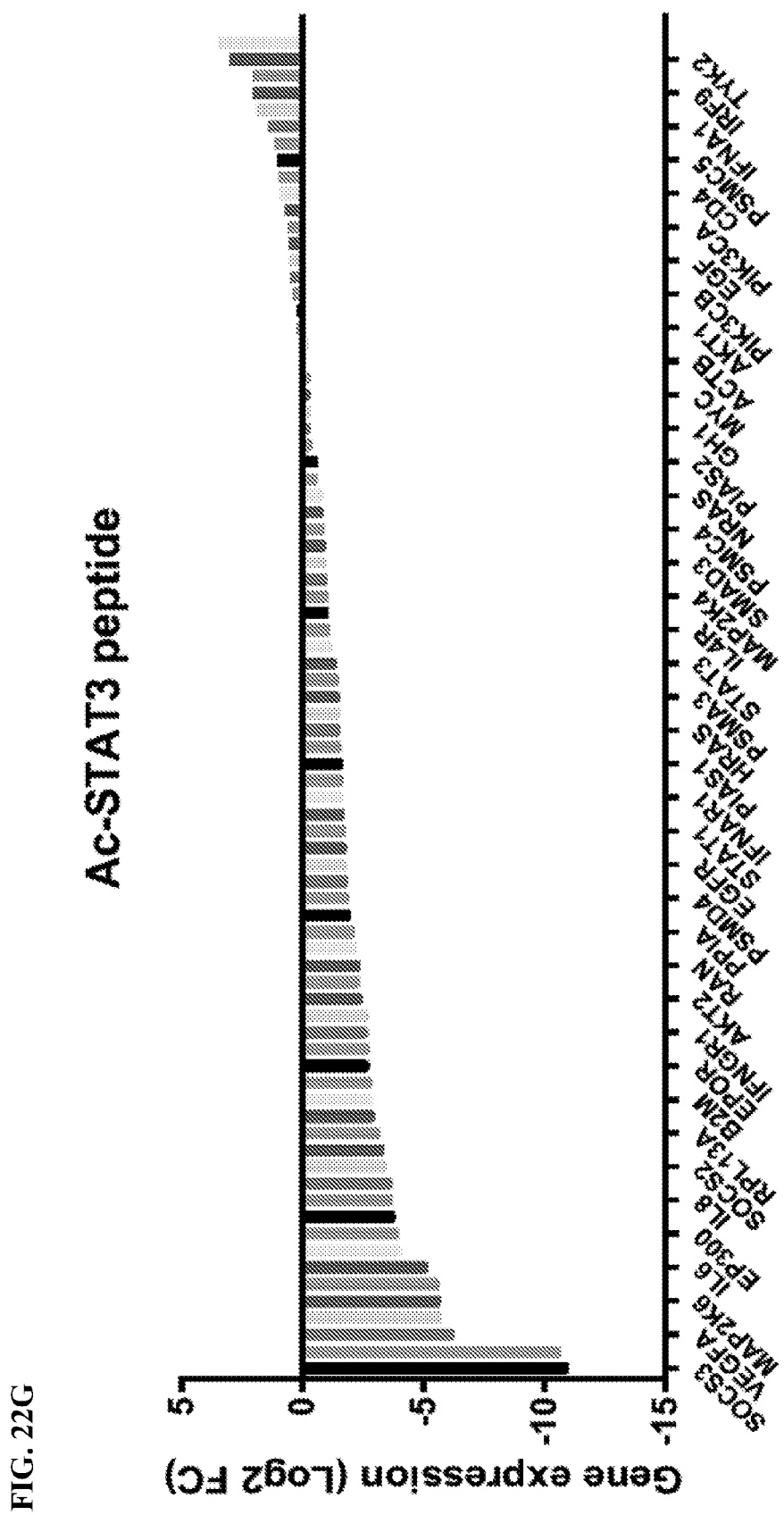
Figure 22H:
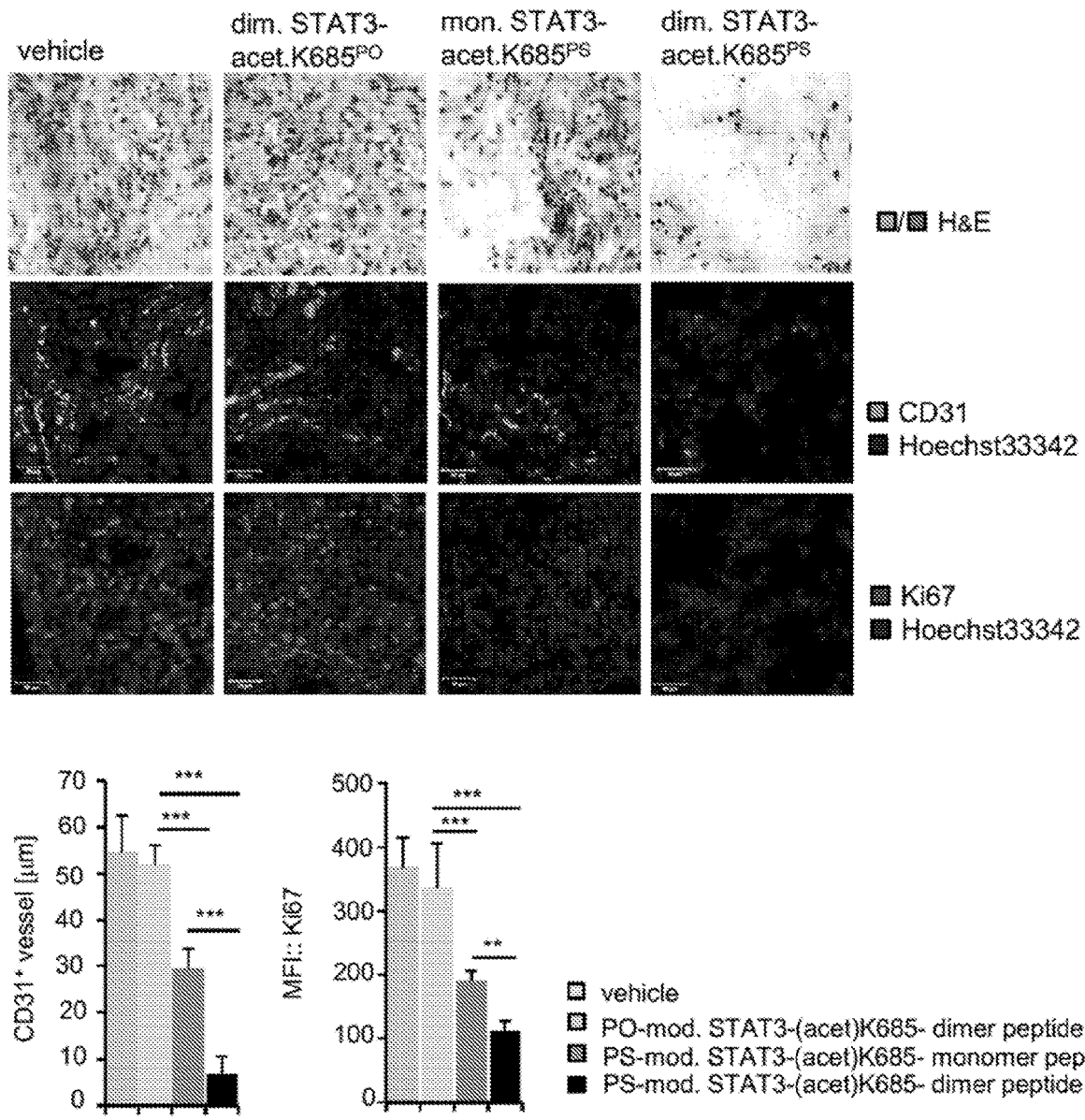

Applicants disclose on-target effects of the dimerized PS-acetyl-STAT3 peptide, assessed by qRT-PCR (FIG. 22G). The graph shows the differential expression of the downstream genes of JAK/STAT3 signaling pathway in the HCT116 tumor tissues treated with dimerized PS-acetyl-STAT3 peptide compared to vehicle. Applicants disclose immunohistochemical analyses of tumor sections from tumors shown in E, followed by confocal microscopy (FIG. 22H). The anti-tumor effects of dimerized PS-acetyl-STAT3 peptide are compared to its monomer counterpart. Images are representative of 3 tumors per experimental group. Scale bars: 50 µM (upper panel). Lower panels show the quantified Ki-67 protein levels as well as mean of vessel diameter (data include 5 fields of view per group).

Figure 23B:
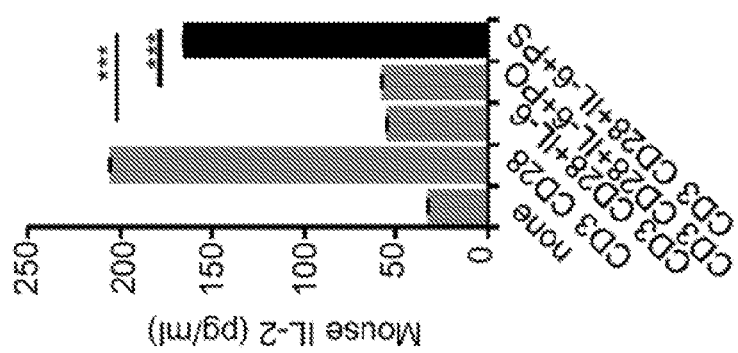
FIGS. 23A-23F: Systemic treatment with the PS-acetyl-STAT3 peptide reduces mouse melanoma lung metastasis and promotes CD8+ T cell activity.
Figure 23A:
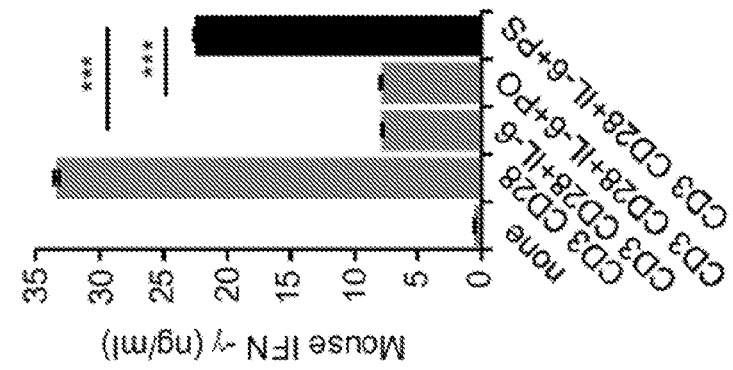
Figure 23A:
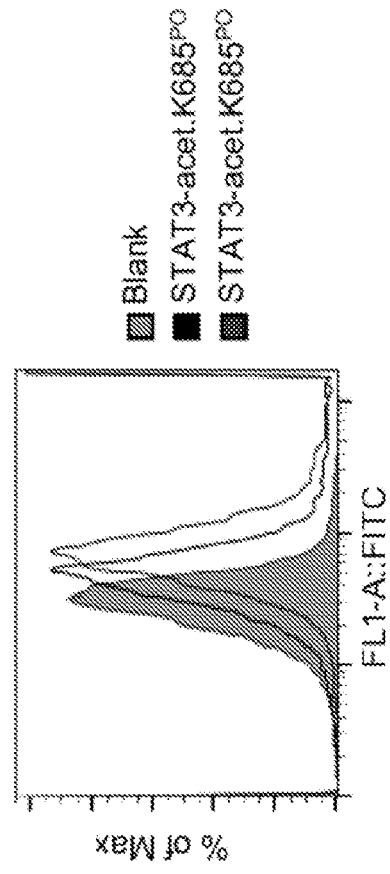

Example 13: Systemic Treatment with the PS-Acetyl-STAT3 Peptide Reducing Mouse Melanoma Lung Metastasis and Promotes CD8+ T Cell Activity Applicants disclose in vitro penetration of PS-acetyl-STAT3 peptide into CD8+ T cells, as assessed by flow cytometry (FIG. 23A). CD8+ T cells were isolated from $C_{57}BL/6$ mouse spleens. ELISA shows that treating splenic CD8+ T cells with the PS-acetyl-STAT3 peptide upregulates IFNγ and IL-2 expression, as expected from STAT3 inhibition (FIG. 23B). T-test; ***; P<0.001. Assays were done in triplicates.

Figure 23C:
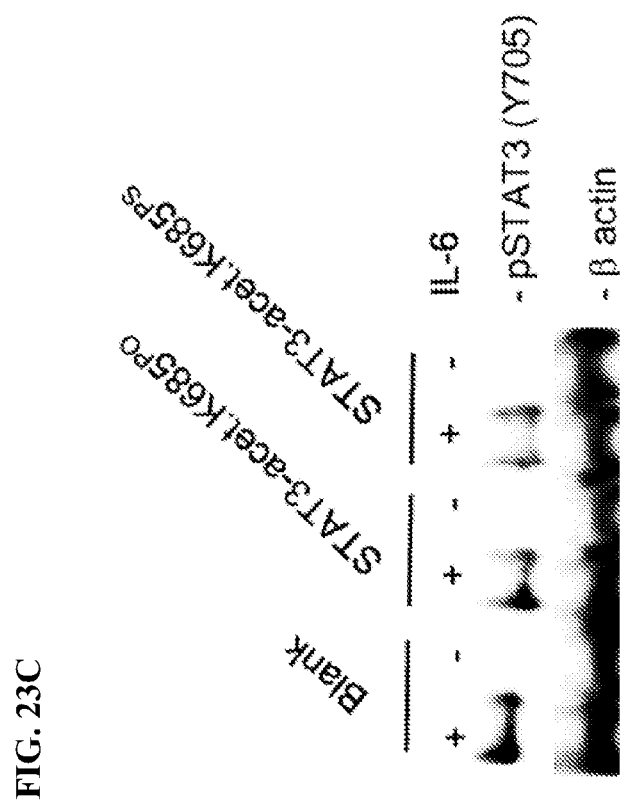
Figure 23D:
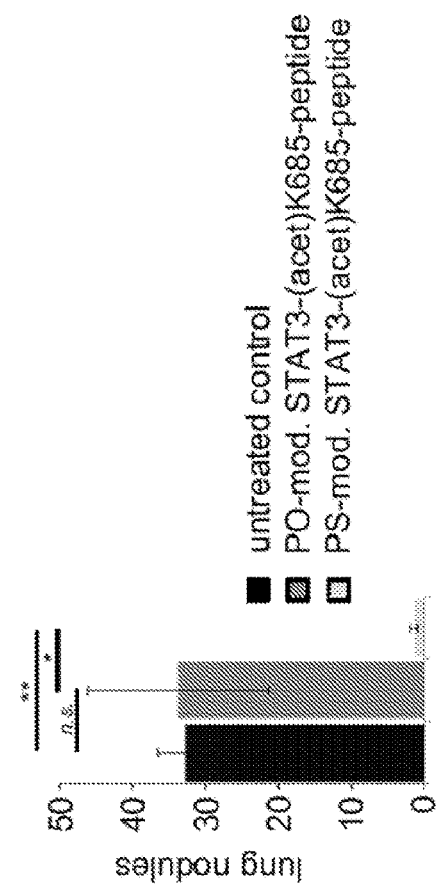
Figure 23D:
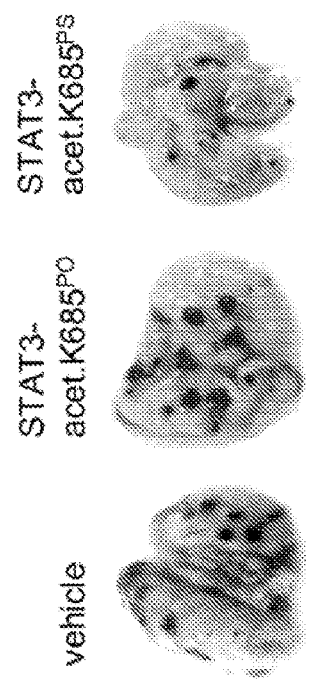

Applicants disclose downregulation of IL-6-induced pY705-STAT3 in splenic CD8+ T cells treated with PS-acetyl-STAT3 peptide compared to controls, as analyzed by Western blotting (FIG. 23C). The PS-acetyl-STAT3 peptide reduces B16 lung nodules in syngeneic mouse model compared with control treatments (FIG. 23D, left panel). Right panel shows numbers of lung nodules in mice treated with the indicated STAT3 peptides and vehicle (n=5). T-test; **, P<0.01; *, P<0.05. n.s: not significant.

Figure 23E:
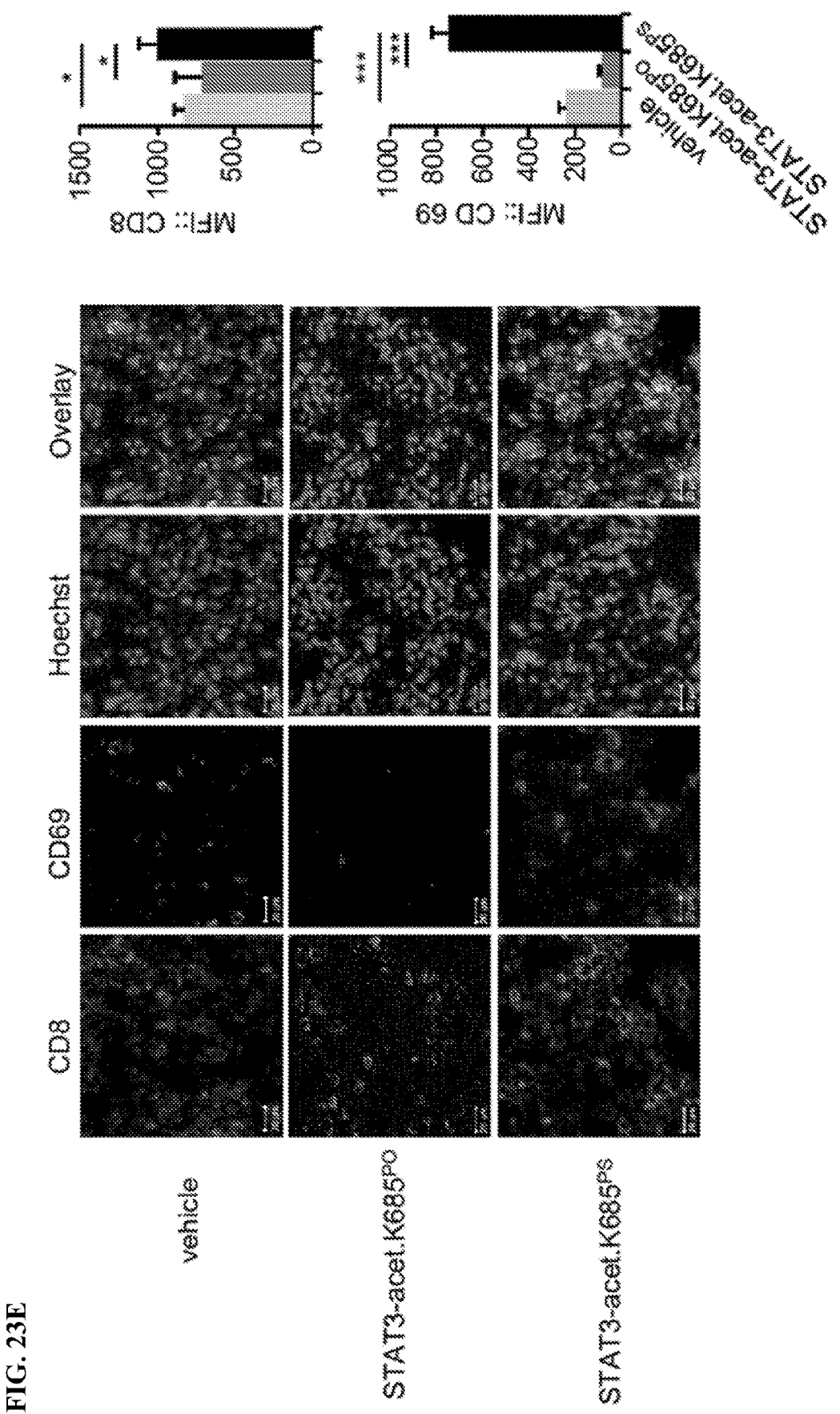
Figure 23F:
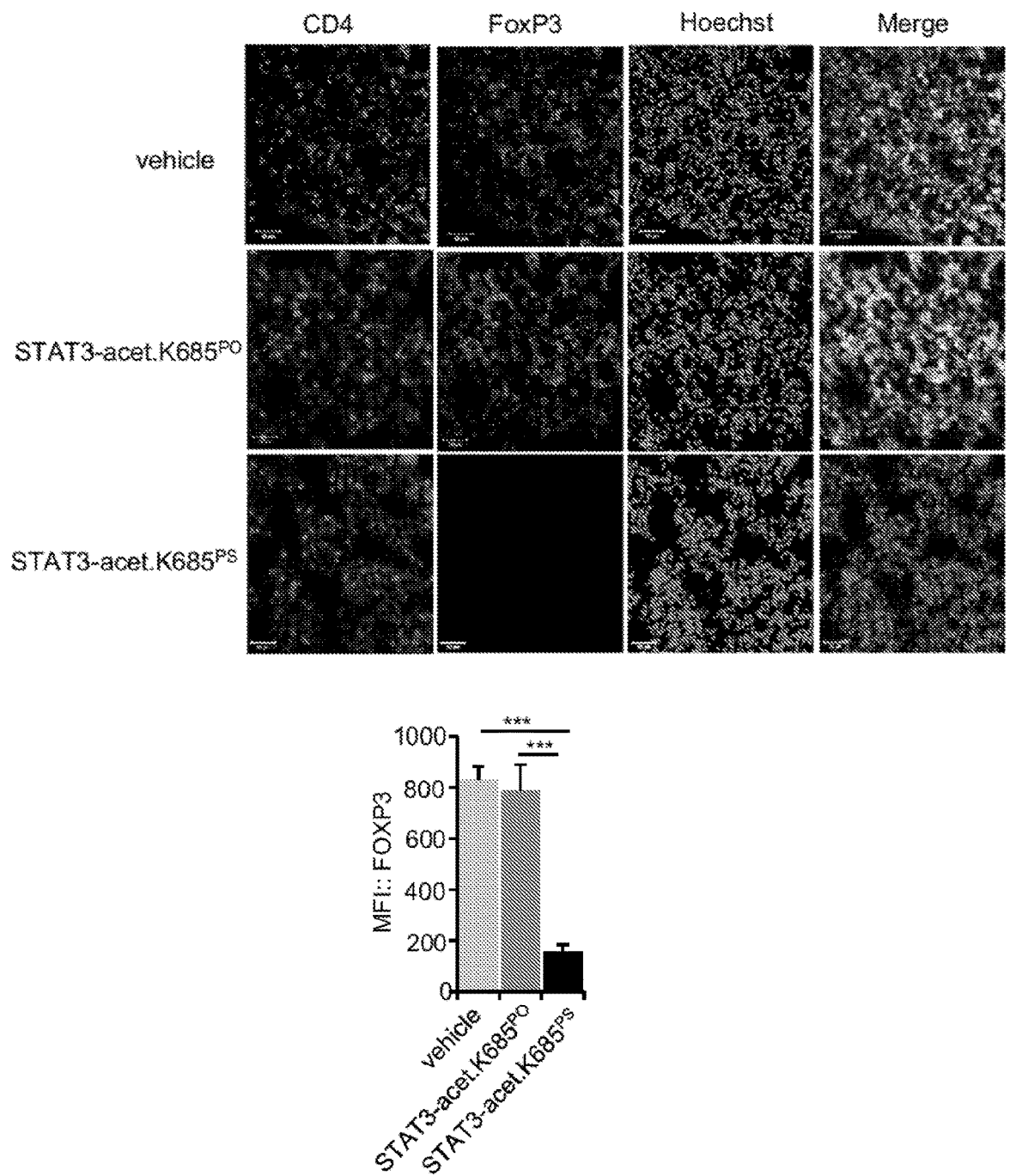

Applicants disclose immunochemical staining followed by confocal microscopy to detect the CD69+ tumor infiltrating CD8+ T cells and CD4+FoxP3+ T cell population in B16 lung nodules (same as in D) upon treatment with vehicle, PO- and PS-acetyl-STAT3 peptides (FIG. 23E and FIG. 23F). Images are representative of 3 lungs per experimental group. The graphs show the quantification of CD8, CD69 and FoxP3+ expression levels (data include 6 fields of view per group). SD is shown. ***; P<0.001; *, P<0.05.

Example 14: The PS-Acetyl-STAT3 Peptide Penetration and Bio-Functionality

Figure 24B:
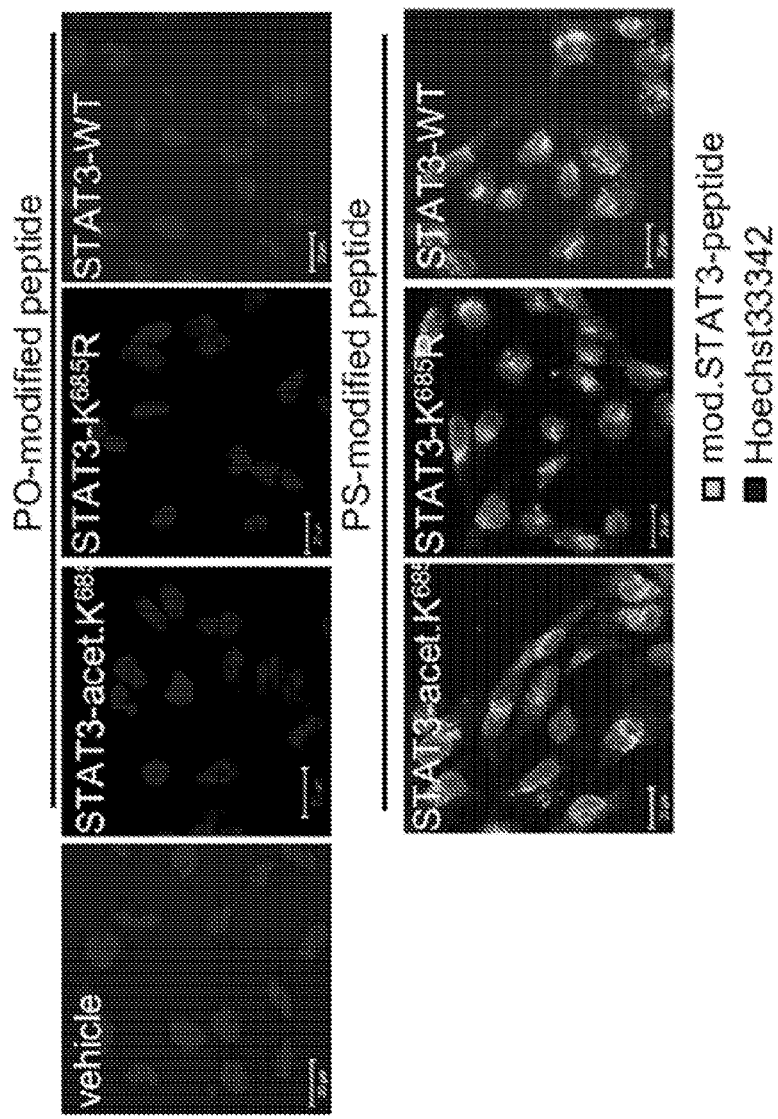
Figure 24C:
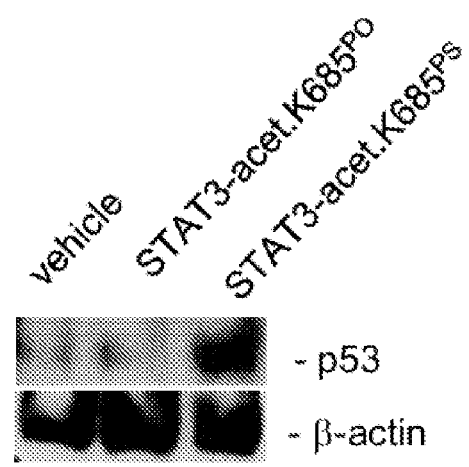

Applicants disclose structures of the modified STAT3 peptides (FIG. 24A). The PS-STAT3 peptides penetrate into HCT116 cancer cells, shown by immunofluorescence (FIG. 24B). Scale bars: 20 µm. Treatment with the PS-acetyl-STAT3 peptide induces p53 overexpression in HCT116 colon cancer cells, assessed by Western blotting (FIG. 24C).

Figure 25B:
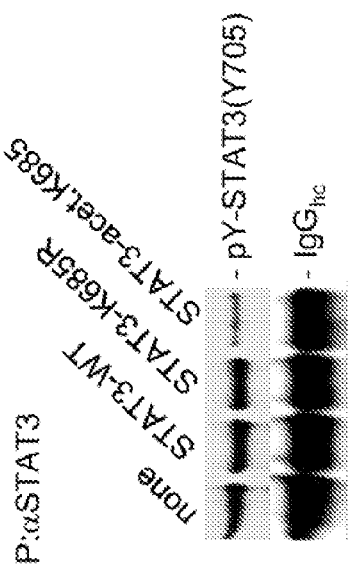
Figure 25A:
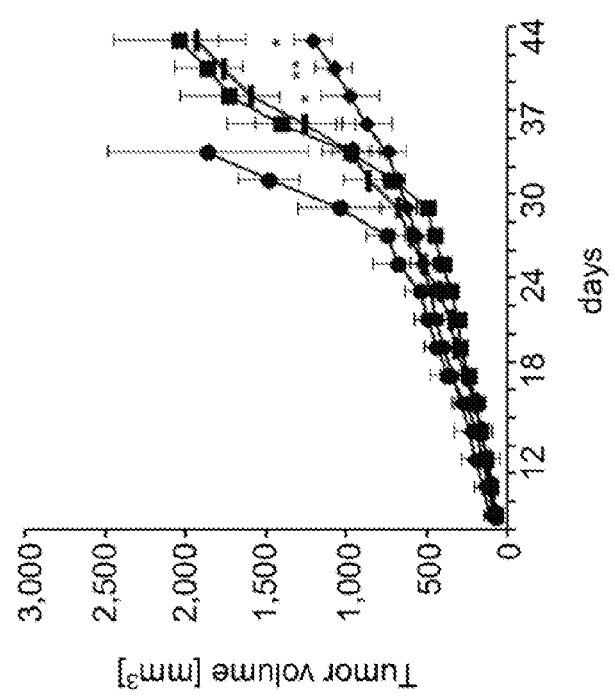

Example 15: PS-Acetyl-STAT3 Peptide Treatments Suppressing the Growth of HCT116 Colon Tumors Applicants disclose peritumoral treatment of subcutaneous (s.c.) HCT116 tumors in NSG mice with 18.940 µM PS-STAT3-WT, PS-STAT3-K685R or PS-STAT3-acet.-K685 peptides, starting 7 days after the mice were challenged with 5×106 HCT116 cells, n=4. Treatments were performed every day. SD is shown. *; P<0.001; , P<0.01; *, P<0.05. Western blotting shows STAT3 activity levels upon treatments with indicated acetyl-STAT3 peptides (FIG. 25B). mRNA levels of STAT3-downstream proliferation- and apoptosis-related genes as assessed by qRT-PCR using tumor homogenates prepared from tumors shown in A (FIG. 25C). The mRNA expression levels in the tumors treated with control vehicle are set as 1. T-test; *; P<0.001; , P<0.01; *, P<0.05.

Figure 25E:
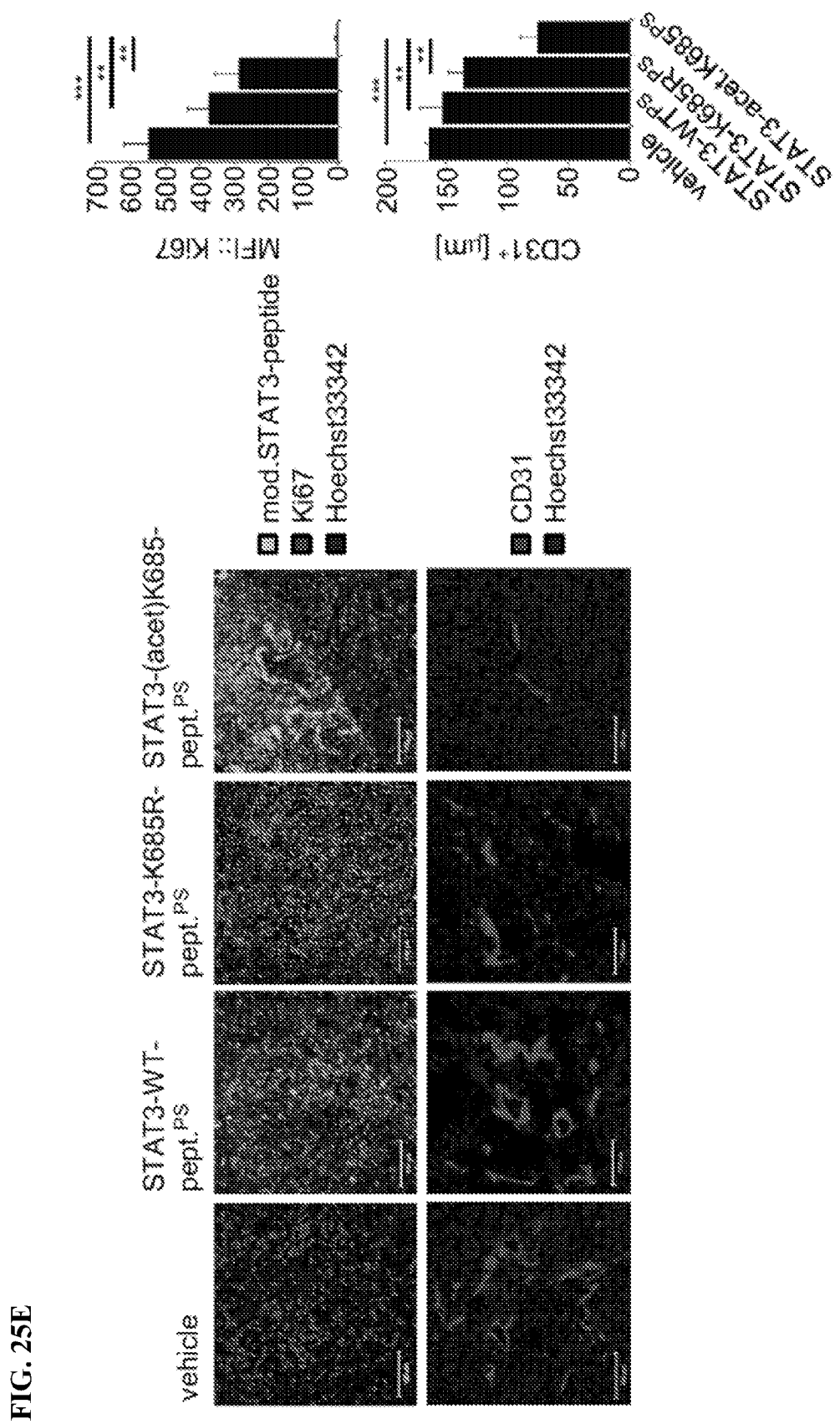

Applicants disclose upregulation of pro-apoptotic proteins, p53 and cl. caspase 3, in HCT 116 tumor homogenates from tumors shown in A, assessed by Western blotting (FIG. 25D). The PS-acetyl-STAT3 peptide penetrates into HCT116 tumors shown in A, and downregulates tumor Ki-67 and CD31 proteins, as visualized by confocal microscopy following immunohistochemical staining (FIG. 25E). Scale bar: 100 µm. Quantifications for Ki-67 and CD31 proteins in the treated tumors are shown in right panels. The graphs show the quantification of Ki67 and CD31 (data include 6 fields of view per group). SD is shown. P<0.01; *P<0.001.

Figure 26A:
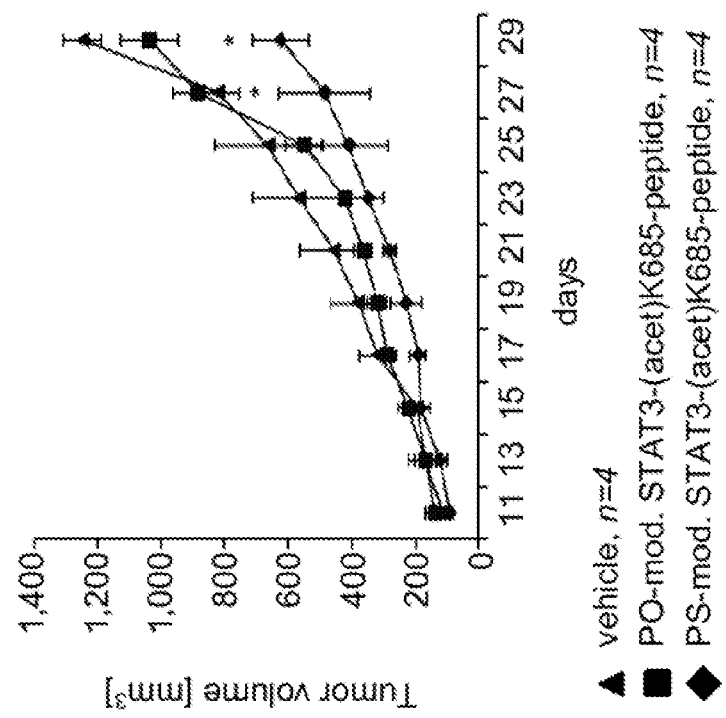
FIGS. 26A-26F: The non-phosphorothioated (PO) acetyl-STAT3 peptide does not show inhibitory effects on tumor growth.
Figure 26B:
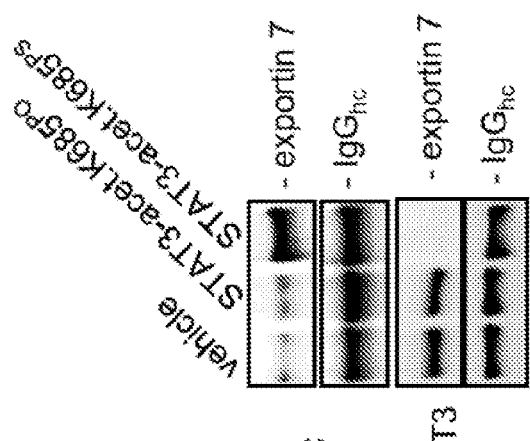
Figure 26C:
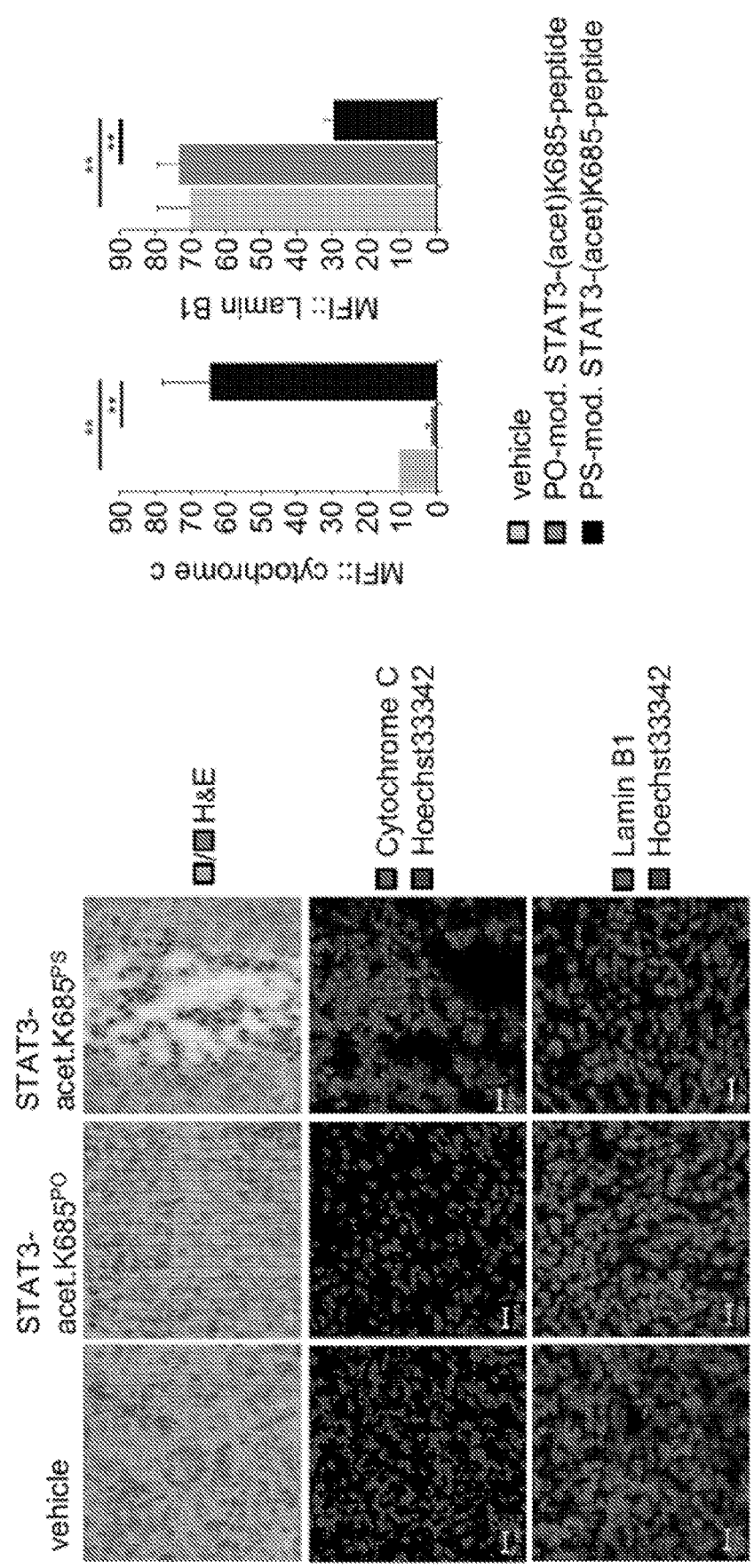

Example 16: The Non-Phosphorothioated (PO) Acetyl-STAT3 Peptide not Showing Inhibitory Effects on Tumor Growth The growth kinetic shows HCT116 tumors in NSG mice, treated with 18.940 µM PO- or PS-acetyl-STAT3 peptides locally every day (n=4) (FIG. 26A). SD is shown by asterisks. T-test; * P<0.05. PS-acetyl-STAT3 peptide binds to exportin 7, shown by immunoprecipitation and Western blotting using tumor homogenates prepared from tumors shown in A (FIG. 26B). Treatment with PS-acetyl-STAT3 peptide induces tumor apoptosis, indicated by H&E staining (FIG. 26C, upper panel) and Cytochrome C and Lamin B1 protein expression levels (FIG. 26C, middle and lower panels). Panels show representative images from 3 tumors from each experimental group. Scale bars: 20 μm. Quantifications for Cytochrome C and Lamin B1 are shown in the right panels (data include 5 fields of view per group). SD is shown. ** P<0.01.

Figure 26D:
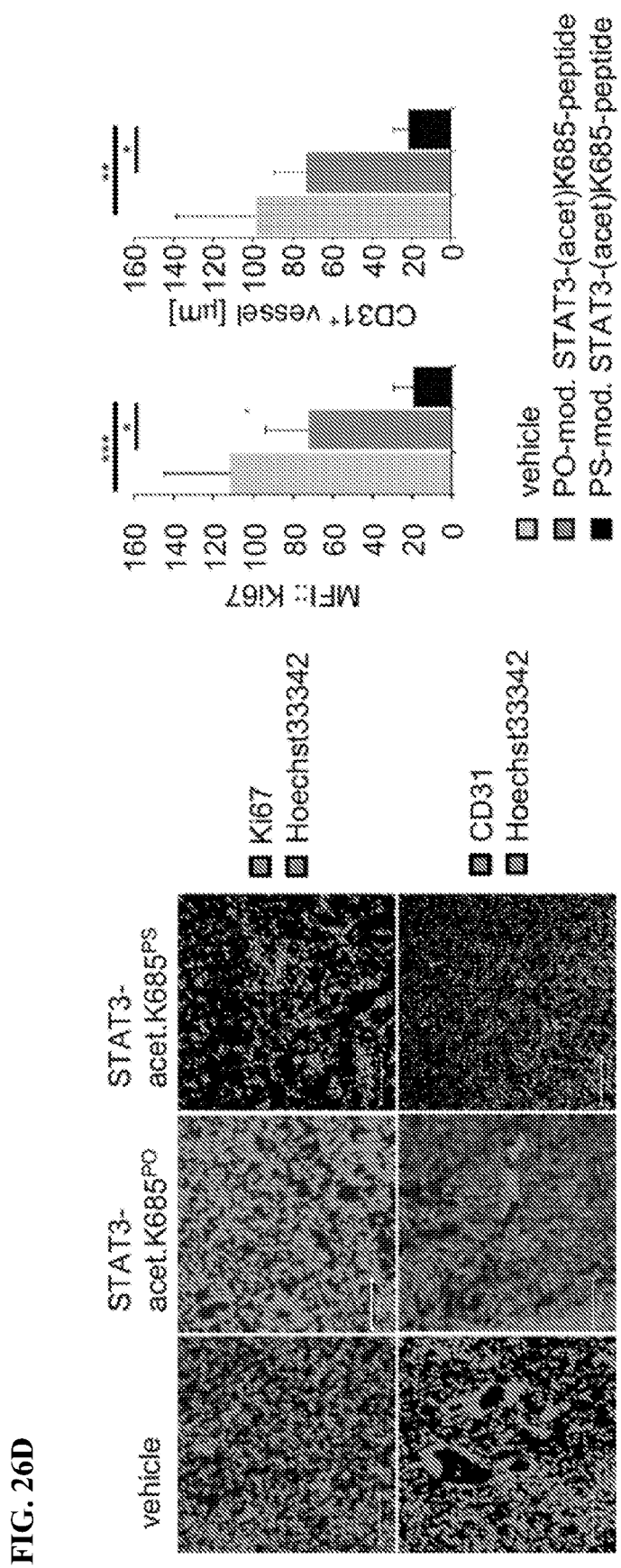

Applicants disclose Ki-67 and CD31 protein expression levels in tumors treated with vehicle, PO- or PS-acetyl-STAT3 peptide, as analyzed by confocal microscopy (FIG. 26D). Scale bar: 100 μm. Right panels show quantifications of Ki-67 protein levels and mean of vessel diameter (data include 5 fields of view per group). SD is shown. *; P<0.001; , P<0.01; *, P<0.05.

Figure 26E:
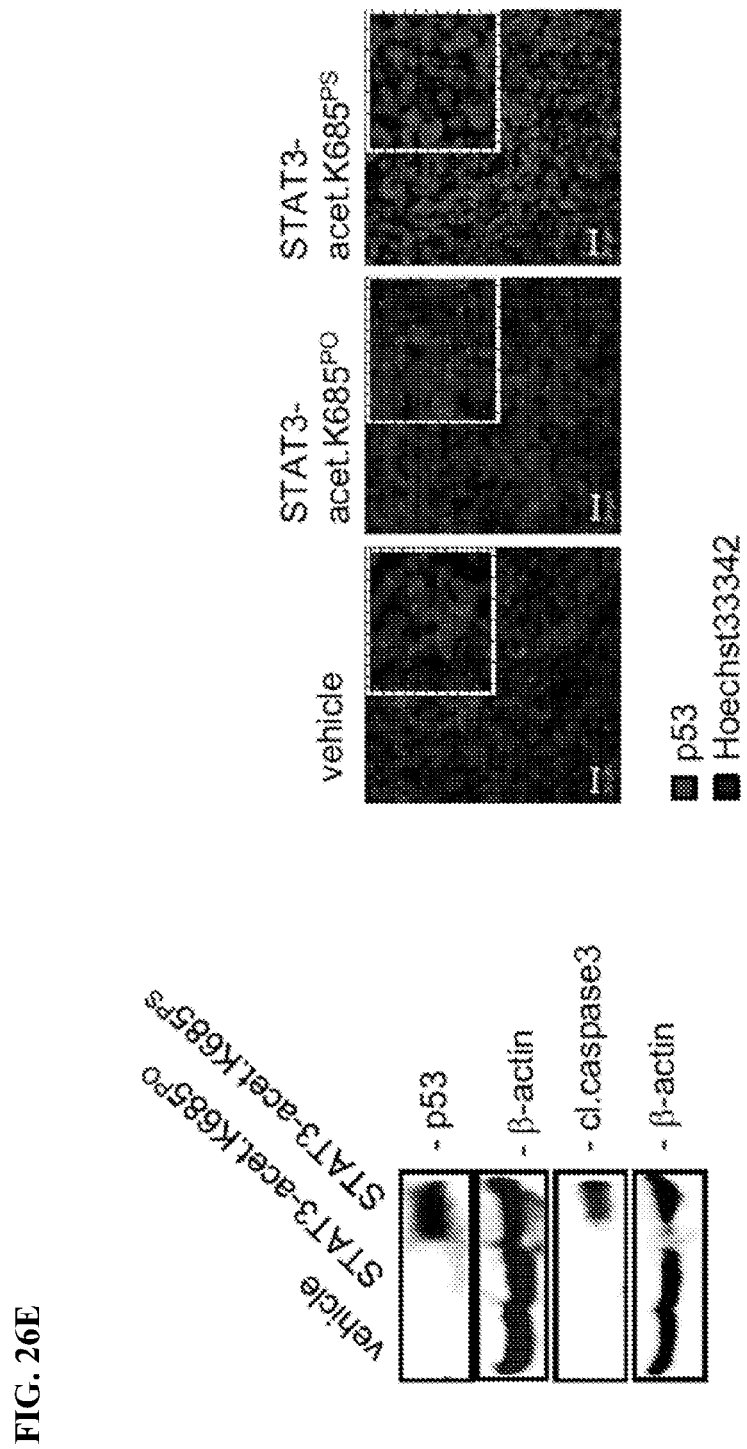
Figure 26F:
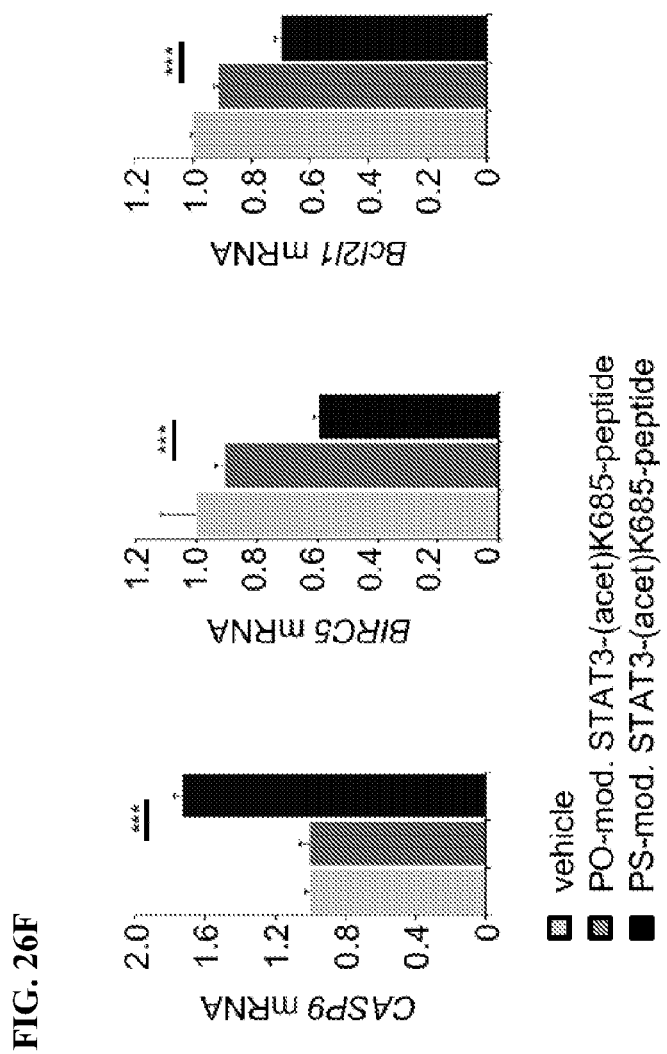

Applicants disclose Western blotting showing p53 and cl. caspase 3 overexpression in the tumors shown in A (FIG. 26E, left panel). The increased p53 protein expression in HCT116 tumors treated with the PS-acetyl-STAT3 peptide is shown by immunohistochemical staining followed by confocal microscopy imaging. The images represent tumor sections from 3 tumors per experimental group (n=3). Scales; 20 μm. mRNA levels for CASP9, BIRC5 and Bcl2L1 in the same tumor tissues described above are assessed by qRT-PCR (FIG. 26F). The mRNA levels of the same genes from tumors without peptide treatments are set as 1. SD is shown. ***P<0.001.

Example 17: JAK-STAT3 Signaling Array

Figure 27:
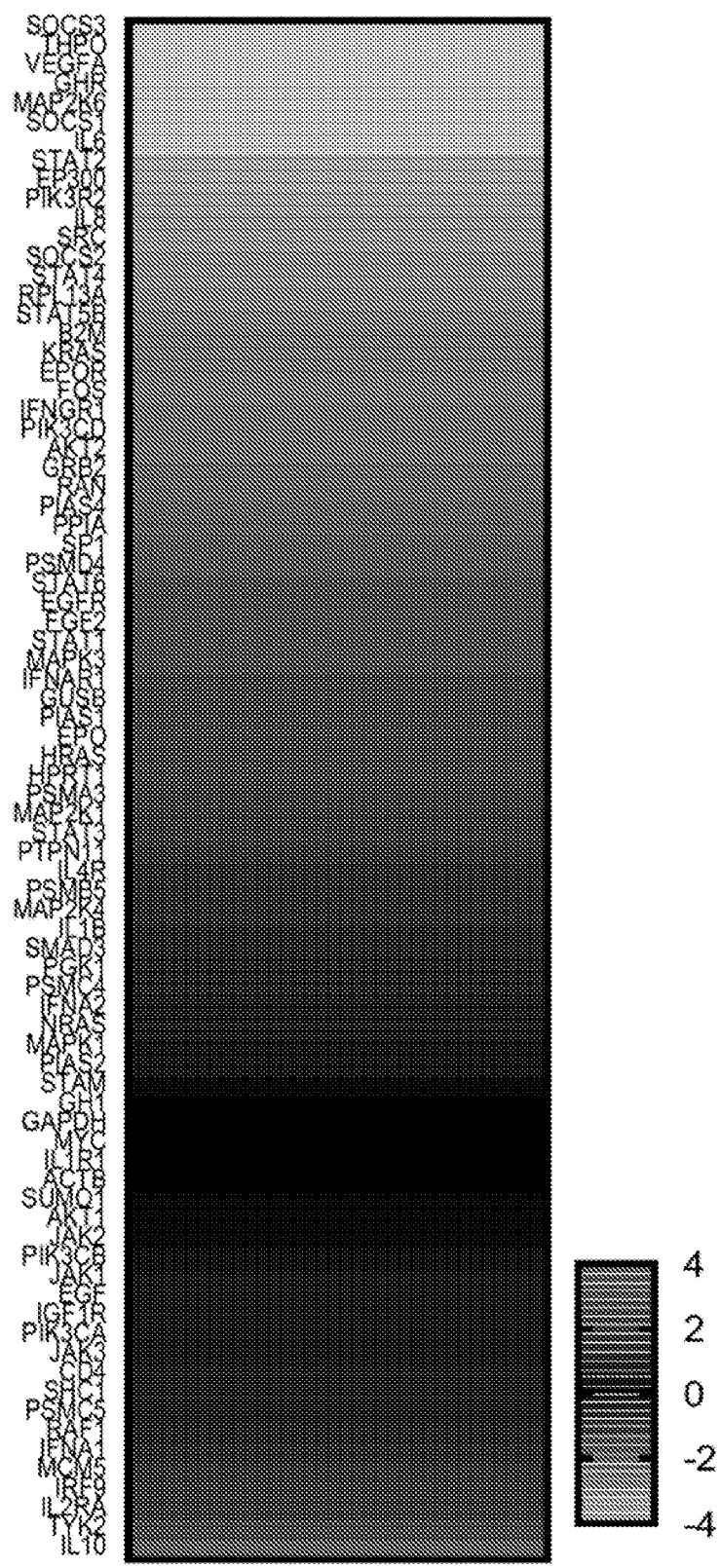
FIG. 27: JAK-STAT3 Signaling Array. A heat map of genes in the "JAK-STAT3 pathway" gene set. The color spectrum from top to bottom indicates low to high expression of JAK-STAT3 downstream genes upon treatment with the dimerized PS acetyl-STAT3 peptide compared to vehicle.

Applicants disclose a heat map of genes in the "JAK-STAT3 pathway" gene set (FIG. 27). The color spectrum from top to bottom indicates low to high expression of JAK-STAT3 downstream genes upon treatment with the dimerized PS acetyl-STAT3 peptide compared to vehicle.

Figure 28B:
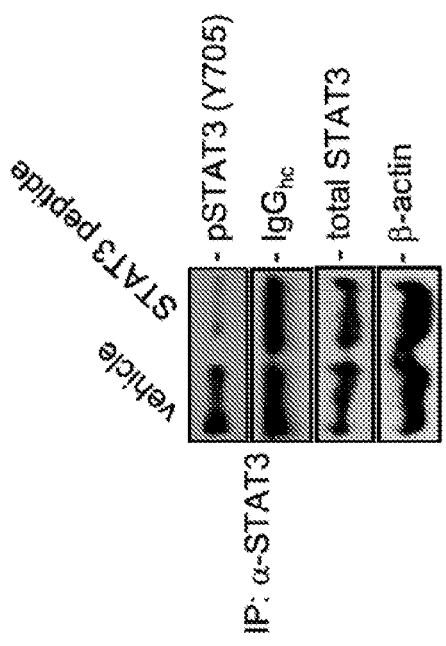
FIGS. 28A-28D: Systemic treatments with the PS acetyl-STAT3 peptides suppress paclitaxel-resistant TNBC xenograft tumor growth.
Figure 28A:
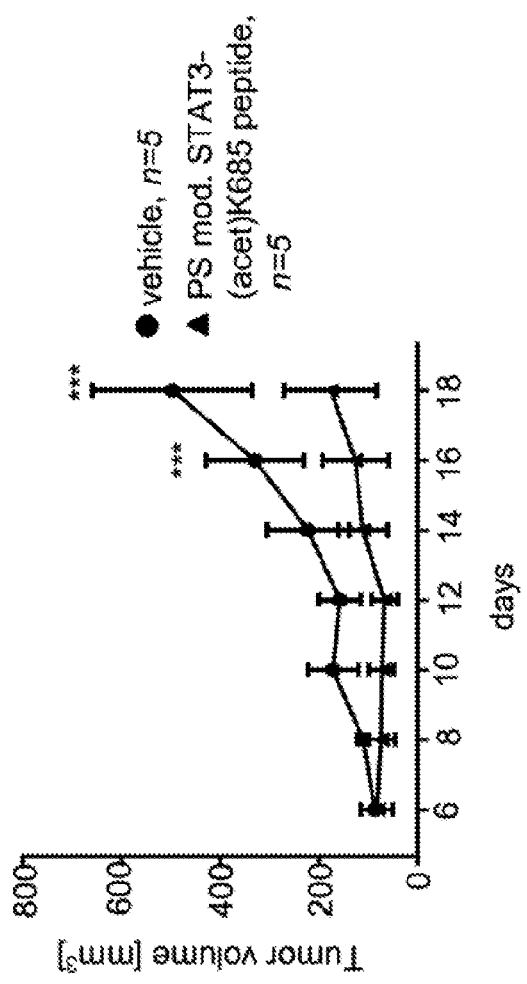

Example 18: Systemic Treatments with the PS Acetyl-STAT3 Peptides Suppressing Paclitaxel-Resistant TNBC Xenograft Tumor Growth Applicants disclose growth kinetics of paclitaxel-resistant MDA-MB-231 TNBC tumors in NSG mice (FIG. 28A). Tumors were systemically treated with vehicle (HBSS−/−) and the PS-acetyl-STAT3 peptide every other day. Applicants also disclose downregulation of STAT3 phosphorylation by the PS-acetyl-STAT3 peptides in TNBC tumors shown in A (FIG. 28B).

Figure 28C:
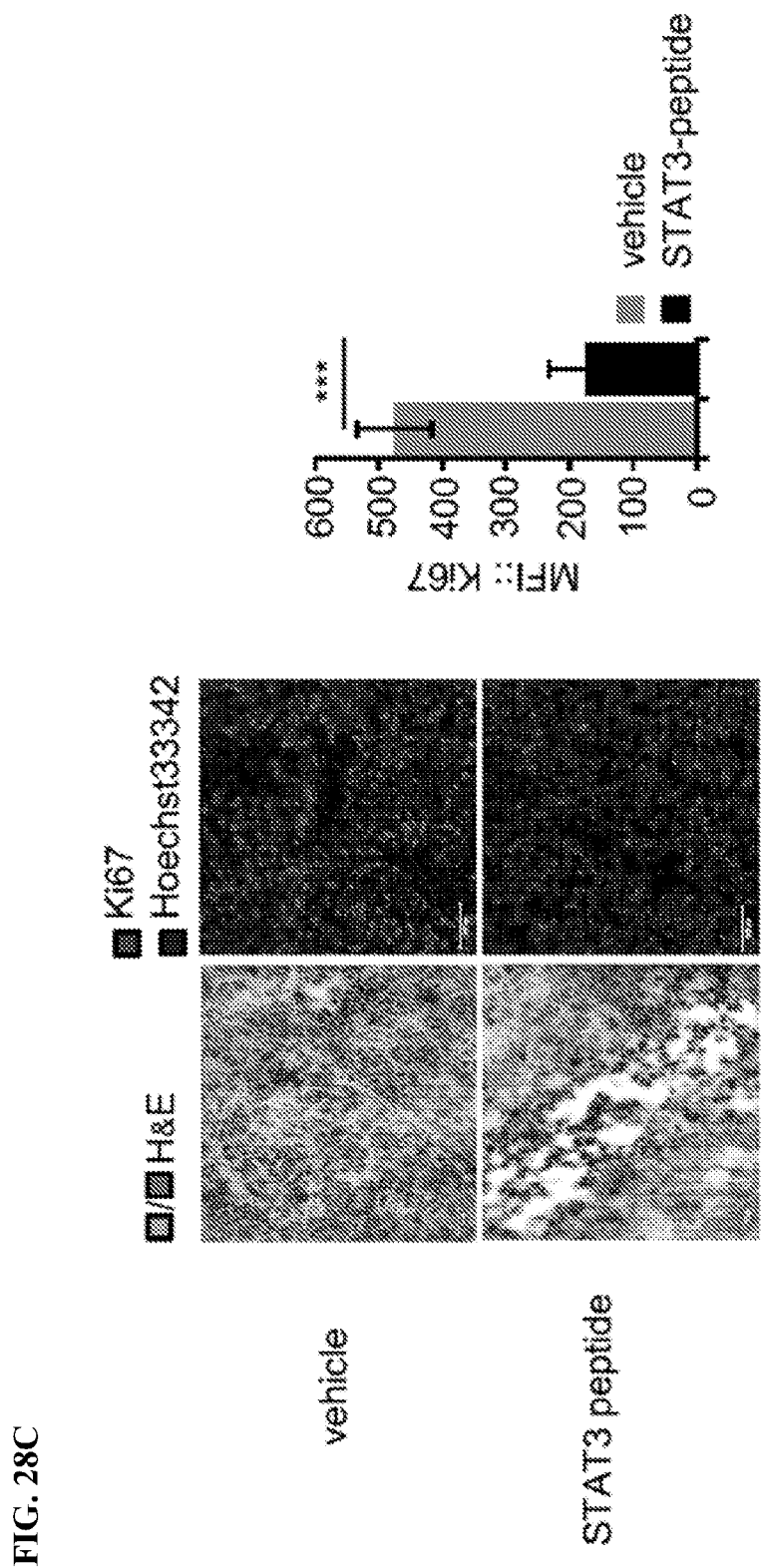
Figure 28D:
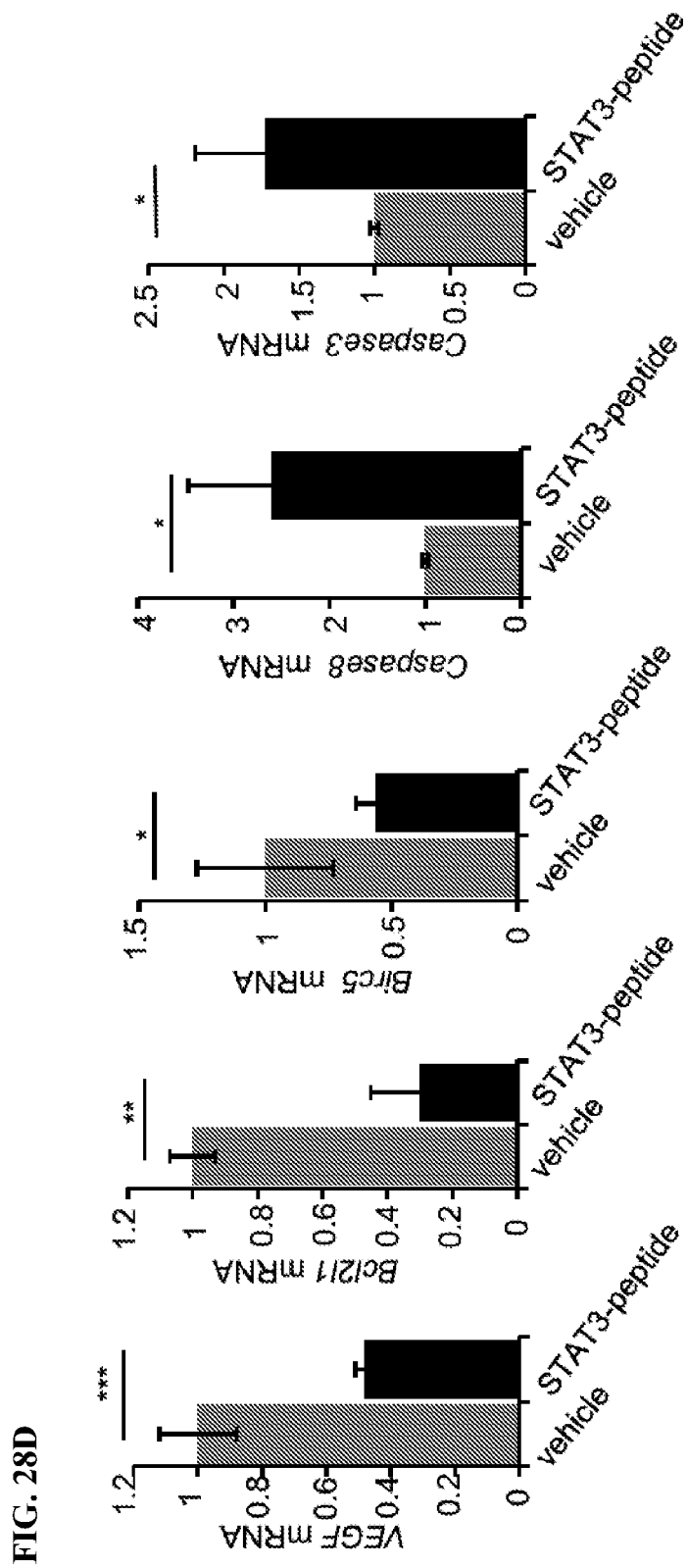

Confocal images of indicated immunochemical staining show apoptotic and proliferation degrees in tumor tissues shown in A (FIG. 28C, left panels). Images representatively show tissue sections from 3 tumors per experimental group. Scales; 50 and 100 μm. Right panel is the quantification of Ki67 expression levels (data include 6 fields of view per group). SD is shown. *; P<0.001. qRT-PCR shows mRNA levels of the indicated proliferation and apoptosis genes in the TNBC tumor tissues (FIG. 28D). The mRNA expression levels in the tumor tissues from the mice without peptide treatment are set as 1. SD is shown *, P<0.001; **, P<0.01; *, P<0.05.

Figure 29A:
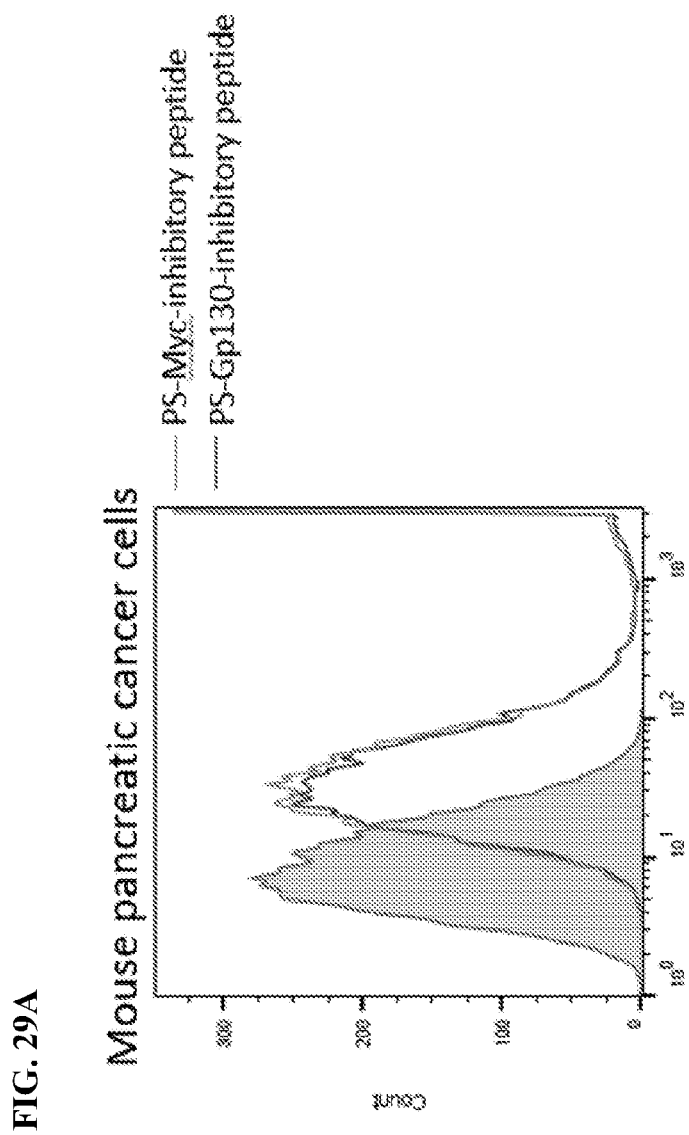
FIGS. 29A-29B: Combination treatment of cell-penetrating Gp130-inhibitory peptide (i.e., Gp130 peptide) and c-MYC-inhibitory peptide (i.e., c-MYC binding peptide) (SEQ ID NO:10) suppresses tumor growth in a syngeneic mouse model of pancreatic cancer.
Figure 29B:
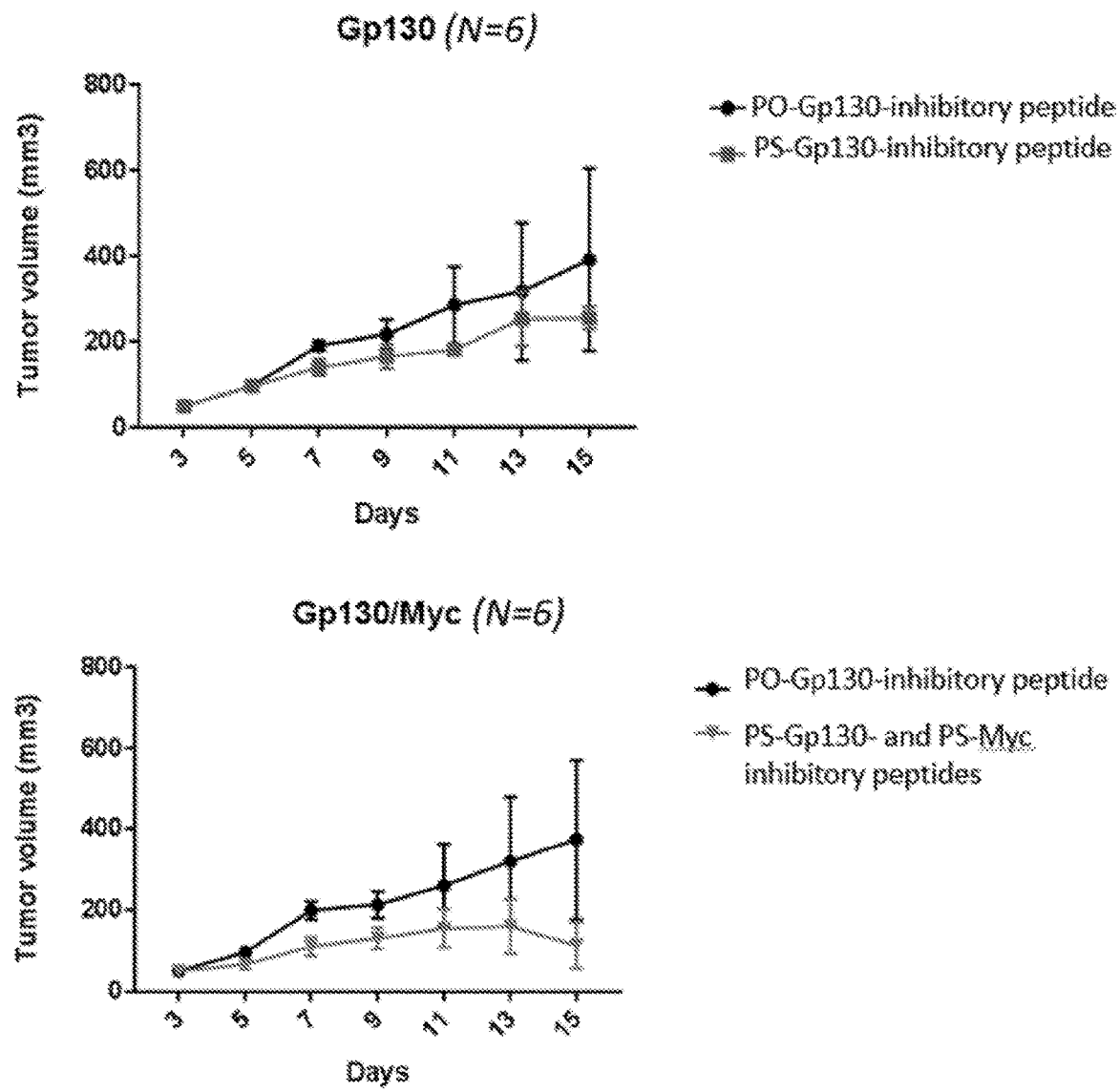

Example 19: Combination Treatment of Cell-Penetrating GP130- and C-MYC-Inhibitory Peptides Suppressing Tumor Growth in a Syngeneic Mouse Model of Pancreatic Cancer Applicants disclose cell penetration of FITC-PS-GP130-inhibitory peptide and PS-c-MYC-inhibitory peptide (SEQ ID NO:10) in W76964 (mouse pancreatic cancer cell line) cells (FIG. 29A). c-MYC-inhibitory peptide directly binds to c-MYC protein and prevents the full-length c-MYC from interacting with MAX and thus blocking MYC-MAX dimerization. $1\times10^6$ cells were incubated with 10 μg of PS-GP130- or PS-c-MYC-peptide for 2 hours at 37° C. The efficiency of cell penetration was determined by flow cytometry. W76964 cells were engrafted in $C_{57}BL/6$ mice to generate tumors (FIG. 29B). After tumor size reached approximately 80 $mm^3$, PO-Gp130 or PS-GP130 was mixed with PS-c-MYC-inhibitory peptide (1:1 ratio) to treat mice systemically (i.v.) at 20 μg every other day. Tumor size was measured by a caliber. Tumor volume was calculated (V= (L×W×W)), where V is tumor volume, W is tumor width, L is tumor length. When some tumors start to reach 600 $mm^3$, all groups of mice were euthanized at the same time using protocols approved by IACUC of City of Hope. N=6 as indicated.

Figure 30:
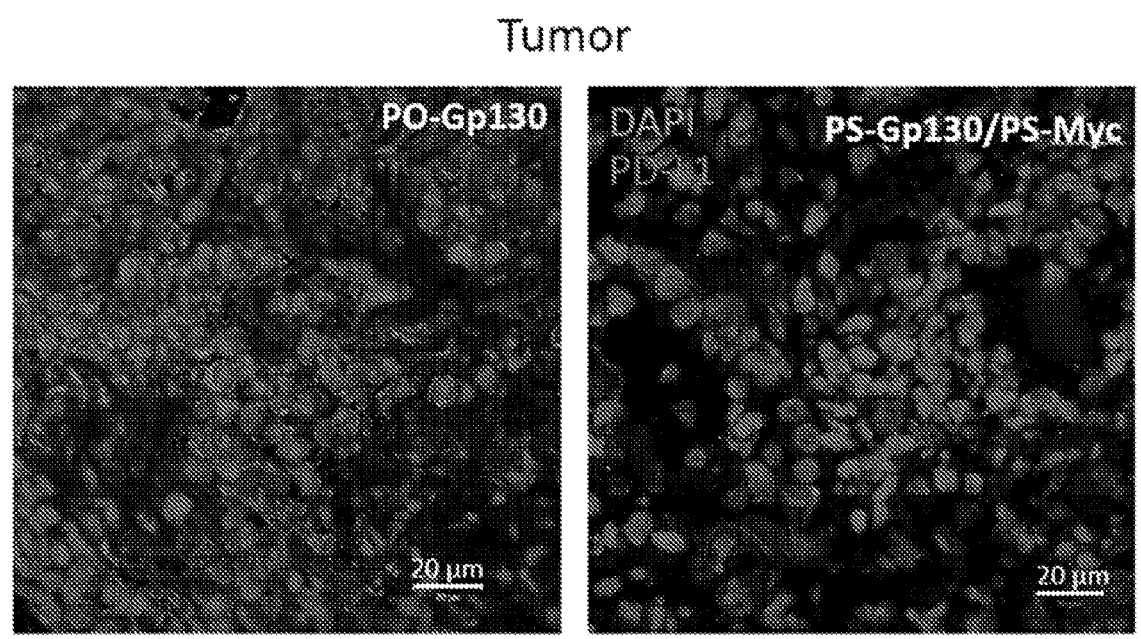
FIG. 30: Combination treatment of cell-penetrating Gp130 and c-MYC synthetic peptides (i.e., c-MYC binding peptides) decreases PD-L1 expression in syngeneic mouse models of pancreatic cancer. PD-L1 expression level was examined by immunohistochemistry in tissue sections of tumors from mice treated with indicated peptides. PD-L1 was presented as red fluorescence and nuclei were visualized by DAPI staining. White bar presents 20 μm.

Example 20: Combination Treatment of Cell-Penetrating Gp130 and C-MYC Synthetic Peptides Decreasing Pd-L1 Expression in Syngeneic Mouse Models of Pancreatic Cancer PD-L1 was presented as red fluorescence and nuclei were visualized by DAPI staining (FIG. 30). White bar presents 20 μm.

Figure 31A:
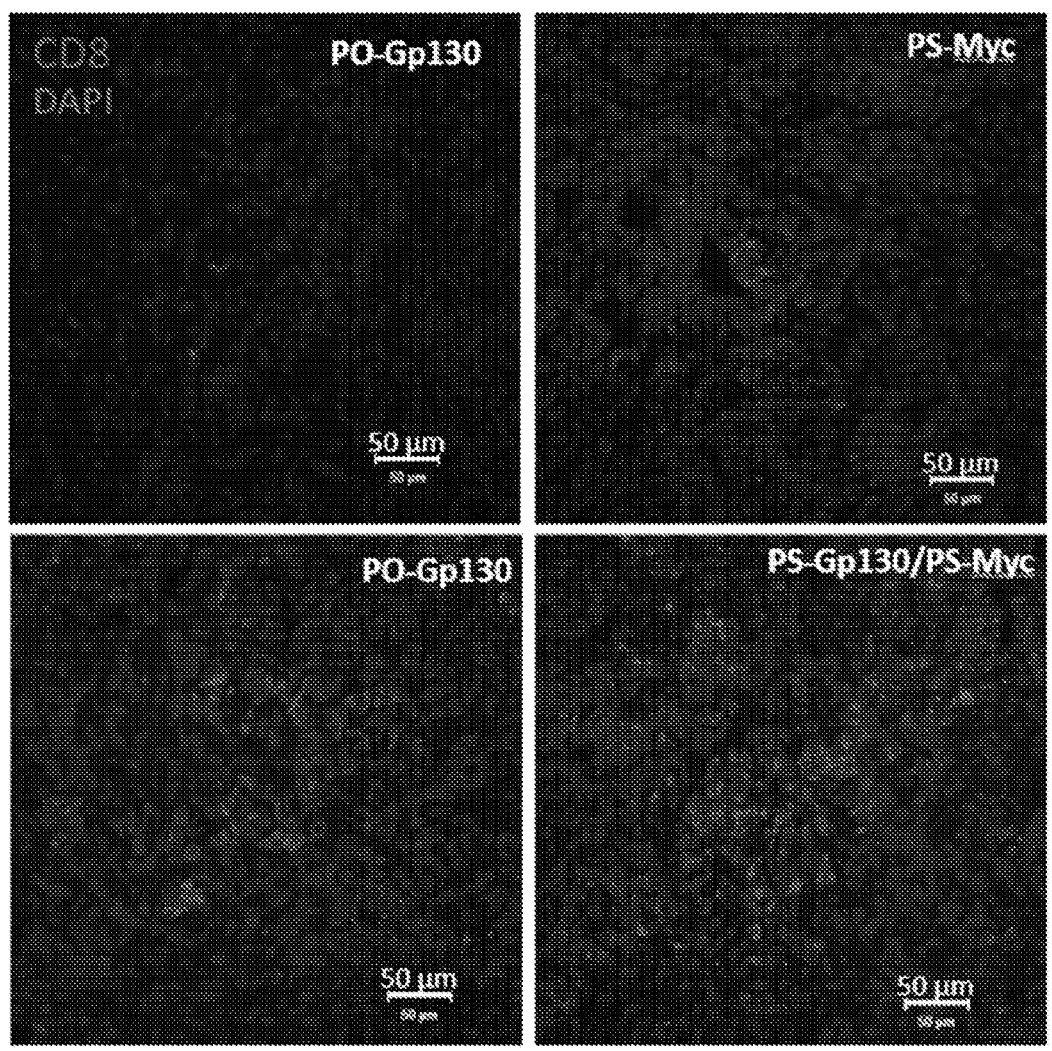
FIGS. 31A-31B: Combination treatment of cell-penetrating Gp130 and c-MYC synthetic peptides increases tumor infiltrated CD8+ T cells and IFN-γ in syngeneic mouse models of pancreatic cancer. Tumor infiltrating CD8+ T cells (FIG. 31A), IFN-γ and FITC-conjugated peptides (FIG. 31B) were detected by immunohistochemistry using tumor tissue sections prepared from mice treated with indicated peptides. White bar in (FIG. 31A) presents 50 μm and in (FIG. 31B) presents 20 μm.
Figure 31B:
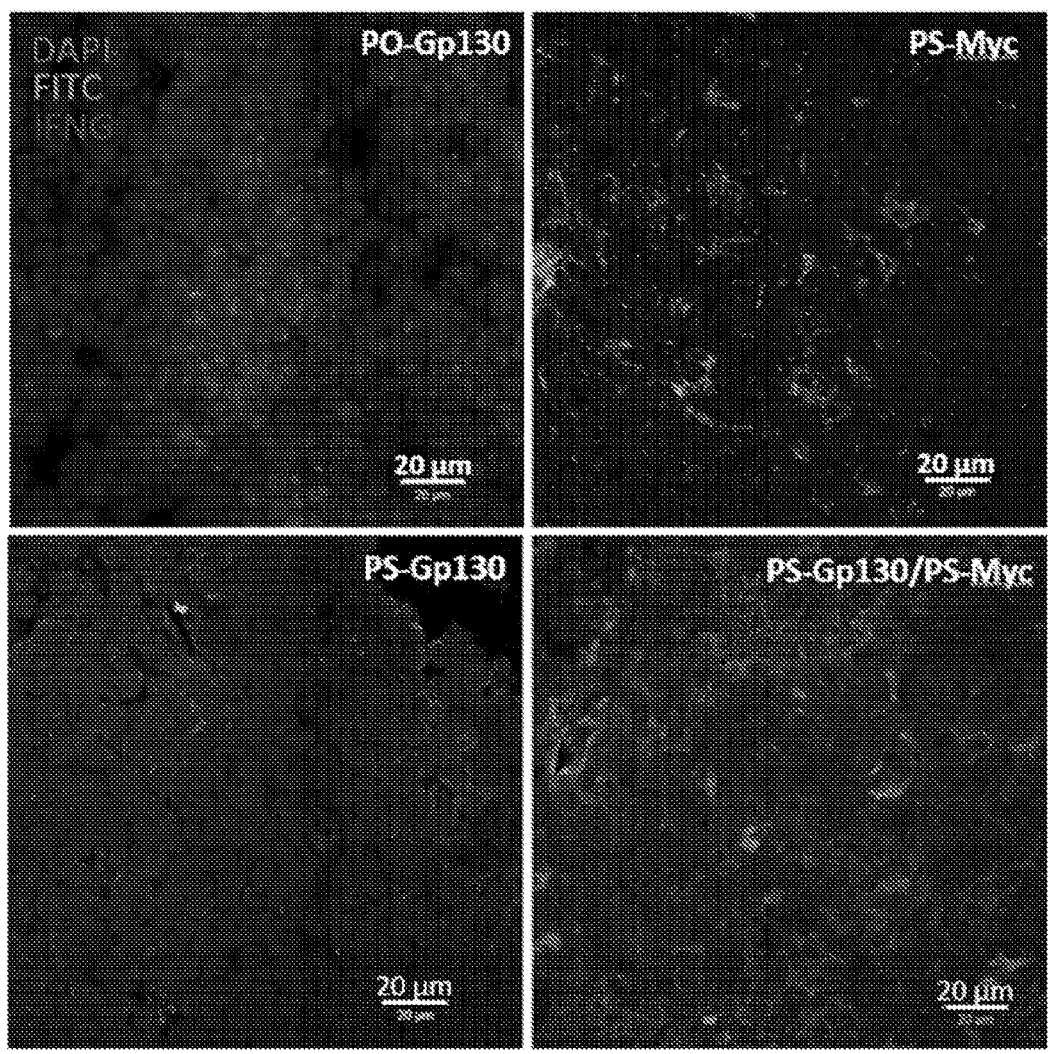

Example 21: Combination Treatment of Cell-Penetrating Gp130 and C-MYC Synthetic Peptides Increasing Tumor Infiltrated Cd8+ T Cells and IFN-γ in Syngeneic Mouse Models of Pancreatic Cancer Tumor infiltrating CD8+ T cells (FIG. 31A), IFN-γ and FITC-conjugated peptides (FIG. 31B) were detected by immunohistochemistry using tumor tissue sections prepared from mice treated with indicated peptides. White bar in (FIG. 31A) presents 50 μm and in (FIG. 31B) presents 20 μm.

REFERENCES

Herrmann, A., Nachaev, S., Lahtz, C., Armstrong, B., Kowolik, C., Kortylewski, M., Jove, R., and Hua, Y. (2014). STAT3 nuclear egress requires exportin 7 via engaging lysine acetylation. MOJ Cell Sci Report 1(1): 00004. DOI: 10.15406/mojcsr.2014.01.00004

INFORMAL SEQUENCE LISTING

STAT3 polypeptide (SEQ ID NO:1):
MAQWNQLQQLDTRYLEQLHQLYSDSFPMELRQFLAPWIESQDWAYAASKESHATL
VFHNLLGEIDQQYSRFLQESNVLYQHNLRRIKQFLQSRYLEKPMEIARIVARCLWEES
RLLQTAATAAQQGGQANHPTAAVVTEKQQMLEQHLQDVRKRVQDLEQKMKVVEN -continued

INFORMAL SEQUENCE LISTING

```
LQDDFDFNYKTLKSQGDMQDLNGNNQSVTRQKMQQLEQMLTALDQMIRRSIVSELA
GLLSAMEYVQKTLTDEELADWKRRQQIACIGGPPNICLDRLENWITSLAESQLQTRQ
QIKKLEELQQKVSYKGDPIVQHRPMLEERIVELFRNLMKSAFVVERQPCMPMHPDRP
LVIKTGVQFTTKVRLLVKFPELNYQLKIKVCIDKDSGDVAALRGSRKFNILGTNTKV
MNMEESNNGSLSAEFKHLTLREQRCGNGGRANCDASLIVTEELHLITFETEVYHQGL
KIDLETHSLPVVVISNICQMPNAWASILWYNMLTNNPKNVNFFTKPPIGTWDQVAEV
LSWQFSSTTKRGLSIEQLTTLAEKLLGPGVNYSGCQITWAKFCKENMAGKGFSFWV
WLDNIIDLVKKYILALWNEGYIIVIGFISKERERAILSTKPPGTFLLRFSESSKEGGVTFT
WVEKDISGKTQIQSVEPYTKQQLNNMSFAEIIMGYKIMDATNILVSPLVYLYPDIPKE
EAFGKYCRPESQEHPEADPGSAAPYLKTKFICVTPTTCSNTIDLPMSPRTLDSLMQFG
NNGEGAEPSAGGQFESLTFDMELTSECATSPM gp130 polypeptide (SEQ ID NO:2):
MLTLQTWLVQALFIFLTTESTGELLDPCGYISPESPVVQLHSNFTAVCVLKEKCMDYF
HVNANYIVWKTNHFTIPKEQYTIINRTASSVTFTDIASLNIQLTCNILTFGQLEQNVYGI
TIISGLPPEKPKNLSCIVNEGKKMRCEWDGGRETHLETNFTLKSEWATHKFADCKAK
RDTPTSCTVDYSTVYFVNIEVWVEAENALGKVTSDHINFDPVYKVKPNPPHNLSVIN
SEELSSILKLTWTNPSIKSVIILKYNIQYRTKDASTWSQIPPEDTASTRSSFTVQDLKPF
TEYVFRIRCMKEDGKGYWSDWSEEASGITYEDRPSKAPSFWYKIDPSHTQGYRTVQ
LVWKTLPPFEANGKILDYEVTLTRWKSHLQNYTVNATKLTVNLTNDRYLATLTVRN
LVGKSDAAVLTIPACDFQATHPVMDLKAFPKDNMLWVEWTTPRESVKKYILEWCV
LSDKAPCITDWQQEDGTVHRTYLRGNLAESKCYLITVTPVYADGPGSPESIKAYLKQ
APPSKGPTVRTKKVGKNEAVLEWDQLPVDVQNGFIRNYTIFYRTIIGNETAVNVDSS
HTEYTLSSLTSDTLYMVRMAAYTDEGGKDGPEFTFTTPKFAQGEIEAIVVPVCLAFLL
TTLLGVLFCFNKRDLIKKHIWPNVPDPSKSHIAQWSPHTPPRHNFNSKDQMYSDGNF
TDVSVVEIEANDKKPFPEDLKSLDLFKKEKINTEGHSSGIGGSSCMSSSRPSISSSDENE
SSQNTSSTVQYSTVVHSGYRHQVPSVQVFSRSESTQPLLDSEERPEDLQLVDHVDGG
DGILPRQQYFKQNCSQHESSPDISHFERSKQVSSVNEEDFVRLKQQISDHISQSCGSGQ
MKMFQEVSAADAFGPGTEGQVERFETVGMEAATDEGMPKSYLPQTVRQGGYMPQ STAT3 polypeptide acetylated at lysine 685 (SEQ ID NO: 3):
PDIPKEEAFG(acet)K₆₈₅YCRPESQEHPC gp130 polypeptide phosphorylated at tyrosine 767 (SEQ ID NO: 4):
VHSGpYRHQVPS (the lower case p indicates phosphorylation of the adjacent tyrosine)

Exportin 7 polypeptide (SEQ ID NO: 5):
MADHVQSLAQLENLCKQLYETTDTTTRLQAEKALVEFTNSPDCLSKCQLLLERGSSS
YSQLLAATCLTKLVSRTNNPLPLEQRIDIRNYVLNYLATRPKLATFVTQALIQLYARI
TKLGWFDCQKDDYVFRNAITDVTRFLQDSVEYCIIGVTILSQLTNEINQADTTHPLTK
HRKIASSFRDSSLFDIFTLSCNLLKQASGKNLNLNDESQHGLLMQLLKLTHNCLNFDF
IGTSTDESSDDLCTVQIPTSWRSAFLDSSTLQLFFDLYHSIPPSFSPLVLSCLVQIASVRR
SLFNNAERAKFLSHLVDGVKRILENPQSLSDPNNYHEFCRLLARLKSNYQLGELVKV
ENYPEVIRLIANFTVTSLQHWEFAPNSVHYLLSLWQRLAASVPYVKATEPHMLETYT
PEVTKAYITSRLESVHIILRDGLEDPLEDTGLVQQQLDQLSTIGRCEYEKTCALLVQLF
DQSAQSYQELLQSASASPMDIAVQEGRLTWLVYIIGAVIGGRVSFASTDEQDAMDGE
LVCRVLQLMNLTDSRLAQAGNEKLELAMLSFFEQFRKIYIGDQVQKSSKLYRRLSEV
LGLNDETMVLSVFIGKIITNLKYWGRCEPITSKTLQLLNDLSIGYSSVRKLVKLSAVQ
FMLNNHTSEHFSFLGINNQSNLTDMRCRTTFYTALGRLLMVDLGEDEDQYEQFMLP
LTAAFEAVAQMFSTNSFNEQEAKRTLVGLVRDLRGIAFAFNAKTSFMMLFEWIYPSY
MPILQRAIELWYHDPACTTPVLKLMAELVHNRSQRLQFDVSSPNGILLFRETSKMIT
MYGNRILTLGEVPKDQVYALKLKGISICFSMLKAALSGSYVNFGVFRLYGDDALDN
ALQTFIKLLLSIPHSDLLDYPKLSQSYYSLLEVLTQDHMNFIASLEPHVIMYILSSISEG
LTALDTMVCTGCCSCLDHIVTYLFKQLSRSTKKRTTPLNQESDRFLHIMQQHPEMIQ
QMLSVLNIIIFEDCRNQWSMSRPLLGLILLNEKYFSDLRNSIVNSQPPEKQQAMHLCF
ENLMEGIERNLLTKNRDRFTQNLSAFRREVNDSMKNSTYGVNSNDMMS Wild-type STAT3 polypeptide (SEQ ID NO: 6):
PDIPKEEAFGK₆₈₅YCRPESQEHPC STAT3 polypeptide with arginine mutation at position 685 (SEQ ID NO: 7):
PDIPKEEAFGR₆₈₅YCRPESQEHPC gp130 polypeptide phosphorylated at tyrosine 905 (SEQ ID NO: 8):
MPKSpYLPQTV (the lower case p indicates phosphorylation of the adjacent tyrosine)

gp130 polypeptide phosphorylated at tyrosine 915 (SEQ ID NO: 9):
RQGGpYMPQ (the lower case p indicates phosphorylation of the adjacent tyrosine)

c-MYC binding polypeptide (SEQ ID NO: 10):
KNDTHQQDIDDLK c-MYC polypeptide (SEQ ID NO: 11):
MDFFRVVENQQPPATMPLNVSFTNRNYDLDYDSVQPYFYCDEEENFYQQQQQSELQ
PPAPSEDIWKKFELLPTPPLSPSRRSGLCSPSYVAVTPFSLRGDNDGGGGSFSTADQLE
MVTELLGGDMVNQSFICDPDDETFIKNIIIQDCMWSGFSAAAKLVSEKLASYQAARK
DSGSPNPARGHSVCSTSSLYLQDLSAAASECIDPVVFPYPLNDSSSPKSCASQDSSAF
```

INFORMAL SEQUENCE LISTING

```
SPSSDSLLSSTESSPQGSPEPLVLHEETPPTTSSDSEEEQEDEEEIDVVSVEKRQAPGKR
SESGSPSAGGHSKPPHSPLVLKRCHVSTHQHNYAAPPSTRKDYPAAKRVKLDSVRVL
RQISNNRKCTSPRSSDTEENVKRRTHNVLERQRRNELKRSFFALRDQIPELENNEKAP
KVVILKKATAYILSVQAEEQKLISEEDLLRKRREQLKHKLEQLRNSCA

MAX polypeptide (SEQ ID NO: 12):
MSDNDDIEVESDEEQPRFQSAADKRAHHNALERKRRDHIKDSFHSLRDSVPSLQGEK
ASRAQILDKATEYIQYMRRKNHTHQQDIDDLKRQNALLEQQVRALEKARSSAQLQT
NYPSSDNSLYTNAKGSTISAFDGGSDSSSESEPEEPQSRKKLRMEAS ssDNA 20 mer 1 (SEQ ID NO: 13):
TCCATGAGCTTCCTGATGCT ssDNA 20 mer 2 (SEQ ID NO: 14):
AGCATCAGGAAGCTCATGGA
```

P EMBODIMENTS

P embodiment 1. A nucleic acid-peptide conjugate comprising:
(i) a non-cell penetrating peptide;
(ii) a phosphorothioate nucleic acid; and
(iii) a chemical linker attaching said phosphorothioate nucleic acid to the C-terminus of said non-cell penetrating peptide;
wherein said phosphorothioate nucleic acid enhances intracellular delivery of said non-cell penetrating peptide.

P embodiment 2. The conjugate of P embodiment 1, wherein said non-cell penetrating peptide is about 5, 10, 15, 20 or 25 amino acids in length.

P embodiment 3. The conjugate of one of P embodiments 1-2, wherein said non-cell penetrating peptide is at least 5 amino acids in length.

P embodiment 4. The conjugate of one of P embodiments 1-3, wherein said non-cell penetrating peptide is about 8 amino acids in length.

P embodiment 5. The conjugate of one of P embodiments 1-3, wherein said non-cell penetrating peptide is about 10 amino acids in length.

P embodiment 6. The conjugate of one of P embodiments 1-3, wherein said non-cell penetrating peptide is about 11 amino acids in length.

P embodiment 7. The conjugate of one of P embodiments 1-6, wherein said non-cell penetrating peptide is about 22 amino acids in length.

P embodiment 8. The conjugate of one of P embodiments 1-8, wherein said non-cell penetrating peptide has a molecular weight of less than about 25 kD.

P embodiment 9. The conjugate of one of P embodiments 1-9, wherein said non-cell penetrating peptide comprises a modified amino acid.

P embodiment 10. The conjugate of P embodiment 9, wherein said modified amino acid is an acetylated amino acid.

P embodiment 11. The conjugate of one of P embodiments 1-10, wherein said non-cell penetrating peptide is a STAT3 peptide comprising an acetylated amino acid at a position corresponding to amino acid position 685 of SEQ ID NO:1.

P embodiment 12. The conjugate of P embodiment 9, wherein said modified amino acid is a phosphorylated amino acid.

P embodiment 13. The conjugate of one of P embodiments 1-9 or 12, wherein said non-cell penetrating peptide is a gp130 peptide comprising a phosphorylated amino acid at a position corresponding to amino acid position 767 of SEQ ID NO:2.

P embodiment 14. The conjugate of one of P embodiments 1-9 or 12, wherein said non-cell penetrating peptide is a gp130 peptide comprising a phosphorylated amino acid at a position corresponding to amino acid position 905 of SEQ ID NO:2.

P embodiment 15. The conjugate of one of P embodiments 1-9 or 12, wherein said non-cell penetrating peptide comprises a gp130 peptide comprising a phosphorylated amino acid at a position corresponding to amino acid position 915 of SEQ ID NO:2.

P embodiment 16. The conjugate of one of P embodiments 1-15 wherein said non-cell penetrating peptide binds an intracellular target.

P embodiment 17. The conjugate of P embodiment 16, wherein said intracellular target is a signaling molecule or transcription factor.

P embodiment 18. The conjugate of P embodiment 17, wherein said signaling molecule is a phosphatase or kinase.

P embodiment 19. The conjugate of P embodiments 16-18, wherein said intracellular target is a karyopherin.

P embodiment 20. The conjugate of P embodiment 19, wherein said karyopherin is an exportin.

P embodiment 21. The conjugate of P embodiment 19 or 20, wherein said intracellular target is exportin 7.

P embodiment 22. The conjugate of P embodiment 21, wherein said intracellular target is an exportin 7 protein comprising the amino acid sequence of SEQ ID NO:5.

P embodiment 23. The conjugate of one of P embodiments 1-10 or 15-22, wherein said non-cell penetrating peptide is a STAT3 peptide.

P embodiment 24. The conjugate of one of P embodiments 1-10 or 15-23, wherein said non-cell penetrating peptide is an acetylated STAT3 peptide.

P embodiment 25. The conjugate of one of P embodiments 1-10 or 15-24, wherein said non-cell penetrating peptide comprises the sequence of SEQ ID NO:3.

P embodiment 26. The conjugate of P embodiment 16, wherein said intracellular target is a transcription factor.

P embodiment 27. The conjugate of P embodiment 16 or 26, wherein said intracellular target is STAT3.

P embodiment 28. The conjugate of P embodiment 27, wherein said intracellular target is a STAT3 protein comprising the amino acid sequence of SEQ ID NO:1.

P embodiment 29. The conjugate of one of P embodiments 1-16 or 26-28, wherein said non-cell penetrating peptide is a gp130 peptide.

P embodiment 30. The conjugate of one of P embodiments 1-16 or 26-29, wherein said non-cell penetrating peptide is a phosphorylated gp130 peptide.

P embodiment 31. The conjugate of one of P embodiments 1-16 or 26-30, wherein said non-cell penetrating peptide comprises the sequence of SEQ ID NO:4, SEQ ID NO:8 or SEQ ID NO:9.

P embodiment 32. The conjugate of one of P embodiments 1-31, wherein said non-cell penetrating peptide is a peptide which competes with a protein or peptide for binding an intracellular target.

P embodiment 33. The conjugate of P embodiment 32, wherein said protein or peptide comprises the sequence of SEQ ID NO:1, SEQ ID NO:2, SEQ ID NO:3, SEQ ID NO:4, SEQ ID NO:6 SEQ ID NO:7, SEQ ID NO:8 or SEQ ID NO:9.

P embodiment 34. The conjugate of P embodiment 32 or 33, wherein said protein or peptide is a STAT3 protein or fragment thereof.

P embodiment 35. The conjugate of P embodiment 32 or 33, wherein said protein or peptide is a gp130 protein or fragment thereof.

P embodiment 36. The conjugate of one of P embodiments 1-35, wherein said phosphorothioate nucleic acid is about 10, 20, 30, 40, 50, 60, 70, 80, 90, 100 or more nucleic acid residues in length.

P embodiment 37. The conjugate of one of P embodiments 1-36, wherein said phosphorothioate nucleic acid is from about 10 to about 30 nucleic acid residues in length.

P embodiment 38. The conjugate of one of P embodiments 1-37, wherein said phosphorothioate nucleic acid is about 20 nucleic acid residues in length.

P embodiment 39. The conjugate of one of P embodiments 1-38, wherein said phosphorothioate nucleic acid is a single stranded nucleic acid.

P embodiment 40. The conjugate of one of P embodiments 1-39, wherein said phosphorothioate nucleic acid is a phosphorothioate deoxyribonucleic acid.

P embodiment 41. The conjugate of one of P embodiments 1-40, wherein said chemical linker is a covalent linker.

P embodiment 42. The conjugate of one of P embodiments 1-41, wherein said linker comprises the structure of formula:

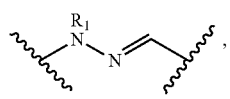

(I)

wherein $R^1$ is hydrogen, halogen, —$CF_3$, —CN, —$CCl_3$, —COOH, —$CH_2COOH$, —$CONH_2$, —OH, —SH, —$NO_2$, —$NH_2$, —$NHNH_2$, —$ONH_2$, —NHC═(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

P embodiment 43. The conjugate of one of P embodiments 1-42, wherein said linker is a non-immunogenic linker.

P embodiment 44. The conjugate of one of P embodiments 1-42, wherein said conjugate comprises a detectable moiety.

P embodiment 45. The conjugate of P embodiment 44, wherein said detectable moiety is attached to said non-cell penetrating peptide.

P embodiment 46. The conjugate of P embodiment 44, wherein said detectable moiety is attached to said phosphorothioate nucleic acid.

P embodiment 47. The conjugate of any one of P embodiments 1-46, bound to an intracellular target.

P embodiment 48. A cell comprising a peptide conjugate of any one of P embodiments 1-46.

P embodiment 49. A pharmaceutical composition comprising a peptide conjugate of any one of P embodiments 1-46 and a pharmaceutically acceptable carrier.

P embodiment 50. A method of treating cancer in a subject in need thereof, said method comprising administering to said subject a therapeutically effective amount of a cell penetrating peptide conjugate of one of P embodiments 1-46, thereby treating said cancer in said subject.

P embodiment 51. The method of P embodiment 50, wherein said cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

P embodiment 52. The method of P embodiment 50 or 51, said method comprising decreasing in said subject an expression level of BIRC5 or BclXL relative to a standard control.

P embodiment 53. A method of increasing expression of p53 in a cancer cell, said method comprising contacting a cancer cell with an effective amount of a cell penetrating peptide conjugate of one of P embodiments 1-46, thereby increasing expression of p53 in said cancer cell.

P embodiment 54. A method of inhibiting tumor vascularization in a subject in need thereof, said method comprising administering to said subject a therapeutically effective amount of a cell penetrating peptide conjugate of one of P embodiments 1-46, thereby inhibiting tumor vascularization in said subject.

P embodiment 55. A method of treating an inflammatory disease in a subject in need thereof, said method comprising administering to said subject a therapeutically effective amount of a cell penetrating peptide conjugate of one of P embodiments 1-46, thereby treating an inflammatory disease in said subject.

P embodiment 56. The method of P embodiment 55, said method comprising decreasing in said subject an expression level of FGA, IL1B or SERPINA3 relative to a standard control.

P embodiment 57. A method of treating pain in a subject in need thereof, said method comprising administering to said subject a therapeutically effective amount of a cell penetrating peptide conjugate of one of P embodiments 1-46, thereby treating pain in said subject.

P embodiment 58. The method of P embodiment 57, said method comprising decreasing in said subject an expression level of PTGS1, PTGS2, CALCA or SST relative to a standard control.

P embodiment 59. A method of treating a viral infection in a subject in need thereof, said method comprising administering to said subject a therapeutically effective amount of a cell penetrating peptide conjugate of one of P embodiments 1-46, thereby treating said viral infection in said subject.

P embodiment 60. The method of P embodiment 59, said method comprising decreasing in said subject an expression level of CXCR4, CCR5 or CD155 relative to a standard control.

P embodiment 61. The method of P embodiment 59 or 60, wherein said viral infection is an HIV infection or a poliovirus infection.

P embodiment 62. A method of inhibiting viral entry into a cell, said method comprising contacting a cell with an effective amount of a cell penetrating peptide conjugate of one of P embodiments 1-46, thereby inhibiting viral entry into said cell.

P embodiment 63. The method of P embodiment 62, said method comprising decreasing in said cell an expression level of CXCR4, CCR5 or CD155 relative to a standard control.

P embodiment 64. A method of inhibiting IL6 receptor signaling in a cell, said method comprising contacting a cell with an effective amount of a cell penetrating peptide conjugate of one of P embodiments 1-46, thereby inhibiting IL6 receptor signaling in said cell.

P embodiment 65. A method of delivering a non-cell penetrating peptide into a cell, said method comprising contacting a cell with a cell penetrating peptide conjugate of any one of P embodiments 1-46, thereby delivering said non-cell penetrating peptide into said cell.

EMBODIMENTS

Embodiment 1. A nucleic acid-peptide conjugate comprising:
(i) a non-cell penetrating peptide;
(ii) a phosphorothioate nucleic acid; and
(iii) a chemical linker attaching said phosphorothioate nucleic acid to the C-terminus of said non-cell penetrating peptide;
wherein said phosphorothioate nucleic acid enhances intracellular delivery of said non-cell penetrating peptide.

Embodiment 2. The conjugate of embodiment 1, wherein said non-cell penetrating peptide is about 5, 10, 15, 20 or 25 amino acids in length.

Embodiment 3. The conjugate of one of embodiments 1-2, wherein said non-cell penetrating peptide is at least 5 amino acids in length.

Embodiment 4. The conjugate of one of embodiments 1-3, wherein said non-cell penetrating peptide is about 8 amino acids in length.

Embodiment 5. The conjugate of one of embodiments 1-3, wherein said non-cell penetrating peptide is about 10 amino acids in length.

Embodiment 6. The conjugate of one of embodiments 1-3, wherein said non-cell penetrating peptide is about 11 amino acids in length.

Embodiment 7. The conjugate of one of embodiments 1-6, wherein said non-cell penetrating peptide is about 22 amino acids in length.

Embodiment 8. The conjugate of one of embodiments 1-6, wherein said non-cell penetrating peptide is about 13 amino acids in length.

Embodiment 9. The conjugate of one of embodiments 1-8, wherein said non-cell penetrating peptide has a molecular weight of less than about 25 kD.

Embodiment 10. The conjugate of one of embodiments 1-9, wherein said non-cell penetrating peptide comprises a modified amino acid.

Embodiment 11. The conjugate of embodiment 10, wherein said modified amino acid is an acetylated amino acid.

Embodiment 12. The conjugate of one of embodiments 1-11, wherein said non-cell penetrating peptide is a STAT3 peptide comprising an acetylated amino acid at a position corresponding to amino acid position 685 of SEQ ID NO:1.

Embodiment 13. The conjugate of embodiment 10, wherein said modified amino acid is a phosphorylated amino acid.

Embodiment 14. The conjugate of one of embodiments 1-10 or 13, wherein said non-cell penetrating peptide is a gp130 peptide comprising a phosphorylated amino acid at a position corresponding to amino acid position 767 of SEQ ID NO:2.

Embodiment 15. The conjugate of one of embodiments 1-10 or 13, wherein said non-cell penetrating peptide is a gp130 peptide comprising a phosphorylated amino acid at a position corresponding to amino acid position 905 of SEQ ID NO:2.

Embodiment 16. The conjugate of one of embodiments 1-10 or 13, wherein said non-cell penetrating peptide comprises a gp130 peptide comprising a phosphorylated amino acid at a position corresponding to amino acid position 915 of SEQ ID NO:2.

Embodiment 17. The conjugate of one of embodiments 1-16, wherein said non-cell penetrating peptide binds an intracellular target.

Embodiment 18. The conjugate of embodiment 17, wherein said intracellular target is a signaling molecule or transcription factor.

Embodiment 19. The conjugate of embodiment 18, wherein said signaling molecule is a phosphatase or kinase.

Embodiment 20. The conjugate of one of embodiments 17-19, wherein said intracellular target is c-MYC.

Embodiment 21. The conjugate of embodiment 20, wherein said intracellular target is a c-MYC protein comprising the amino acid sequence of SEQ ID NO:11.

Embodiment 22. The conjugate of one of embodiments 17-19, wherein said intracellular target is a karyopherin.

Embodiment 23. The conjugate of embodiment 22, wherein said karyopherin is an exportin.

Embodiment 24. The conjugate of embodiment 22 or 23, wherein said intracellular target is exportin 7.

Embodiment 25. The conjugate of embodiment 24, wherein said intracellular target is an exportin 7 protein comprising the amino acid sequence of SEQ ID NO:5.

Embodiment 26. The conjugate of one of embodiments 1-13 or 17-25, wherein said non-cell penetrating peptide is a STAT3 peptide.

Embodiment 27. The conjugate of one of embodiments 1-13 or 17-26, wherein said non-cell penetrating peptide is an acetylated STAT3 peptide.

Embodiment 28. The conjugate of one of embodiments 1-13 or 17-27, wherein said non-cell penetrating peptide comprises the sequence of SEQ ID NO:3.

Embodiment 29. The conjugate of embodiment 17, wherein said intracellular target is a transcription factor.

Embodiment 30. The conjugate of embodiment 17 or 29, wherein said intracellular target is STAT3.

Embodiment 31. The conjugate of embodiment 30, wherein said intracellular target is a STAT3 protein comprising the amino acid sequence of SEQ ID NO:1.

Embodiment 32. The conjugate of one of embodiments 1-19 or 29-31, wherein said non-cell penetrating peptide is a gp130 peptide.

Embodiment 33. The conjugate of one of embodiments 1-19 or 29-32, wherein said non-cell penetrating peptide is a phosphorylated gp130 peptide.

Embodiment 34. The conjugate of one of embodiments 1-11, 13, 17-21 or 29, wherein said non-cell penetrating peptide is a c-MYC binding peptide.

Embodiment 35. The conjugate of one of embodiments 1-21 or 29-34, wherein said non-cell penetrating peptide comprises the sequence of SEQ ID NO:4, SEQ ID NO:8, SEQ ID NO:9 or SEQ ID NO:10.

Embodiment 36. The conjugate of one of embodiments 1-35, wherein said non-cell penetrating peptide competes with a cellular protein or cellular peptide for binding an intracellular target.

Embodiment 37. The conjugate of embodiment 36, wherein said cellular protein or cellular peptide comprises the sequence of SEQ ID NO:1, SEQ ID NO:2, SEQ ID NO:3, SEQ ID NO:4, SEQ ID NO:6 SEQ ID NO:7, SEQ ID NO:8, SEQ ID NO:9, SEQ ID NO:10 or SEQ ID NO:12.

Embodiment 38. The conjugate of embodiment 36 or 37, wherein said cellular protein or cellular peptide is a STAT3 protein or fragment thereof.

Embodiment 39. The conjugate of embodiment 36 or 37, wherein said cellular protein or cellular peptide is a gp130 protein or fragment thereof.

Embodiment 40. The conjugate of embodiment 36 or 37, wherein said cellular protein or cellular peptide is a MAX protein or fragment thereof.

Embodiment 41. The conjugate of one of embodiments 1-39, wherein said phosphorothioate nucleic acid is about 10, 20, 30, 40, 50, 60, 70, 80, 90, 100 or more nucleic acid residues in length.

Embodiment 42. The conjugate of one of embodiments 1-41, wherein said phosphorothioate nucleic acid is from about 10 to about 30 nucleic acid residues in length.

Embodiment 43. The conjugate of one of embodiments 1-42, wherein said phosphorothioate nucleic acid is about 20 nucleic acid residues in length.

Embodiment 44. The conjugate of one of embodiments 1-43, wherein said phosphorothioate nucleic acid is a single stranded nucleic acid.

Embodiment 45. The conjugate of one of embodiments 1-44, wherein said phosphorothioate nucleic acid is a phosphorothioate deoxyribonucleic acid.

Embodiment 46. The conjugate of one of embodiments 1-45, wherein said chemical linker is a covalent linker.

Embodiment 47. The conjugate of one of embodiments 1-46, wherein said linker comprises the structure of formula:

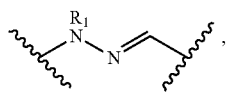

(I)

wherein $R^1$ is hydrogen, halogen, —$CF_3$, —CN, —$CCl_3$, —COOH, —$CH_2COOH$, —$CONH_2$, —OH, —SH, —$NO_2$, —$NH_2$, —$NHNH_2$, —$ONH_2$, —NHC=(O)$NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 48. The conjugate of one of embodiments 1-47, wherein said linker is a non-immunogenic linker.

Embodiment 49. The conjugate of one of embodiments 1-47, wherein said conjugate comprises a detectable moiety.

Embodiment 50. The conjugate of embodiment 49, wherein said detectable moiety is attached to said non-cell penetrating peptide.

Embodiment 51. The conjugate of embodiment 49, wherein said detectable moiety is attached to said phosphorothioate nucleic acid.

Embodiment 52. The conjugate of any one of embodiments 1-51, bound to an intracellular target.

Embodiment 53. A nucleic acid-peptide conjugate dimer comprising a phosphorothioate nucleic acid-peptide conjugate comprising any one of embodiments 1-52 and a non-phosphorothioated nucleic acid-peptide conjugate, wherein said non-phosphorothioated nucleic acid-peptide conjugate comprises a second non-cell penetrating peptide, a non-phosphorothioated nucleic acid and a chemical linker attaching said non-phosphorothioate nucleic acid to the C-terminus of said second non-cell penetrating peptide.

Embodiment 54. The conjugate dimer of 53, wherein said second non-cell penetrating peptide is a STAT3 peptide, an acetylated STAT3 peptide, a gp130 peptide, a phosphorylated gp130 peptide, or a c-MYC binding peptide.

Embodiment 55. The conjugate dimer of 53 or 54, wherein said second non-cell penetrating peptide the sequence of SEQ ID NO:3, SEQ ID NO:4, SEQ ID NO:6, SEQ ID NO:7, SEQ ID NO:8, SEQ ID NO:9 or SEQ ID NO:10.

Embodiment 56. A cell comprising a peptide conjugate of any one of embodiments 1-55.

Embodiment 57. A pharmaceutical composition comprising a peptide conjugate of any one of embodiments 1-55 and a pharmaceutically acceptable carrier.

Embodiment 58. A method of treating cancer in a subject in need thereof, said method comprising administering to said subject a therapeutically effective amount of a cell penetrating peptide conjugate of one of embodiments 1-55, thereby treating said cancer in said subject.

Embodiment 59. The method of embodiment 58, wherein said cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

Embodiment 60. The method of embodiment 58 or 59, further administering an effective amount of a second therapeutic agent to the subject.

Embodiment 61. The method of embodiment 60, wherein said second therapeutic agent is a cell penetrating peptide conjugate of one of embodiments 1-55.

Embodiment 62. The method of embodiment 58 or 59, said method comprising decreasing in said subject an expression level of BIRC5, BclXL or PD-L1 relative to a standard control.

Embodiment 63. A method of increasing expression of p53 in a cancer cell, said method comprising contacting a cancer cell with an effective amount of a cell penetrating peptide conjugate of one of embodiments 1-55, thereby increasing expression of p53 in said cancer cell.

Embodiment 64. A method of inhibiting tumor vascularization in a subject in need thereof, said method comprising administering to said subject a therapeutically effective amount of a cell penetrating peptide conjugate of one of embodiments 1-55, thereby inhibiting tumor vascularization in said subject.

Embodiment 65. A method of treating an inflammatory disease in a subject in need thereof, said method comprising administering to said subject a therapeutically effective amount of a cell penetrating peptide conjugate of one of embodiments 1-55, thereby treating an inflammatory disease in said subject.

Embodiment 66. The method of embodiment 65, said method comprising decreasing in said subject an expression level of FGA, IL1B or SERPINA3 relative to a standard control.

Embodiment 67. A method of treating pain in a subject in need thereof, said method comprising administering to said subject a therapeutically effective amount of a cell penetrating peptide conjugate of one of embodiments 1-55, thereby treating pain in said subject.

Embodiment 68. The method of embodiment 67, said method comprising decreasing in said subject an expression level of PTGS1, PTGS2, CALCA or SST relative to a standard control.

Embodiment 69. A method of treating a viral infection in a subject in need thereof, said method comprising administering to said subject a therapeutically effective amount of a cell penetrating peptide conjugate of one of embodiments 1-55, thereby treating said viral infection in said subject.

Embodiment 70. The method of embodiment 69, said method comprising decreasing in said subject an expression level of CXCR4, CCR5 or CD155 relative to a standard control.

Embodiment 71. The method of embodiment 69 or 70, wherein said viral infection is an HIV infection or a poliovirus infection.

Embodiment 72. A method of inhibiting viral entry into a cell, said method comprising contacting a cell with an effective amount of a cell penetrating peptide conjugate of one of embodiments 1-55, thereby inhibiting viral entry into said cell.

Embodiment 73. The method of embodiment 72, said method comprising decreasing in said cell an expression level of CXCR4, CCR5 or CD155 relative to a standard control.

Embodiment 74. A method of inhibiting IL6 receptor signaling in a cell, said method comprising contacting a cell with an effective amount of a cell penetrating peptide conjugate of one of embodiments 1-55, thereby inhibiting IL6 receptor signaling in said cell.

Embodiment 75. A method of delivering a non-cell penetrating peptide into a cell, said method comprising contacting a cell with a cell penetrating peptide conjugate of any one of embodiments 1-55, thereby delivering said non-cell penetrating peptide into said cell.

What is claimed is:

1. A nucleic acid-peptide conjugate comprising:
   (i) a non-cell penetrating peptide;
   (ii) a phosphorothioate nucleic acid; and
   (iii) a chemical linker attaching said phosphorothioate nucleic acid to the C-terminus of said non-cell penetrating peptide;
   wherein said phosphorothioate nucleic acid enhances intracellular delivery of said non-cell penetrating peptide; and
   wherein said non-cell penetrating peptide is about 5, 10, 15, 20 or 25 amino acids in length.

2. The conjugate of claim 1, wherein said non-cell penetrating peptide comprises a modified amino acid.

3. The conjugate of claim 1, wherein said non-cell penetrating peptide is a STAT3 peptide comprising an acetylated amino acid at a position corresponding to amino acid position 685 of SEQ ID NO: 1.

4. The conjugate of claim 1, wherein said non-cell penetrating peptide is a gp130 peptide comprising a phosphorylated amino acid at a position corresponding to amino acid position 767 of SEQ ID NO:2.

5. The conjugate of claim 1, wherein said non-cell penetrating peptide is a gp130 peptide comprising a phosphorylated amino acid at a position corresponding to amino acid position 905 of SEQ ID NO:2.

6. The conjugate of claim 1, wherein said non-cell penetrating peptide binds an intracellular target.

7. The conjugate of claim 6, wherein said intracellular target is a signaling molecule, transcription factor, or karyopherin.

8. The conjugate of claim 6, wherein said intracellular target is a c-MYC protein comprising the amino acid sequence of SEQ ID NO:11.

9. The conjugate of claim 6, wherein said intracellular target is an exportin 7 protein comprising the amino acid sequence of SEQ ID NO:5.

10. The conjugate of claim 1, wherein said non-cell penetrating peptide is an acetylated STAT3 peptide.

11. The conjugate of claim 1, wherein said non-cell penetrating peptide comprises the sequence of SEQ ID NO:3.

12. The conjugate of claim 6, wherein said intracellular target is a STAT3 protein comprising the amino acid sequence of SEQ ID NO:1.

13. The conjugate of claim 1, wherein said non-cell penetrating peptide comprises the sequence of SEQ ID NO:4, SEQ ID NO:8, SEQ ID NO:9 or SEQ ID NO:10.

14. An isolated cell comprising a peptide conjugate of claim 1.

15. A pharmaceutical composition comprising a peptide conjugate of claim 1 and a pharmaceutically acceptable carrier.

16. A method of treating cancer in a subject in need thereof, said method comprising administering to said subject a therapeutically effective amount of a cell penetrating peptide conjugate of claim 1, thereby treating said cancer in said subject.

17. A method of treating an inflammatory disease in a subject in need thereof, said method comprising administering to said subject a therapeutically effective amount of a cell penetrating peptide conjugate of claim 1, thereby treating an inflammatory disease in said subject.

18. A method of treating pain in a subject in need thereof, said method comprising administering to said subject a therapeutically effective amount of a cell penetrating peptide conjugate of claim 1, thereby treating pain in said subject.

19. A method of treating a viral infection in a subject in need thereof, said method comprising administering to said subject a therapeutically effective amount of a cell penetrating peptide conjugate of claim 1, thereby treating said viral infection in said subject.

* * * * *

SEQUENCE LISTING

```
<160> NUMBER OF SEQ ID NOS: 14

<210> SEQ ID NO 1
<211> LENGTH: 770
<212> TYPE: PRT
<213> ORGANISM: Homo sapiens

<400> SEQUENCE: 1

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
            35                  40                  45

Lys Glu Ser His Ala Thr Leu Val Phe His Asn Leu Leu Gly Glu Ile
        50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205
```

```
Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
            245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
            275                 280                 285

Gln Lys Val Ser Tyr Lys Gly Asp Pro Ile Val Gln His Arg Pro Met
290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
            355                 360                 365

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
610                 615                 620
```

```
Glu Lys Asp Ile Ser Gly Lys Thr Gln Ile Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770

<210> SEQ ID NO 2
<211> LENGTH: 918
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220
```

-continued

```
Pro His Asn Leu Ser Val Ile Asn Ser Glu Glu Leu Ser Ser Ile Leu
225                 230                 235                 240
Lys Leu Thr Trp Thr Asn Pro Ser Ile Lys Ser Val Ile Ile Leu Lys
            245                 250                 255
Tyr Asn Ile Gln Tyr Arg Thr Lys Asp Ala Ser Thr Trp Ser Gln Ile
        260                 265                 270
Pro Pro Glu Asp Thr Ala Ser Thr Arg Ser Ser Phe Thr Val Gln Asp
    275                 280                 285
Leu Lys Pro Phe Thr Glu Tyr Val Phe Arg Ile Arg Cys Met Lys Glu
290                 295                 300
Asp Gly Lys Gly Tyr Trp Ser Asp Trp Ser Glu Glu Ala Ser Gly Ile
305                 310                 315                 320
Thr Tyr Glu Asp Arg Pro Ser Lys Ala Pro Ser Phe Trp Tyr Lys Ile
                325                 330                 335
Asp Pro Ser His Thr Gln Gly Tyr Arg Thr Val Gln Leu Val Trp Lys
            340                 345                 350
Thr Leu Pro Pro Phe Glu Ala Asn Gly Lys Ile Leu Asp Tyr Glu Val
        355                 360                 365
Thr Leu Thr Arg Trp Lys Ser His Leu Gln Asn Tyr Thr Val Asn Ala
    370                 375                 380
Thr Lys Leu Thr Val Asn Leu Thr Asn Asp Arg Tyr Leu Ala Thr Leu
385                 390                 395                 400
Thr Val Arg Asn Leu Val Gly Lys Ser Asp Ala Ala Val Leu Thr Ile
                405                 410                 415
Pro Ala Cys Asp Phe Gln Ala Thr His Pro Val Met Asp Leu Lys Ala
            420                 425                 430
Phe Pro Lys Asp Asn Met Leu Trp Val Glu Trp Thr Thr Pro Arg Glu
        435                 440                 445
Ser Val Lys Lys Tyr Ile Leu Glu Trp Cys Val Leu Ser Asp Lys Ala
    450                 455                 460
Pro Cys Ile Thr Asp Trp Gln Gln Glu Asp Gly Thr Val His Arg Thr
465                 470                 475                 480
Tyr Leu Arg Gly Asn Leu Ala Glu Ser Lys Cys Tyr Leu Ile Thr Val
                485                 490                 495
Thr Pro Val Tyr Ala Asp Gly Pro Gly Ser Pro Glu Ser Ile Lys Ala
            500                 505                 510
Tyr Leu Lys Gln Ala Pro Pro Ser Lys Gly Pro Thr Val Arg Thr Lys
        515                 520                 525
Lys Val Gly Lys Asn Glu Ala Val Leu Glu Trp Asp Gln Leu Pro Val
    530                 535                 540
Asp Val Gln Asn Gly Phe Ile Arg Asn Tyr Thr Ile Phe Tyr Arg Thr
545                 550                 555                 560
Ile Ile Gly Asn Glu Thr Ala Val Asn Val Asp Ser Ser His Thr Glu
                565                 570                 575
Tyr Thr Leu Ser Ser Leu Thr Ser Asp Thr Leu Tyr Met Val Arg Met
            580                 585                 590
Ala Ala Tyr Thr Asp Glu Gly Gly Lys Asp Gly Pro Glu Phe Thr Phe
        595                 600                 605
Thr Thr Pro Lys Phe Ala Gln Gly Glu Ile Glu Ala Ile Val Val Pro
    610                 615                 620
Val Cys Leu Ala Phe Leu Leu Thr Thr Leu Leu Gly Val Leu Phe Cys
625                 630                 635                 640
```

```
Phe Asn Lys Arg Asp Leu Ile Lys Lys His Ile Trp Pro Asn Val Pro
                645                 650                 655

Asp Pro Ser Lys Ser His Ile Ala Gln Trp Ser Pro Thr Pro Pro
        660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
690                 695                 700

Pro Glu Asp Leu Lys Ser Leu Asp Leu Phe Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
                740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
        915

<210> SEQ ID NO 3
<211> LENGTH: 22
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (11)..(11)
<223> OTHER INFORMATION: ACETYLATION

<400> SEQUENCE: 3

Pro Asp Ile Pro Lys Glu Glu Ala Phe Gly Lys Tyr Cys Arg Pro Glu
1               5                   10                  15

Ser Gln Glu His Pro Cys
            20

<210> SEQ ID NO 4
<211> LENGTH: 11
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: MOD_RES
<222> LOCATION: (5)..(5)
<223> OTHER INFORMATION: PHOSPHORYLATION

<400> SEQUENCE: 4

Val His Ser Gly Tyr Arg His Gln Val Pro Ser
1               5                   10

<210> SEQ ID NO 5
<211> LENGTH: 1086
<212> TYPE: PRT
<213> ORGANISM: Homo sapiens

<400> SEQUENCE: 5

Met Ala Asp His Val Gln Ser Leu Ala Gln Leu Glu Asn Leu Cys Lys
1               5                   10                  15

Gln Leu Tyr Glu Thr Thr Asp Thr Thr Thr Arg Leu Gln Ala Glu Lys
            20                  25                  30

Ala Leu Val Glu Phe Thr Asn Ser Pro Asp Cys Leu Ser Lys Cys Gln
        35                  40                  45

Leu Leu Leu Glu Arg Gly Ser Ser Ser Tyr Ser Gln Leu Leu Ala Ala
    50                  55                  60

Thr Cys Leu Thr Lys Leu Val Ser Arg Thr Asn Asn Pro Leu Pro Leu
65                  70                  75                  80

Glu Gln Arg Ile Asp Ile Arg Asn Tyr Val Leu Asn Tyr Leu Ala Thr
                85                  90                  95

Arg Pro Lys Leu Ala Thr Phe Val Thr Gln Ala Leu Ile Gln Leu Tyr
            100                 105                 110

Ala Arg Ile Thr Lys Leu Gly Trp Phe Asp Cys Gln Lys Asp Asp Tyr
        115                 120                 125

Val Phe Arg Asn Ala Ile Thr Asp Val Thr Arg Phe Leu Gln Asp Ser
    130                 135                 140

Val Glu Tyr Cys Ile Ile Gly Val Thr Ile Leu Ser Gln Leu Thr Asn
145                 150                 155                 160

Glu Ile Asn Gln Ala Asp Thr Thr His Pro Leu Thr Lys His Arg Lys
                165                 170                 175

Ile Ala Ser Ser Phe Arg Asp Ser Ser Leu Phe Asp Ile Phe Thr Leu
            180                 185                 190

Ser Cys Asn Leu Leu Lys Gln Ala Ser Gly Lys Asn Leu Asn Leu Asn
        195                 200                 205

Asp Glu Ser Gln His Gly Leu Leu Met Gln Leu Leu Lys Leu Thr His
    210                 215                 220

Asn Cys Leu Asn Phe Asp Phe Ile Gly Thr Ser Thr Asp Glu Ser Ser
225                 230                 235                 240

Asp Asp Leu Cys Thr Val Gln Ile Pro Thr Ser Trp Arg Ser Ala Phe
                245                 250                 255

Leu Asp Ser Ser Thr Leu Gln Leu Phe Phe Asp Leu Tyr His Ser Ile
            260                 265                 270

Pro Pro Ser Phe Ser Pro Leu Val Leu Ser Cys Leu Val Gln Ile Ala
        275                 280                 285

Ser Val Arg Arg Ser Leu Phe Asn Asn Ala Glu Arg Ala Lys Phe Leu
    290                 295                 300

Ser His Leu Val Asp Gly Val Lys Arg Ile Leu Glu Asn Pro Gln Ser
305                 310                 315                 320
```

```
Leu Ser Asp Pro Asn Asn Tyr His Glu Phe Cys Arg Leu Leu Ala Arg
            325                 330                 335

Leu Lys Ser Asn Tyr Gln Leu Gly Glu Leu Val Lys Val Glu Asn Tyr
            340                 345                 350

Pro Glu Val Ile Arg Leu Ile Ala Asn Phe Thr Val Thr Ser Leu Gln
            355                 360                 365

His Trp Glu Phe Ala Pro Asn Ser Val His Tyr Leu Leu Ser Leu Trp
        370                 375                 380

Gln Arg Leu Ala Ala Ser Val Pro Tyr Val Lys Ala Thr Glu Pro His
385                 390                 395                 400

Met Leu Glu Thr Tyr Thr Pro Glu Val Thr Lys Ala Tyr Ile Thr Ser
                405                 410                 415

Arg Leu Glu Ser Val His Ile Ile Leu Arg Asp Gly Leu Glu Asp Pro
                420                 425                 430

Leu Glu Asp Thr Gly Leu Val Gln Gln Leu Asp Gln Leu Ser Thr
            435                 440                 445

Ile Gly Arg Cys Glu Tyr Glu Lys Thr Cys Ala Leu Leu Val Gln Leu
            450                 455                 460

Phe Asp Gln Ser Ala Gln Ser Tyr Gln Glu Leu Leu Gln Ser Ala Ser
465                 470                 475                 480

Ala Ser Pro Met Asp Ile Ala Val Gln Glu Gly Arg Leu Thr Trp Leu
                485                 490                 495

Val Tyr Ile Ile Gly Ala Val Ile Gly Gly Arg Val Ser Phe Ala Ser
                500                 505                 510

Thr Asp Glu Gln Asp Ala Met Asp Gly Glu Leu Val Cys Arg Val Leu
                515                 520                 525

Gln Leu Met Asn Leu Thr Asp Ser Arg Leu Ala Gln Ala Gly Asn Glu
            530                 535                 540

Lys Leu Glu Leu Ala Met Leu Ser Phe Phe Glu Gln Phe Arg Lys Ile
545                 550                 555                 560

Tyr Ile Gly Asp Gln Val Gln Lys Ser Ser Lys Leu Tyr Arg Arg Leu
                565                 570                 575

Ser Glu Val Leu Gly Leu Asn Asp Glu Thr Met Val Leu Ser Val Phe
            580                 585                 590

Ile Gly Lys Ile Ile Thr Asn Leu Lys Tyr Trp Gly Arg Cys Glu Pro
            595                 600                 605

Ile Thr Ser Lys Thr Leu Gln Leu Leu Asn Asp Leu Ser Ile Gly Tyr
            610                 615                 620

Ser Ser Val Arg Lys Leu Val Lys Leu Ser Ala Val Gln Phe Met Leu
625                 630                 635                 640

Asn Asn His Thr Ser Glu His Phe Ser Phe Leu Gly Ile Asn Asn Gln
                645                 650                 655

Ser Asn Leu Thr Asp Met Arg Cys Arg Thr Thr Phe Tyr Thr Ala Leu
                660                 665                 670

Gly Arg Leu Leu Met Val Asp Leu Gly Glu Asp Glu Gln Tyr Glu
            675                 680                 685

Gln Phe Met Leu Pro Leu Thr Ala Ala Phe Glu Ala Val Ala Gln Met
        690                 695                 700

Phe Ser Thr Asn Ser Phe Asn Glu Gln Glu Ala Lys Arg Thr Leu Val
705                 710                 715                 720

Gly Leu Val Arg Asp Leu Arg Gly Ile Ala Phe Ala Phe Asn Ala Lys
                725                 730                 735
```

```
Thr Ser Phe Met Met Leu Phe Glu Trp Ile Tyr Pro Ser Tyr Met Pro
            740                 745                 750

Ile Leu Gln Arg Ala Ile Glu Leu Trp Tyr His Asp Pro Ala Cys Thr
            755                 760                 765

Thr Pro Val Leu Lys Leu Met Ala Glu Leu Val His Asn Arg Ser Gln
        770                 775                 780

Arg Leu Gln Phe Asp Val Ser Ser Pro Asn Gly Ile Leu Leu Phe Arg
785                 790                 795                 800

Glu Thr Ser Lys Met Ile Thr Met Tyr Gly Asn Arg Ile Leu Thr Leu
                805                 810                 815

Gly Glu Val Pro Lys Asp Gln Val Tyr Ala Leu Lys Leu Lys Gly Ile
            820                 825                 830

Ser Ile Cys Phe Ser Met Leu Lys Ala Ala Leu Ser Gly Ser Tyr Val
            835                 840                 845

Asn Phe Gly Val Phe Arg Leu Tyr Gly Asp Asp Ala Leu Asp Asn Ala
            850                 855                 860

Leu Gln Thr Phe Ile Lys Leu Leu Ser Ile Pro His Ser Asp Leu
865                 870                 875                 880

Leu Asp Tyr Pro Lys Leu Ser Gln Ser Tyr Tyr Ser Leu Leu Glu Val
                885                 890                 895

Leu Thr Gln Asp His Met Asn Phe Ile Ala Ser Leu Glu Pro His Val
            900                 905                 910

Ile Met Tyr Ile Leu Ser Ser Ile Ser Glu Gly Leu Thr Ala Leu Asp
            915                 920                 925

Thr Met Val Cys Thr Gly Cys Cys Ser Cys Leu Asp His Ile Val Thr
            930                 935                 940

Tyr Leu Phe Lys Gln Leu Ser Arg Ser Thr Lys Lys Arg Thr Thr Pro
945                 950                 955                 960

Leu Asn Gln Glu Ser Asp Arg Phe Leu His Ile Met Gln Gln His Pro
                965                 970                 975

Glu Met Ile Gln Gln Met Leu Ser Val Leu Asn Ile Ile Phe Glu
            980                 985                 990

Asp Cys Arg Asn Gln Trp Ser Met Ser Arg Pro Leu Leu Gly Leu Ile
            995                 1000                1005

Leu Leu Asn Glu Lys Tyr Phe Ser Asp Leu Arg Asn Ser Ile Val
    1010                1015                1020

Asn Ser Gln Pro Pro Glu Lys Gln Gln Ala Met His Leu Cys Phe
    1025                1030                1035

Glu Asn Leu Met Glu Gly Ile Glu Arg Asn Leu Leu Thr Lys Asn
    1040                1045                1050

Arg Asp Arg Phe Thr Gln Asn Leu Ser Ala Phe Arg Arg Glu Val
    1055                1060                1065

Asn Asp Ser Met Lys Asn Ser Thr Tyr Gly Val Asn Ser Asn Asp
    1070                1075                1080

Met Met Ser
    1085

<210> SEQ ID NO 6
<211> LENGTH: 22
<212> TYPE: PRT
<213> ORGANISM: Artificial sequence
<220> FEATURE:
<223> OTHER INFORMATION: Synthetic polypeptide
```

```
<400> SEQUENCE: 6

Pro Asp Ile Pro Lys Glu Glu Ala Phe Gly Lys Tyr Cys Arg Pro Glu
1               5                   10                  15

Ser Gln Glu His Pro Cys
            20

<210> SEQ ID NO 7
<211> LENGTH: 22
<212> TYPE: PRT
<213> ORGANISM: Artificial sequence
<220> FEATURE:
<223> OTHER INFORMATION: Synthetic polypeptide

<400> SEQUENCE: 7

Pro Asp Ile Pro Lys Glu Glu Ala Phe Gly Arg Tyr Cys Arg Pro Glu
1               5                   10                  15

Ser Gln Glu His Pro Cys
            20

<210> SEQ ID NO 8
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (5)..(5)
<223> OTHER INFORMATION: PHOSPHORYLATION

<400> SEQUENCE: 8

Met Pro Lys Ser Tyr Leu Pro Gln Thr Val
1               5                   10

<210> SEQ ID NO 9
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (5)..(5)
<223> OTHER INFORMATION: PHOSPHORYLATION

<400> SEQUENCE: 9

Arg Gln Gly Gly Tyr Met Pro Gln
1               5

<210> SEQ ID NO 10
<211> LENGTH: 13
<212> TYPE: PRT
<213> ORGANISM: Artificial sequence
<220> FEATURE:
<223> OTHER INFORMATION: Synthetic polypeptide

<400> SEQUENCE: 10

Lys Asn Asp Thr His Gln Gln Asp Ile Asp Asp Leu Lys
1               5                   10

<210> SEQ ID NO 11
<211> LENGTH: 454
<212> TYPE: PRT
<213> ORGANISM: Homo sapiens
```

```
<400> SEQUENCE: 11

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
    195                 200                 205

Val Phe Pro Tyr Pro Leu Asn Asp Ser Ser Ser Pro Lys Ser Cys Ala
210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
    275                 280                 285

Gly Lys Arg Ser Glu Ser Gly Ser Pro Ser Ala Gly Gly His Ser Lys
290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
    355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415
```

```
Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
            435                 440                 445

Leu Arg Asn Ser Cys Ala
        450

<210> SEQ ID NO 12
<211> LENGTH: 160
<212> TYPE: PRT
<213> ORGANISM: Homo sapiens

<400> SEQUENCE: 12

Met Ser Asp Asn Asp Asp Ile Glu Val Glu Ser Asp Glu Glu Gln Pro
1               5                   10                  15

Arg Phe Gln Ser Ala Ala Asp Lys Arg Ala His His Asn Ala Leu Glu
            20                  25                  30

Arg Lys Arg Arg Asp His Ile Lys Asp Ser Phe His Ser Leu Arg Asp
        35                  40                  45

Ser Val Pro Ser Leu Gln Gly Glu Lys Ala Ser Arg Ala Gln Ile Leu
    50                  55                  60

Asp Lys Ala Thr Glu Tyr Ile Gln Tyr Met Arg Arg Lys Asn His Thr
65                  70                  75                  80

His Gln Gln Asp Ile Asp Asp Leu Lys Arg Gln Asn Ala Leu Leu Glu
            85                  90                  95

Gln Gln Val Arg Ala Leu Glu Lys Ala Arg Ser Ser Ala Gln Leu Gln
            100                 105                 110

Thr Asn Tyr Pro Ser Ser Asp Asn Ser Leu Tyr Thr Asn Ala Lys Gly
            115                 120                 125

Ser Thr Ile Ser Ala Phe Asp Gly Gly Ser Asp Ser Ser Ser Glu Ser
        130                 135                 140

Glu Pro Glu Glu Pro Gln Ser Arg Lys Lys Leu Arg Met Glu Ala Ser
145                 150                 155                 160

<210> SEQ ID NO 13
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 13
tccatgagct tcctgatgct                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 14
agcatcagga agctcatgga                                              20
```